United States Patent [19]

Smith

[11] 4,058,564

[45] Nov. 15, 1977

[54] ALIPHATIC 2-DECARBOXY-2-HYDROXYMETHYL-13,14-DIDEHYDRO-PG COMPOUNDS

[75] Inventor: Herman W. Smith, Kalamazoo, Mich.

[73] Assignee: The Upjohn Company, Kalamazoo, Mich.

[21] Appl. No.: 708,752

[22] Filed: July 26, 1976

[51] Int. Cl.$^2$ .................. C07C 35/06; C07C 43/27; C07C 49/46; C07C 49/58

[52] U.S. Cl. ....................... 260/586 R; 260/590 C; 260/611 R; 260/611 A; 260/613 R; 260/613 D; 260/617 R; 260/617 E; 260/618 E; 260/618 R; 424/331; 424/339; 424/340; 424/341; 424/343

[58] Field of Search .......... 260/468 D, 514 D, 586 R, 260/611 R, 617 R, 617 E

[56] References Cited

U.S. PATENT DOCUMENTS

| | | | |
|---|---|---|---|
| 3,932,496 | 1/1976 | Jung | 260/514 D |
| 3,935,254 | 1/1976 | Gandolfe et al. | 260/514 D |
| 3,984,400 | 10/1976 | Egglev et al. | 260/468 D |

OTHER PUBLICATIONS

Fried et al., "J. Med. Chem.," vol. 16, No. 4, pp. 429–430 (1973).

*Primary Examiner*—Norman Morgenstern
*Attorney, Agent, or Firm*—Robert A. Armitage

[57] ABSTRACT

This invention comprises certain analogs of the prostaglandins in which the C–1 carboxyl is replaced by a primary alcohol and the double bond between C–13 and C–14 is replaced by a triple bond. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

154 Claims, No Drawings

ALIPHATIC 2-DECARBOXY-2-HYDROXYMETHYL-13,14-DIDEHYDRO-PG COMPOUNDS

BACKGROUND OF THE INVENTION

This invention provides novel compositions of matter. This invention further provides novel processes for producing these compositions of matter.

Particularly this invention provides novel analogs of some of the known prostaglandins which differ from corresponding known prostaglandins in that these prostaglandin analogs have a primary alcohol in place of the carboxyl at C-1 and the analogs exhibit a triple bond between C-13 and C-14, that is —C≡C—.

The known prostaglandins include the PGE compounds, e.g. prostaglandin $E_1$ ($PGE_1$) and prostaglandin $E_2$ ($PGE_2$).

The known prostaglandins include $PGF_\alpha$ compounds, e.g. prostaglandin $F_{1\alpha}$ ($PGF_{1\alpha}$) and prostaglandin $F_{2\alpha}$ ($PGF_{2\alpha}$).

The known prostaglandins include PGA compounds, e.g. prostaglandin $A_1$ ($PGA_1$) and prostaglandin $A_2$ ($PGA_2$).

Each of the above mentioned known prostaglandins (PG's) is a derivative of prostanoic acid which has the following structure and carbon atom numbering

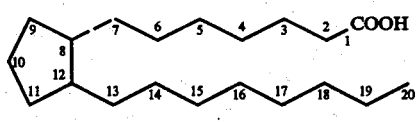

See, for example, Bergstrom et al., Pharmacol. Rev. 20, 1 (1968), and references cited therein. A systematic name for prostanoic acid is 7-[(2β-octyl)-cyclopent-1α-yl]heptanoic acid.

$PGE_1$ has the following structure:

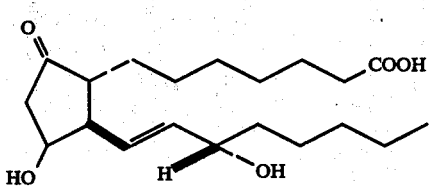

$PGE_2$ has the following structure:

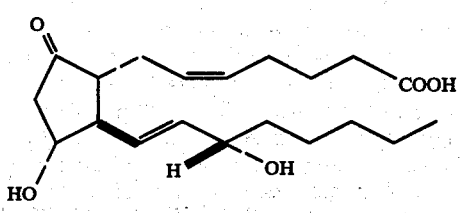

$PGF_{1\alpha}$ has the following structure:

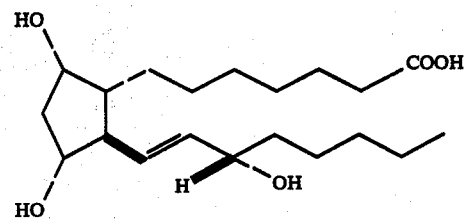

$PGF_{2\alpha}$ has the following structure:

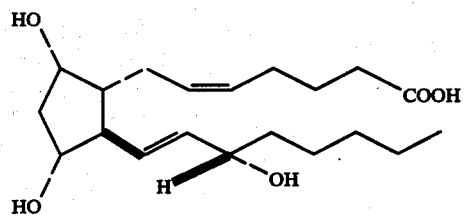

$PGA_1$ has the following structure:

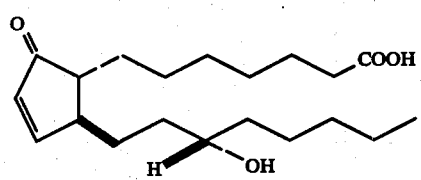

$PGA_2$ has the following structure:

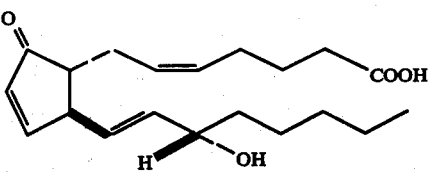

In the above formulas, as well as in the formulas hereinafter given, broken line attachments to the cyclopentane ring indicate substituents in alpha configuration i.e., below the plane of the cyclopentane ring. Heavy solid line attachments to the cyclopentane ring indicate substituents in beta configuration, i.e., above the plane of the cyclopentane ring. The use of wavy lines (∼) herein will represent attachment of substituents in either the alpha or beta configuration or attachment in a mixture of alpha and beta configurations.

The side-chain hydroxy at C-15 in the above formulas is in S configuration. See, Nature 212, 38 (1966) for discussion of the stereochemistry of the prostaglandins. Expressions such as C-13, C-14, C-15, and the like, refer to the carbon atom in the prostaglandin analog which is in the position corresponding to the position of the same number in prostanoic acid.

Molecules of the known prostaglandins each have several centers of asymmetry, and can exist in racemic (optically inactive) form and in either of the two enantiomeric (optically active) forms, i.e. the dextrorotatory and levorotatory forms. As drawn, the above formulas each represent the particular optically active form of the prostaglandin as is obtained from mammalian tissues, for example, sheep vesicular glands, swine lung, or human seminal plasma, or from carbonyl and/or double bond reduction of the prostaglandin so obtained. See, for example, Bergstrom et al., cited above. The mirror image of each of these formulas represents the other enantiomer of that prostaglandin. The racemic form of a prostaglandin contains equal numbers of both enantiomeric molecules, and one of the above formulas and the mirror image of that formula is needed to represent correctly the corresponding racemic prostaglandin. For convenience hereinafter, use of the term, prostaglandin or "PG" will means the optically active form of that prostaglandin thereby referred to with the same absolute configuration as $PGE_1$ obtained from mammalian tissues. When reference to the racemic form of one of those prostaglandins is intended, the word "racemic" or "dl" will precede the prostaglandin name.

The term "prostaglandin-type" (PG-type) product, as used herein, refers to any cyclopentane derivative which is useful for at least one of the same pharmacological purposes as the prostaglandins, as indicated herein.

The term prostaglandin-type intermediate, as used herein, refers to any cyclopentane derivative useful in preparing a prostaglandin-type product.

The formulas, as drawn herein, which depict a prostaglandin-type product or an intermediate useful in preparing a prostaglandin-type product each represent the particular stereoisomer of the prostaglandin-type product which is of the same relative stereochemical configuration as a corresponding prostaglandin obtained from mammalian tissues, or the particular stereoisomer of the intermediate which is useful in preparing the above stereoisomer of the prostaglandin-type product.

The term "prostaglandin analog", as used herein, represents that stereoisomer of a prostaglandin-type product which is of the same relative stereochemical configuration as a corresponding prostaglandin obtained from mammalian tissues or a mixture comprising that stereoisomer and the enantiomer thereof. In particular, where a formula is used to depict a prostaglandin-type compound herein, the term prostaglandin analog refers to the compound of that formula, or a mixture comprising that compound and the enantiomer thereof.

The various PG's named above, their esters, acylates and pharmacologically acceptable salts, are extremely potent in causing various biological responses. For that reason, these compounds are useful for phamcological purposes. See, for example, Bergstrom et al., Pharmacol. Rev. 20, 1 (1968) and references cited therein.

For the PGE compounds these biological responses include:

a. stimulating smooth muscle (as shown by tests, for example, on guinea pig ileum, rabbit duodenum, or gerbil colon);

b. effecting lipolytic activity (as shown by antagonism of epinephrine induced release of glycerol from isolated rat fat pads);

c. inhibiting gastric secretion and reducing undesirable gastrointestinal effects from systematic administration of prostaglandin synthetase inhibitors;

d. controlling spasm and facilitating breathing in asthmatic conditions;

e. decongesting nasal passages;

f. decreasing blood platelet adhesion (as shown by platelet to glass adhesiveness) and inhibiting blood platelet aggregation and thrombus formation induced by various physical stimuli (e.g., arterial injury) or chemical stimuli (e.g., ATP, ADP, serotinin, thrombin, and collagen);

g. affecting the reproductive organs of mammals as labor inducers, abortifacients, cervical dilators, regulators of the estrus, and regulators of the menstrual cycle; and h. accelerating growth of epidermal cells and keratin in animals.

For the $PGF_\alpha$ compound these biological responses include:

a. stimulating smooth muscle (as shown by tests on guinea pig ileum, rabbit duodenum, or gerbil colon);

b. inhibiting gastric secretion and reducing undesirable gastrointestinal effects from systematic administration of prostaglandin synthetase inhibitors;

c. decongesting nasal passages;

d. decreasing blood platelet adhesion (as shown by platelet to glass adhesiveness) and inhibiting blood platelet aggregation and thrombus formation induced by various physical stimuli (e.g., arterial injury) or chemical stimuli (e.g., ADP, ATP, serotinin, thrombin, and collagen); and e. affecting the reproductive organs of mammals as labor inducers, abortifacients, cervical dilators, regulators of the estrus, and regulators of the menstrual cycle.

For the PGA compounds these biological responses include:

a. stimulating smooth muscle (as shown in tests on guinea pig ileum, rabbit duodenum, or gerbil colon);

b. inhibiting gastric secretion and reducing undesirable gastrointestinal effects from systematic administration of prostaglandin synthetase inhibitors;

c. controlling spasm and facilitating breathing in asthmatic conditions;

d. decongesting nasal passages; and e. increasing kidney blood flow.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

The compounds so cited above as extremely potent in causing stimulation of smooth muscle are also highly active in potentiating other known smooth muscle stimulators, for example, oxytocic agents, e.g, oxytocin, and the various ergot alkaloids including derivatives and analogs thereof. Therefore, these compounds, for example, are useful in place of or in combination with less than usual amounts of these known smooth muscle stimulators, for example, to relieve the symptons of paralytic ileus, or to control or prevent atonic uterine bleeding after abortion or delivery, to aid in expulsion of the placenta, and during the puerperium. For the latter purpose, the prostaglandin is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acids levels, e.g., diabetes mellitus, vascular diseases, and hyperthyroidism.

The prostaglandins so cited above as useful in mammals, including man and certain useful animals, e.g., dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 µg. to about 500 µg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for that purpose by concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including $PGE_1$, $PGE_2$, $PGE_3$, 13,14-dihydro-$PGE_1$, and the corresponding 11-deoxy-PGE and PGA compounds. Prostaglandins are useful, for example, in reducing the undesirable gastrointestinal effects resulting from systemic administration of indomethacin, phenylbutazone, and aspirin. These are substances specifically mentioned in Partridge et al., as non-steroidal, anti-inflammatory agents. These are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally. Further, the prostaglandin can be conveniently administered orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

The prostaglandins so cited above as useful in the treatment of asthma, are useful, for example, as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, e.g., orally in the form of tablets, capsules, or liquids; rectally in the form of suppositories; parenterally, subcutaneously; or intramuscularly; with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, epinephrine, etc.); xanthine derivatives (theophylline and aminophylline); and corticosteroids (ACTH and prednisolone). Regarding use of these compounds see M. E. Rosenthale, et a., U.S. Pat. No. 3,644,638.

The prostaglandins so cited above as useful in mammals, including man, as nasal decongestants are used for this purpose in a dose range of about 10 µg. to about 10 mg. per ml. of a pharmacologically suitable liquid vehicle or as an aerosol spray, both for topical application.

The prostaglandins so cited above as useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

The prostaglandins so cited above as useful in place of oxytocin to induce labor are used in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

These compounds are further useful for controlling the reproductive cycle in menstruating female mammals, including humans. By the term menstruating female mammals is meant animals which are mature enough to menstruate, but not so old that regular menstruation has ceased. For that purpose the prostaglandin is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the prostaglandin is administered locally or systemically.

The prostaglandin, for example, is administered orally or vaginally at doses of about 5 to 50 1 mg. per treatment of an adult female human, with from one to five treatments per 24 hour period. Alternatively the prostaglandin is administered intramuscularly or subcutaneously a doses of about one to 25 mg. per treatment. The exact dosages for these purposes depend on the age, weight, and condition of the patient or animal.

These compounds are further useful in domestic animals as an abortifacient (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostaglandin is injected or applied in a feed at doses of 0.1-100 mg. per animal and may be combined with other agents such as steroids. Dosing schedules will depend on the species treated. For example, mares are given the prostaglandin 5 to 8 days after ovulation and return to estrus. Cattle, are treated at regular intervals over a 3 week period to advantageously bring all into estrus at the same time.

The PGA compounds are derivatives and salts thereof increase the flow of blood in the mammalian kidney, thereby increasing volume and electrolyte content of the urine. For that reason, PGA compounds are useful in managing cases of renal dysfunction, especially those involving blockage of the renal vascular bed. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 $\mu$g. per kg. of body weight or by intravenous infusion at a dose in the range 0.1 to 20 $\mu$g. per kg. of body weight per minute until the desired effect is obtained. Subsequent doses are given by intravenous, intramuscular, or subcutaneous injection or infusion in the range 0.05 to 2 mg. per kg. of body weight per day.

The compounds so cited above as promoters and accelerators of growth of epidermal cells and keratin are useful in animals, including humans, useful domestic animals, pets, zoological specimens, and laboratory animals for this purpose. For this reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For the above purposes, these compounds are preferably administered topically at or near the cite where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, where there is substantial fluid loss as in the case of extensive burns or skin loss due to other causes, systemic administration is advantageous, for example, by intravenous injection or infusion, separately or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 µg. per ml. of the prostaglandin. Especially for topical use, these prostaglandins are useful in combination with antibiotics, for example, gentamycin, neomycin, polymixin, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

Certain PG$_2$-type compounds wherein the C-13 to C-14 moiety is —C≡C— are known in the art. For example, see Gandolfi C., et al., Il Farmaco, 27, 1125, wherein 13,14-didehydro-PGF$_{2\alpha}$ and 13,14-didehydro-PGE$_2$ and their 15-epimers are described. See further, South African Pat. No. 73-2329, Derwent Farmdoc CPl 54179U, wherein 13,14-didehydro-PGF$_{2\alpha}$-, PGF$_{2\beta}$-, PGE$_2$-, and PGA$_2$-type compounds are disclosed with optional C-16 alkyl substitution and with optional oxa or thia substitution at the C-3-position. Further, the above South African Patent discloses the 8$\beta$,12$\alpha$-stereoisomer of the above-described compounds. See also J. Fried, et al., Tetrahedron Letters, 3899 (1963), which disloses 13,14-dihydro-PGF$_{2\alpha}$. See also U.S. Pat. No. 3,935,254.

Additionally certain 13-didehydro-PG$_1$-type compounds are known in the prior art. See, for example, J. Fried, et al., Annals, of the New York Academy of Science 18, 38 (1971), which discloses 7-oxa-13,14-didehydro-PGF$_{1\alpha}$. See also R. Pappo, et al., Tetrahedron Letters, 2627, 2630 (1972), which discloses racemic 13,14-dihydro-11$\beta$-PGE$_1$; and R. Pappo, et al., Annals. of the New York Academy of Science 18, 64 (1971), which discloses 13,14-didehydro-11$\beta$-PGB$_1$. Finally, see the following patents which disclose 13,14-dihydro-PGB$_1$-type compounds: Belgian Pat. No. 777,022 (Derwent Farmdoc CPl 43791T) German Offenlegunsschrift 1,925,672 (Derwent Farmdoc CPl 41,084), and German Offenlegungsschrift 2,357,781 (Derwent Farmdoc 42046V). See also U.S. Pat. No. 3,932,496.

Several 2-decarboxy-2-hydroxymethyl prostaglandin analogs are known in the art. See, Pike, J. E., et al., Journal of Organic Chemistry 34:3552 (1969) for disclosure of 2-decarboxy-2-hydroxymethyl-PGE$_1$. See also Crabbe, et al., Intra-Science Chemical Report 6:55 (1972) which discloses 2-decarboxy-2-hydroxymethyl-PGE$_2$ and PGF$_{2\alpha}$. See also Fried, J. et al., Annals of the New York Academy of Sciences 180:38 (1971) which discloses 2-decarboxy-2-hydroxymethyl-13,14-didehydro-(15RS)-PGF$_{1\alpha}$. Finally, see Pike, et al., Nobel Symposium 2:161 (1967) which discloses 2-decarboxy-2-hydroxymethyl-PGF$_{1\alpha}$.

Further, the following publications disclose 2-decarboxy-2-hydroxymethyl prostaglandin analogs: German Offenlegungsschrift 2,437,388 (Derwent Farmdoc CPl No. 43108W); Belgian Patent 817513 (Derwent Farmdoc CPl No. 07432W); German Offenlegungsschrift 2,404,653 (Derwent Farmdoc CPl No. 57272V); German Offenlegungsschrift 2,360,893 (Derwent Farmdoc CPl No. 45723V); Netherlands Pat. No. 7,206,361 (Derwent Farmdoc CPl No. 76383T); Netherlands Pat. No. 7,209,817 (Derwent Farmdoc CPl No. 05789U); Netherlands Pat. No. 7,209,738 (Derwent Farmdoc Cpl No. 05786U); Netherlands Pat. No. 7,306,030 (Derwent Farmdoc CP1 No. 71295U); Netherlands Pat. No. 7,313,322 (Derwent Farmdoc CPl No. 28414V); Belgian Pat. No. 815,372 (Derwent Farmdoc CPl No. 84521V); and Belgian Patent 815,742 (Derwent Farmdoc CPl No. 81796V). Finally, see U.S. Pat. No. 3,852,377 which describes PGF-tetraols, and Belgian Pat. No. 722,031 (Derwent Farmdoc CPl No. 37,298).

SUMMARY OF THE INVENTION

This invention provides novel prostaglandin analogs, esters of these analogs, and pharmacologically acceptable salts of these analogs.

This invention further provides lower alkanoates of these analogs.

This invention further provides novel processes for preparing these analogs.

In particular, this invention comprises:

a. a prostaglandin analog of the formula

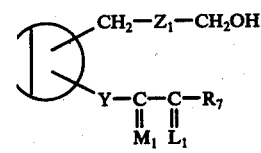

wherein 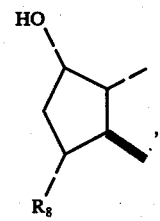 is

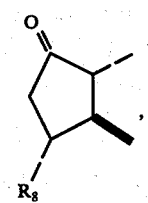

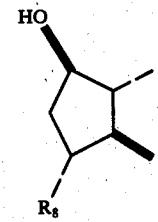

-continued

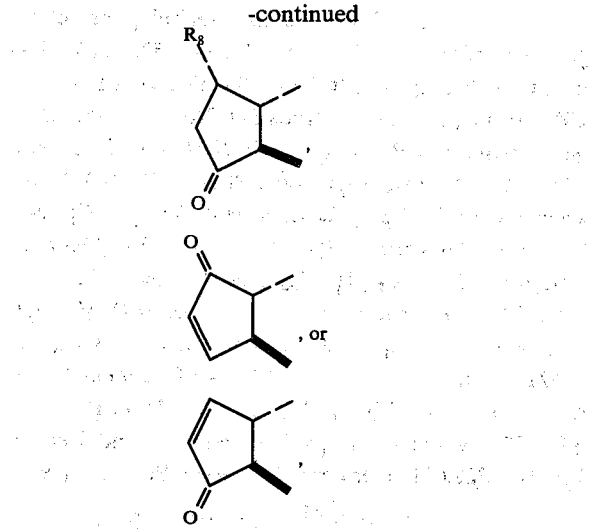

wherein R$_8$ is hydrogen or hydroxy;
  wherein Y is —C≡C—;
  wherein M$_1$ is or

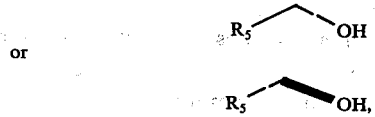

wherein R$_5$ is hydrogen or methyl;
  wherein L$_1$ is

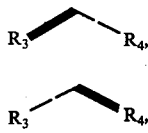

or a mixture of

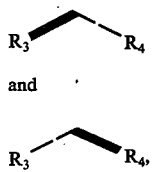

wherein R$_3$ and R$_4$ are hydrogen, methyl or fluoro, being the same or different, with the proviso that one of R$_3$ and R$_4$ is methyl only when the other is hydrogen or methyl;
  wherein Z$_1$ is
  (1) cis-CH=CH—CH$_2$—(CH$_2$)$_g$—CH$_2$—,
  (2) cis-CH=CH—CH$_2$ (CH$_2$)$_g$—CF$_2$—,
  (3) cis-CH$_2$—CH=CH—(CH$_2$)$_g$—CH$_2$—,
  (4) —(CH$_2$)$_3$—(CH$_2$)$_g$—CH$_2$—,
  (5) —(CH$_2$)$_3$—(CH$_2$)$_g$—CF$_2$—,
  (6) —CH$_2$—O—(CH$_2$)$_g$—CH$_2$—,

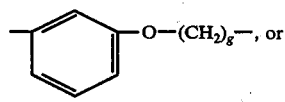 (7)

-continued

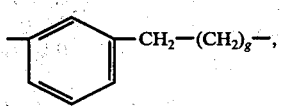 (8)

wherein g is one, 2, or 3; and
  wherein R$_7$ is —(CH$_2$)$_m$—CH$_3$, wherein m is one to 5, inclusive, or

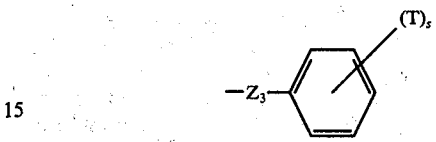

wherein Z$_3$ is methylene or oxa, s is zero, one, 2, or 3 and T is chloro, fluoro, trifluoromethyl, alkyl of one to 3 carbon atoms, inclusive, or alkoxy of one to 3 carbon atoms, inclusive, the various T's being the same or different, with the proviso that not more than two T's are other than alkyl; with the further proviso that Z$_3$ is oxa only when R$_3$ and R$_4$ are hydrogen or methyl, being the same or different.

Within the scope of the novel prostaglandin analogs of this invention, there are represented above:

a. 2-decarboxy-2-hydroxymethyl-13,14-didehydro-PGE-type compounds when the cyclopentane moiety is:

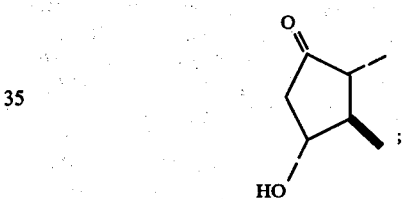

b. 2-decarboxy-2-hydroxymethyl-13,14-didehydro-PGF$_\alpha$-type compounds when the cyclopentane moiety is:

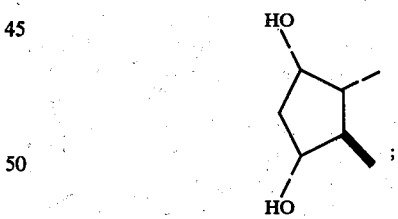

c. 2-decarboxy-2-hydroxymethyl-13,14-didehydro-PGD-type compounds when the cyclopentane moiety is:

d. 2-decarboxy-2-hydroxymethyl-13,14-didehydro-9-deoxy-PGD-type compounds when the cyclopentane moiety is:

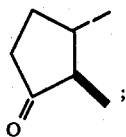

e. 2-decarboxy-2-hydroxymethyl-13,14-didehydro-9-deoxy-9,10-didehydro-PGD-type compounds when the cyclopentane moiety is:

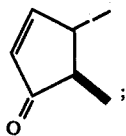

f. 2-decarboxy-2-hydroxymethyl-13,14-didehydro-11-deoxy-PGE-type compounds when the cyclopentane moiety is:

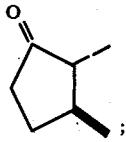

g. 2-decarboxy-2-hydroxymethyl-13,14-didehydro-11-deoxy-PGF$_\alpha$-type compounds when the cyclopentane moiety is:

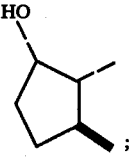

and h. 2-decarboxy-2-hydroxymethyl-13,14-didehydro-PGA-type compounds when the cyclopentane moiety is:

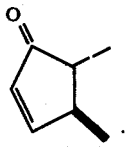

Those prostaglandin analogs herein wherein $Z_1$ is cis-CH=CH—CH$_2$—CH$_2)_g$—C(R$_2$)$_2$— wherein $R_2$ is hydrogen or fluoro, are named as "PG$_2$" compounds. When R$_2$ is fluoro these compounds are further characterized as "2,2-difluoro" PG-type compounds. When $g$ is 2 or 3 the prostaglandin analogs so described are "2a-homo" or "2a,2b-dihomo" compounds, since in this event the carboxy terminated side chain contains 8 or 9 carbon atoms, respectively, in place of the 7 carbon atoms contained in PGE$_1$. These additional carbon atoms are considered as though they were inserted between the C-2 and C-3 positions. Accordingly, these additional carbon atoms are referred to as C-2a and C-2b, counting from the C-2 to the C-3 position.

Further when $Z_1$ is —(CH$_2$)$_3$—(CH$_2$)$_g$—C(R$_2$)$_2$—, wherein $g$ is as defined above, the compounds so described are "PG$_1$" compounds. When $g$ is 2 or 3, the "2a-homo" and "2a,2b-dihomo" compounds are described as is discussed in the preceeding paragraph. Also, "2,2-difluoro" compounds are described when R$_2$ is fluoro.

When $Z_1$ is —CH$_2$—O—(CH$_2$)$_g$—CH$_2$— the compounds so described are named as "5-oxa-PG$_1$" compounds. When $g$ is 2 or 3, the compounds so described are "2a-homo" or "2a,2b-dihomo" compounds, respectively, as discussed above.

When $Z_1$ is cis-CH$_2$—CH=CH—(CH$_2$)$_g$—CH$_2$—, wherein $g$ is as defined above, the compounds so described are cis-4,5-didehydro-PG$_1$" compounds. When $g$ is 2 or 3, the compounds so described are further characterized as "2a-homo" or "2a,2b-dihomo" compounds, respectively, as discussed above.

When R$_7$ is —(CH$_2$)$_m$—CH$_3$, wherein m is as defined above, the compounds so described are named as "19,20-dinor", "20-nor", "20-methyl", or "20- ethyl" compounds when m is one, 2, 4 or 5, respectively.

When R$_7$ is

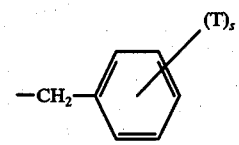

wherein T and s are as defined above, the compounds so described are named as "17-phenyl-18,19,20-trinor" compounds, when s is O. When s is one, 2, or 3, the corresponding compounds are named as "17-(substituted phenyl)-18,19,20-trinor" compounds.

When R$_7$ is

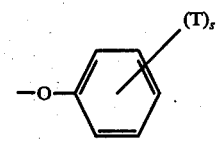

wherein T and s are as defined above, and neither R$_3$ nor R$_4$ is methyl, the compounds so described are named as "16-phenoxy-17,18,19,20-tetranor" compounds, when s is zero. When s is one, 2, or 3, the corresponding compounds are named as "16-(substituted phenoxy)-17,18,19,20-tetranor" compounds. When one and only one of R$_3$ and R$_4$ is methyl or both R$_3$ and R$_4$ are methyl, then the corresponding compounds wherein R$_7$ is as defined in this paragraph are named as "16-phenoxy or 16-(substituted phenoxy)-18,19,20-trinor" compounds or "16-methyl-16-phenoxy or 16-(substituted phenoxy)-18,19,20-trinor" compounds, respectively.

When at least one of R$_3$ and R$_4$ is not hydrogen then (except for the 16-phenoxy compounds discussed above) there are described the "16-methyl" (one and only one of R$_3$ and R$_4$ is methyl), "16,16-dimethyl" (R$_3$ and R$_4$ are both methyl), "16-fluoro" (one and only one of R$_3$ and R$_4$ is fluoro), "16,16-difluoro" (R$_3$ and R$_4$ are fluoro) compounds. For those compounds wherein R$_3$ and R$_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When R$_5$ is methyl, the compounds so described are named as "15-methyl" compounds.

For a general description of the nomenclature employed herein, see N. A. Nelson, J. of Med. Chem. 17, 911 (1974).

PG-type compounds as drawn herein which have an hydroxy at C-15 in the beta configuration are of the opposite relative stereochemical configuration at C-15 as that of PGE₁, and are therefore named as "15-epi" compounds. When the alpha hydroxy configuration is present, no special designation of this stereochemistry is provided in naming the compound.

Examples of

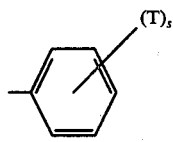

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)-ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)-chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3-, or 4-)chloro-2-fluorophenyl, o-, m-, or p-(trifluoromethyl)phenyl, (o-, m-, or p-)methoxyphenyl, (o-, m-, or p-)ethoxyphenyl, (4- or 5-)chloro-2-methoxyphenyl, and 2,4-dichloro(5- or 6-)methylphenyl.

The novel prostaglandin analogs of this invention correspond to the prostaglandins described above, in that the novel prostaglandin analogs exhibit prostaglandin-like activity.

Specifically the PGE- and 11-deoxy-PGE-type compounds of this invention correspond to the PGE compounds described above, in that these novel PGE- and 11-deoxy-PGE-type compounds are useful for each of the above-described purposes for which the PGE compounds are used, and are used in the same manner as the PGE compounds, as described above.

The PGF$_\alpha$- and 11-deoxy-PGF$_\alpha$-type compounds of this invention correspond to the PGF$_\alpha$ compounds described above, in that these novel PGF$_\alpha$- and 11-deoxy-PGF$_\alpha$-type compounds are useful for each of the above-described purposes for which the PGF$_\alpha$ compounds are used, and are used in the same manner as the PGF$_\alpha$ compounds, as described above.

The PGD-, 9-deoxy-PGD-, and 9,10-didehydro-9-deoxy-PGD-type compounds of this invention correspond to the PGE or PGF$_\alpha$ compounds described above, in that these novel PGD-, 9-deoxy-PGE-, or 9-deoxy-9,10-didehydro-PGD-type compounds are useful for each of the above-described purposes for which either the PGE or PGF$_\alpha$ compounds are used, and are used in the same manner as the PGE or PGF$_\alpha$ compounds, as described above.

The PGA-type compounds of this invention correspond to the PGA compounds described above, in that these novel PGA-type compounds are useful for each of the above described purposes for which the PGA compounds are used, and are used in the same manner as the PGA compounds, as described above.

The prostaglandins described above, are all potent in causing multiple biological responses even at low doses. Moreover, for many applications, these prostaglandins have an inconveniently short duration of biological activity. In striking contrast, the novel prostaglandin analogs of this invention are substantially more selective with regard to potency in causing prostaglandin-like biological responses, and have a substantially longer duration of biological activity. Accordingly, each of these novel prostaglandin analogs is surprisingly and unexpectedly more useful than one of the corresponding prostaglandins described above for at least one of the pharmacological purposes indicated above for the latter, because it has a different and narrower spectrum of biological potency than the known prostaglandin, and therefore is more specific in its activity and causes smaller and fewer undesired side effects than when the prostaglandin is used for the same purpose. Moreover because of its prolonged activity, fewer and smaller doses of the novel prostaglandin analog are frequently effective in attaining the desired result.

Another advantage of the novel prostaglandin analogs of this invention, especially the preferred PG analogs defined hereinbelow, compared with the corresponding prostaglandins, is that these novel PG analogs are administered effectively orally, sublingually, intravaginally, buccally, or rectally in those cases wherein the corresponding prostaglandin is effective only by the intravenous, intramuscular, or subcutaneous injection or infusion methods of administration indicated above as uses of these prostaglandins. These alternate routes of administration are advantageous because they facilitate maintaining uniform levels of these compounds in the body with fewer, shorter, or smaller doses, and make possible self-administration by the patient.

Accordingly, the novel prostaglandin analogs of this invention are administered in various ways for various purposes: e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For intravenous injection or infusion, sterile aqueous isotonic solutions are preferred. For subcutaneous or intramuscular injection, sterile solutions or suspension of a compound in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The chemical structure of the novel 11-deoxy-2-decarboxy-2-hydroxymethyl-PGE-type compounds of this invention renders them less sensitive to dehydration and rearrangement than the corresponding prostaglandins, and these compounds accordingly exhibit a surprising and unexpected stability and duration of self life.

To obtain the optimum combination of biological response specificity, potency, and duration of activity, certain compounds within the scope of this invention are preferred.

It is preferred that the carboxy-terminated side chain contain either 7 or 9 carbon (or carbon and oxygen) atoms, especially preferred that it contain 7, i.e., the natural chain length of the prostaglandins. Further when $R_7$ is —$(CH_2)_m$—$CH_3$, it is preferred that m be 3. For those compounds where $R_7$ is

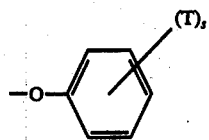

or

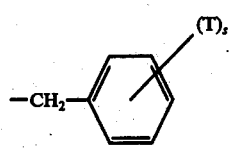

it is preferred that s be zero or one and T be chloro, fluoro, or trifluoromethyl.

For those compounds wherein at least one of $R_3$ and $R_4$ is methyl or fluoro, it is preferred that $R_5$ be hydrogen. For those compounds wherein $R_5$ is methyl, it is preferred that $R_3$ and $R_4$ both be hydrogen. For those compounds wherein $R_7$ is

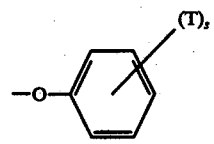

or

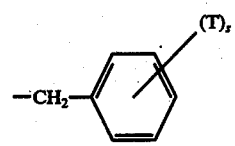

it is preferred $R_3$ and $R_4$ be hydrogen.

It is further preferred that the 15-hydroxy not be of the 15-epi configuration, i.e., that the hydroxy be in the alpha configuration when the formulas of the novel PG analogs are as drawn herein.

Especially preferred are those compounds which satisfy two or more of the above preferences. Further, the above preferences are expressly intended to describe the preferred compounds within the scope of any generic formula of novel prostaglandin analogs disclosed herein. Thus, for example the above preferences describe preferred compounds within the scope of each formula of a prostaglandin analog provided in the Tables hereinafter.

In another aspect of the interpretation the preferences herein, the various prostaglandin cyclopentane ring structures as employed herein are each representative of a particular "parent structure" which is useful in naming and categorizing the novel prostaglandin analogs disclosed herein. Further, where a formula depicts a genus of PG analogs disclosed herein evidencing a single cyclopentane ring structure, then each corresponding genus of PG analogs evidencing one of the remaining cyclopentane ring structures cited herein for novel prostaglandin analogs is intended to represent an equally preferred genus of compounds. Thus, for example, for each genus of $PGF_\alpha$-type products depicted by a formula herein, the corresponding genera of PGD-, PGE-, and 11-deoxy-$PGF_\alpha$-type products are equally preferred embodiments of the invention as the genus of $PGF_\alpha$-type products.

Finally where subgeneric grouping of PG analogs of any cyclopentane ring structure are described herein, then the corresponding subgeneric grouping of PG analogs of each of the remaining cyclopentane ring structures are intended to represent equally preferred embodiments of the present invention.

The Charts herein describe methods whereby the novel prostaglandin analogs of this invention are prepared.

Chart A

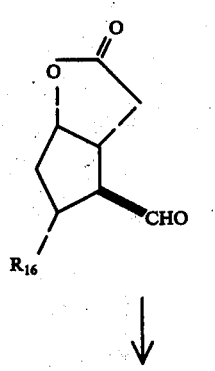

XXI

-continued
Chart A
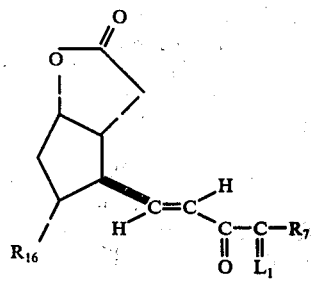
XXII
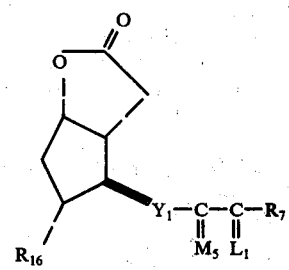
XXIII
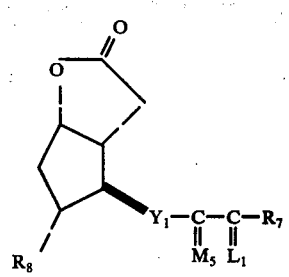
XXIV
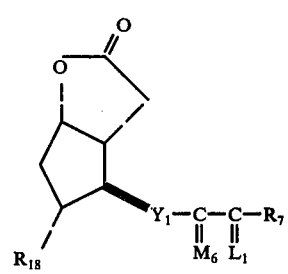
XXV

-continued
Chart A
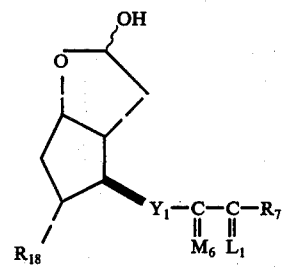 XXVI
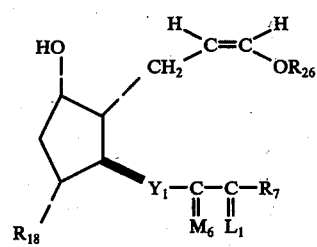 XXVII
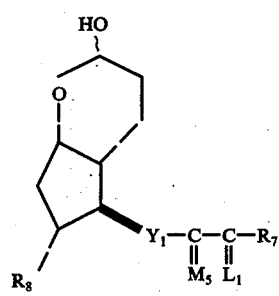 XXVIII
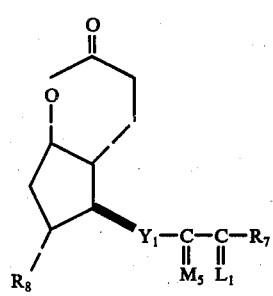 XXIX -continued
Chart A
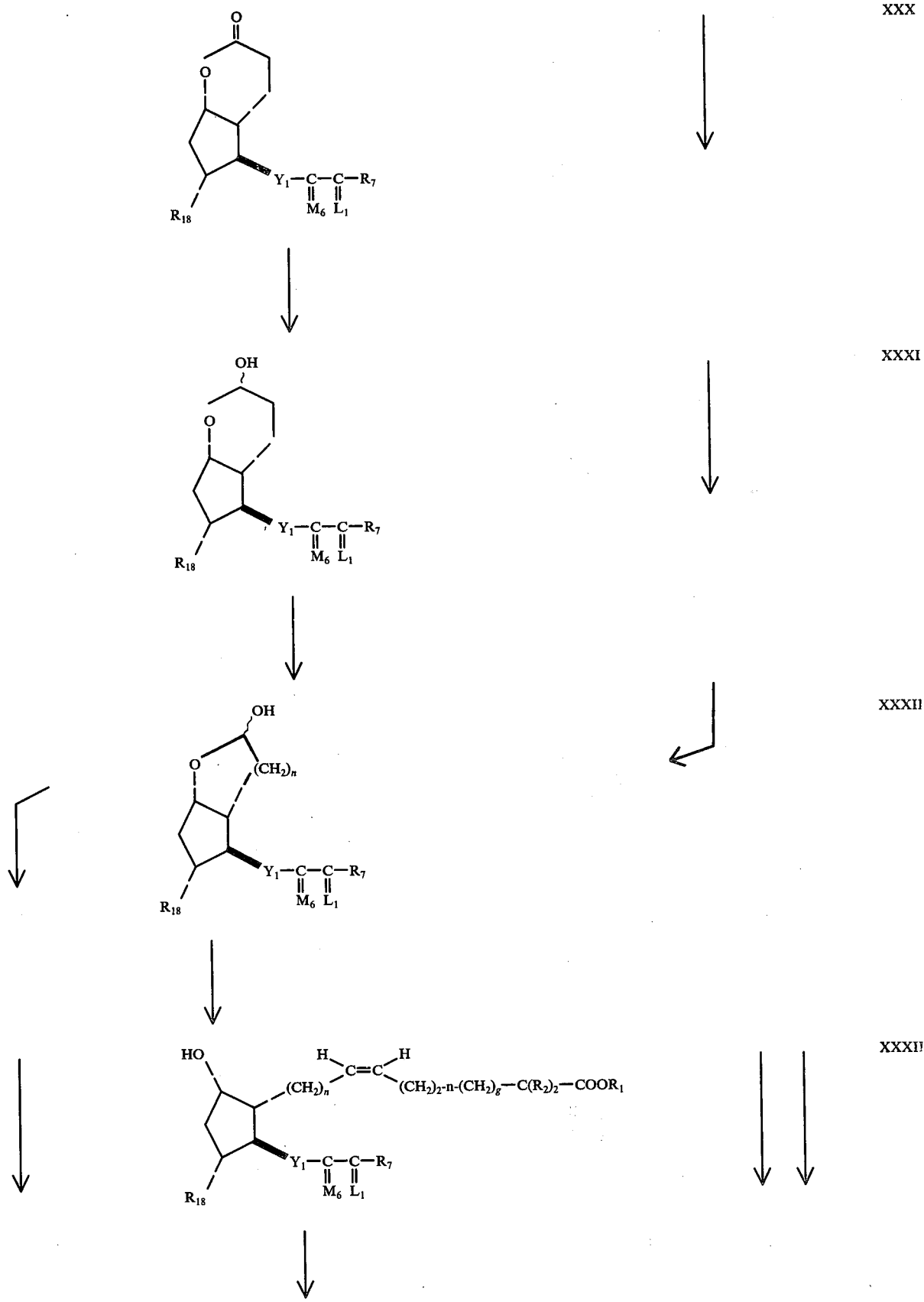
XXX
XXXI
XXXII
XXXII

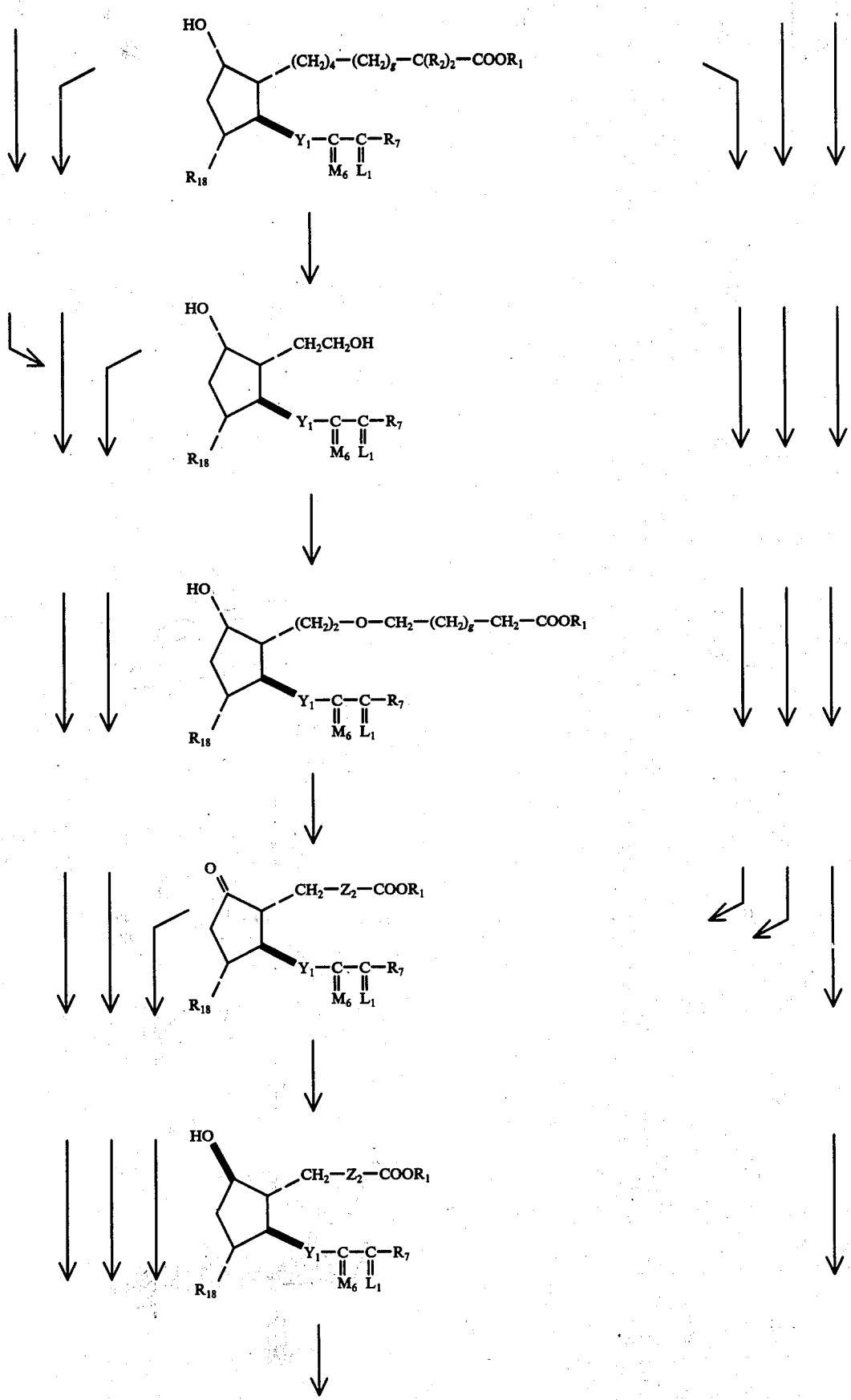

-continued
Chart A
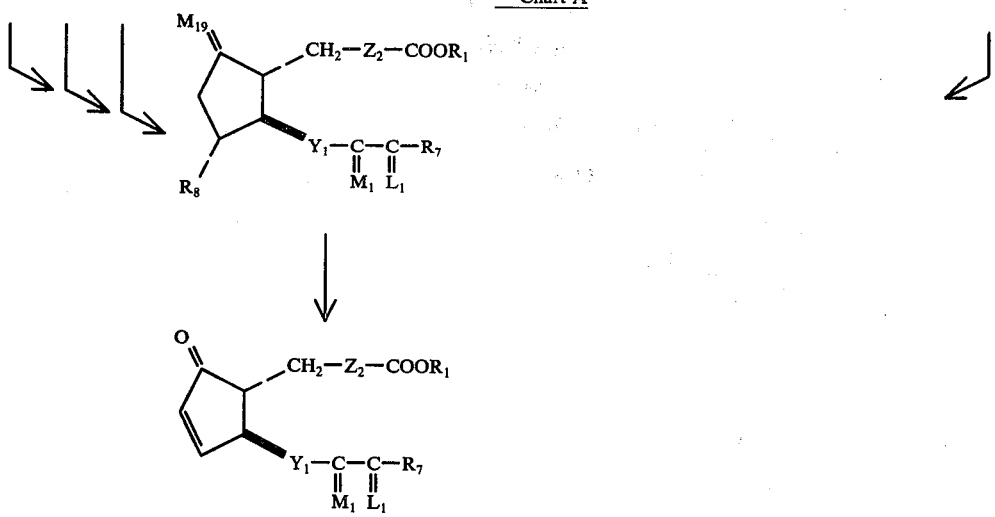
XXXIX
XL
Chart B
LXI
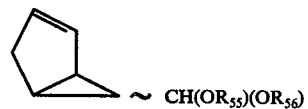
-continued
Chart B
LXV
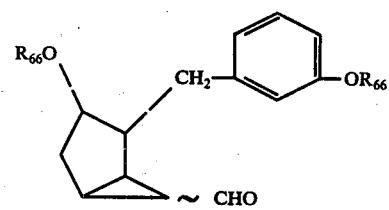
LXII
LXIII
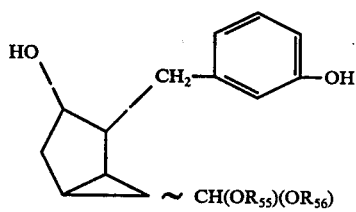
LXVI
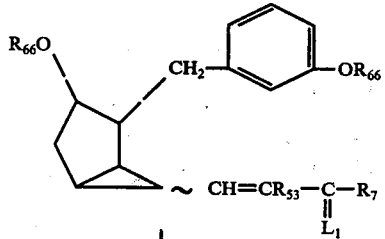
LXIV
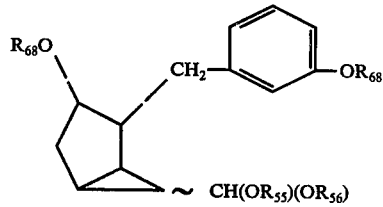
LXVII
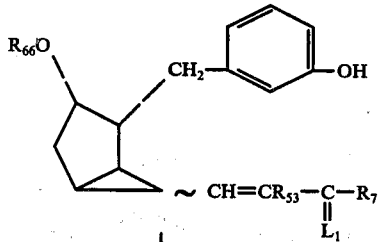

4,058,564
-continued
Chart B
LXVIII
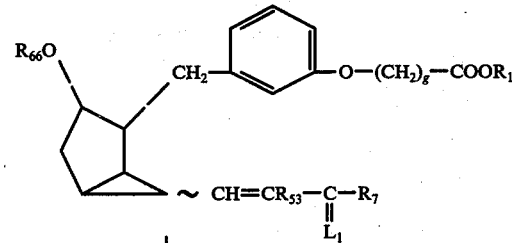
LXIX
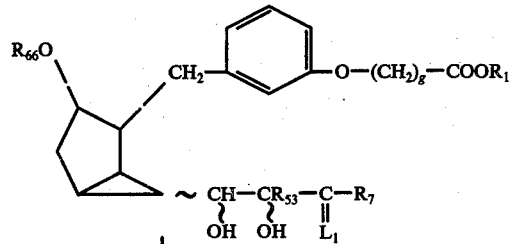
LXX
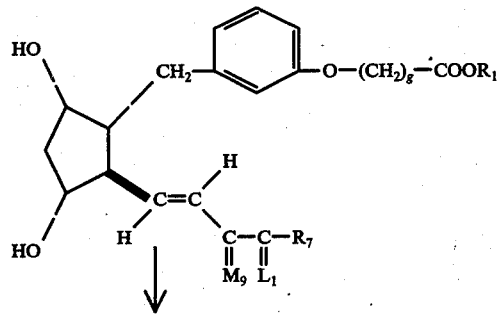
LXXI
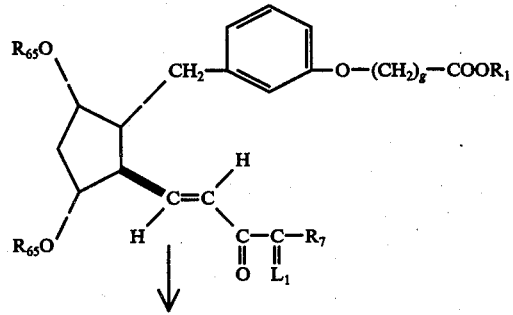
LXXII
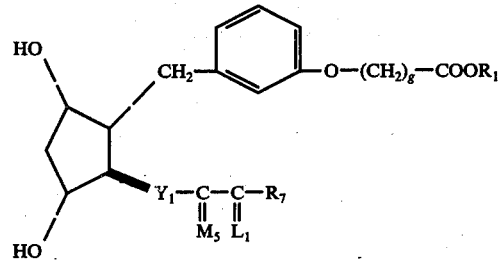
-continued
Chart B
LXXIII
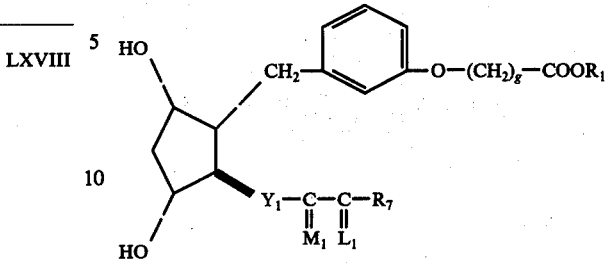
Chart C
LXXVI
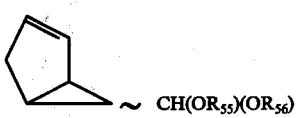
↓
LXXVII
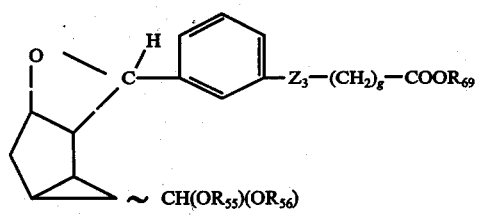
↓
LXXVIII
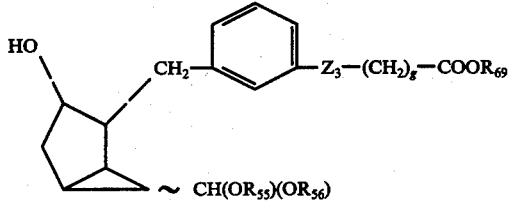
↓
LXXIX
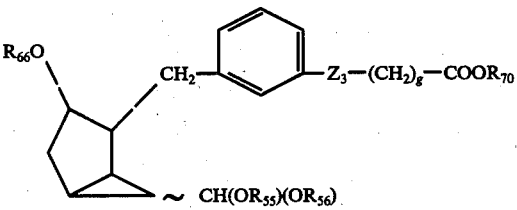
↓

-continued
Chart C
LXXX
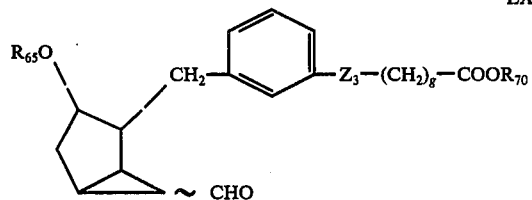
LXXXI
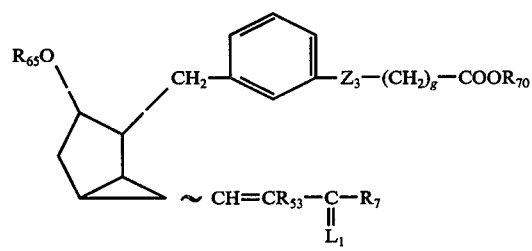
LXXXII
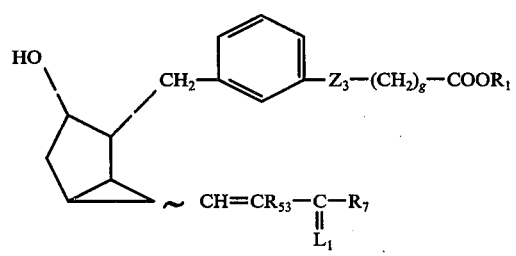
LXXXIII
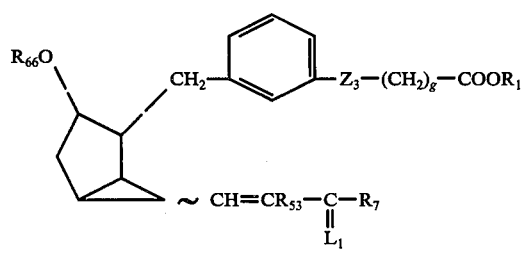
-continued
Chart C
LXXXIV
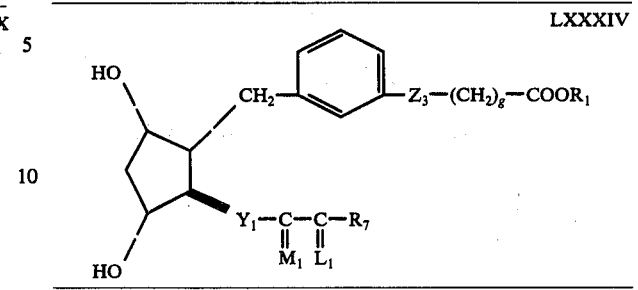
Chart D
XCI
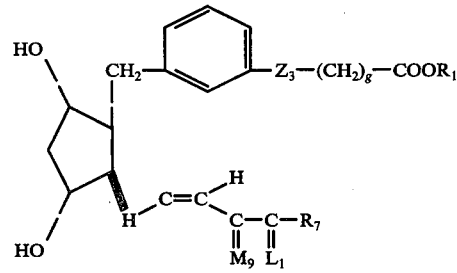
XCII
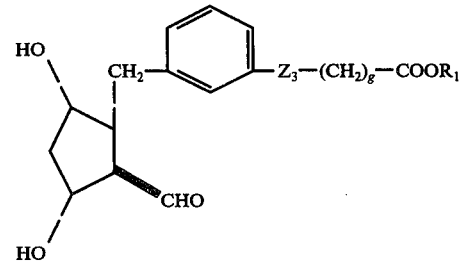
XCIII
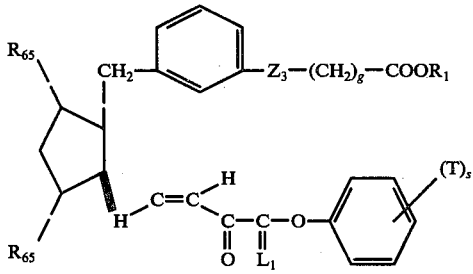

33
-continued
Chart D
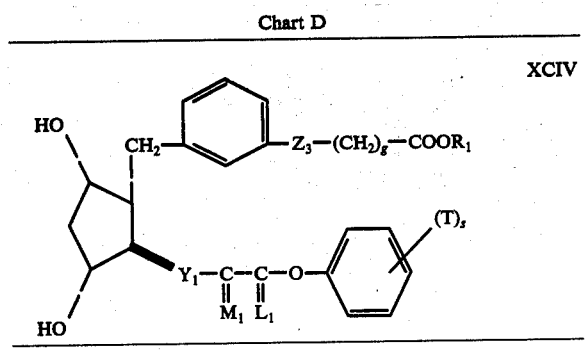
XCIV
Chart E
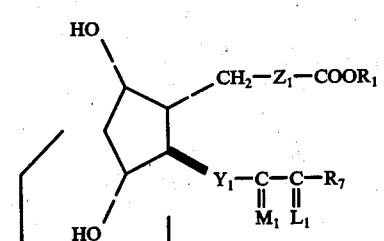
CI
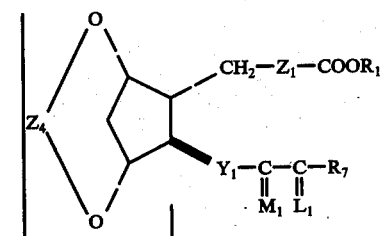
CII
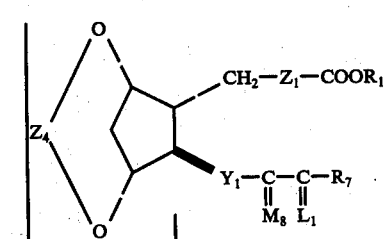
CIII
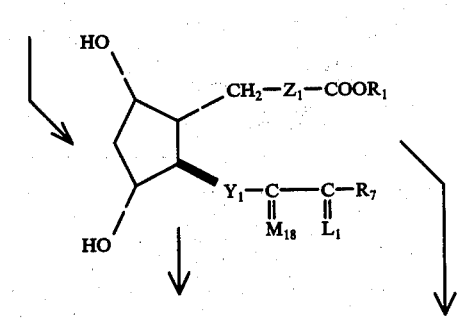
CIV
34
-continued
Chart E
CV
CVI
CVII
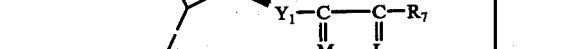
CVIII
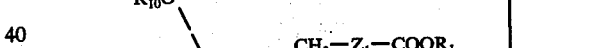
CIX
CX

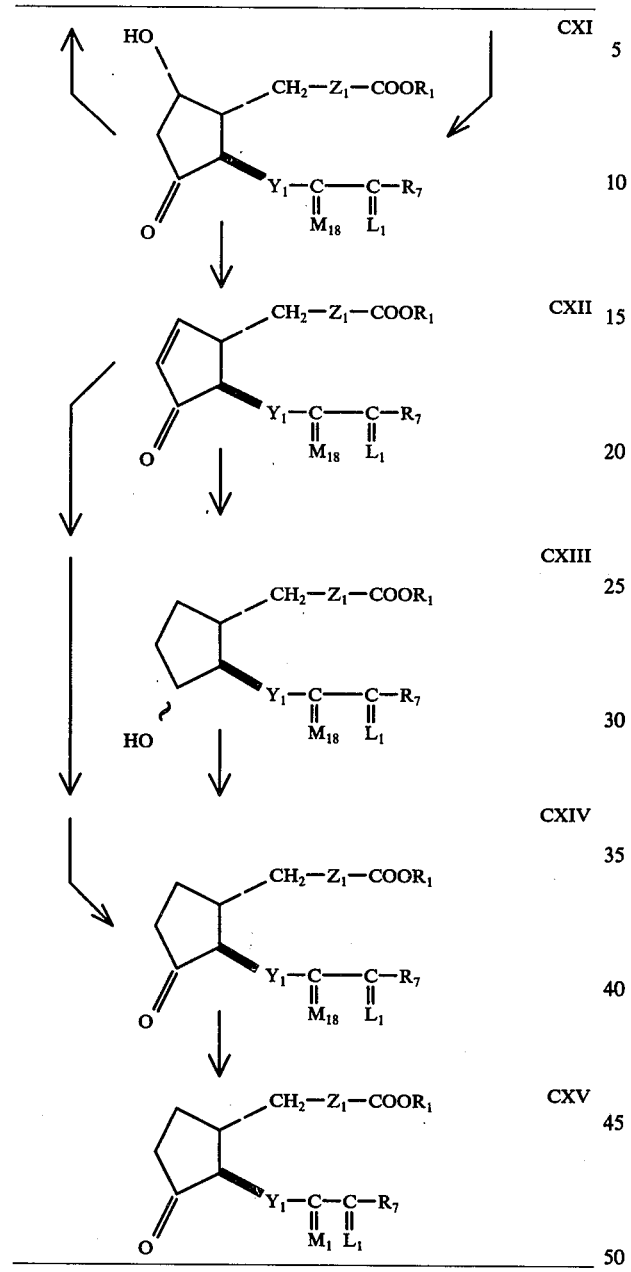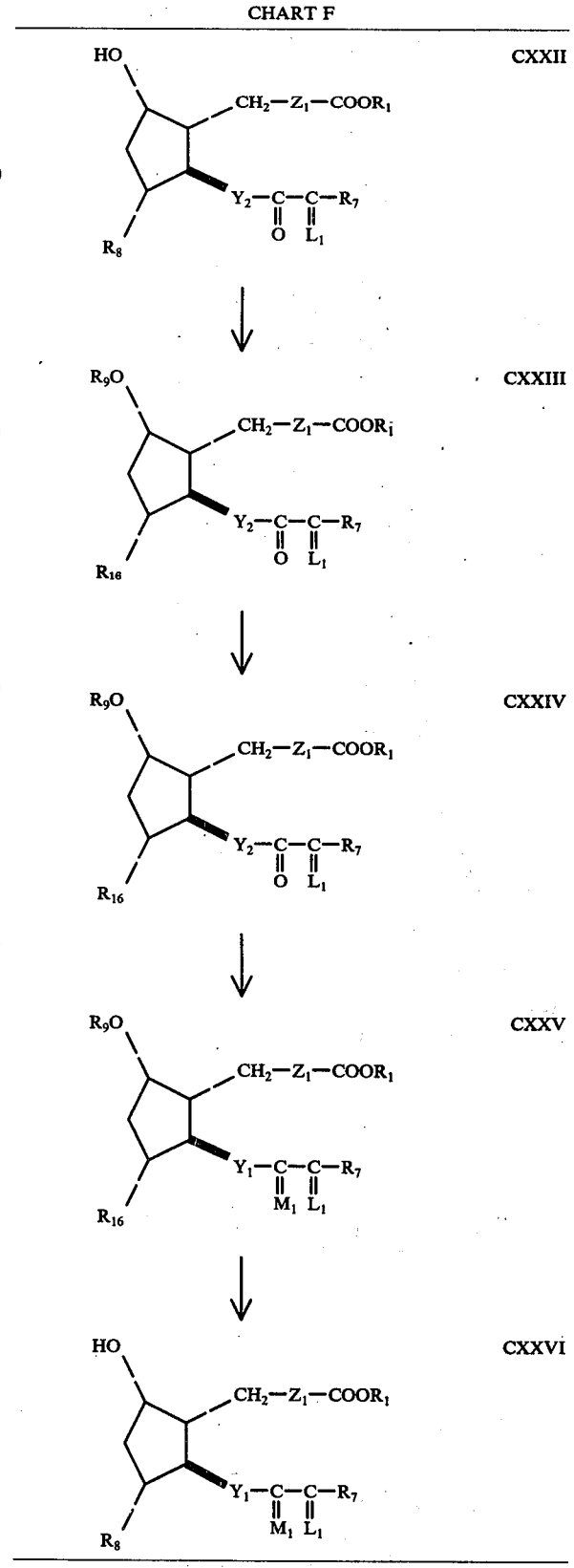

CHART G
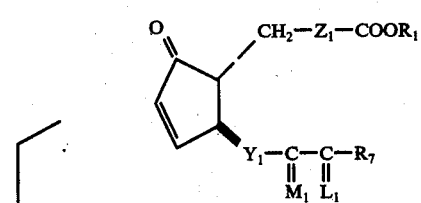 CXLI
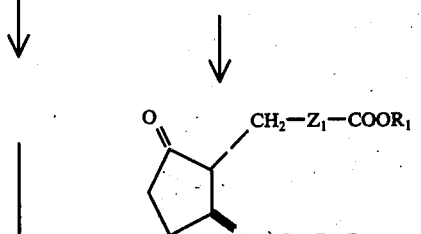 CXLII
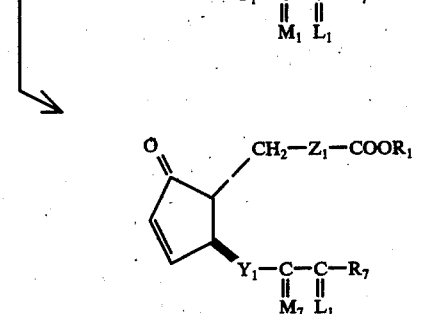 CXLIII
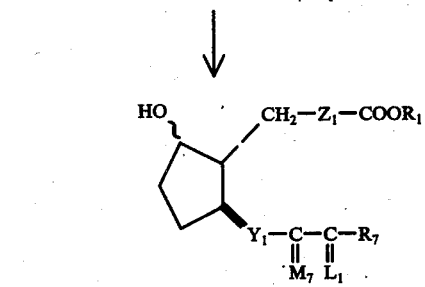 CXLIV
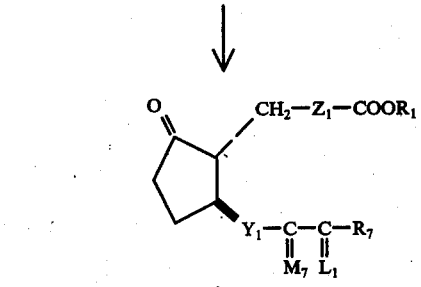 CXLV
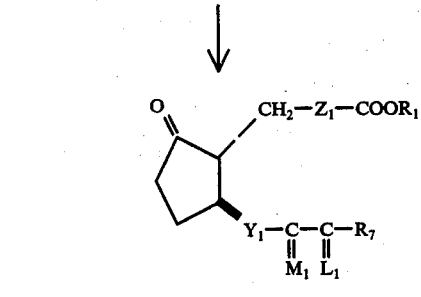 CXLVI
CHART H
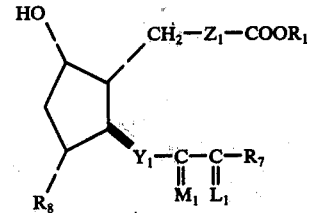 CLI
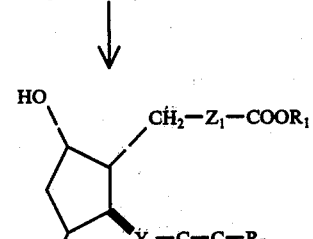 CLII
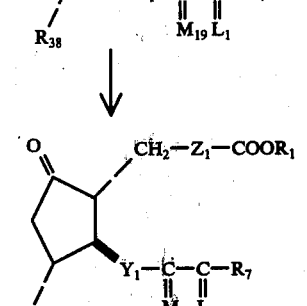 CLIII
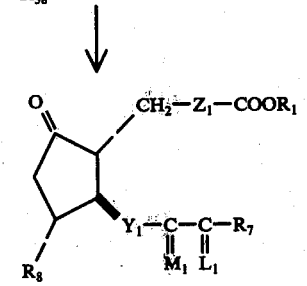 CLIV
CHART J
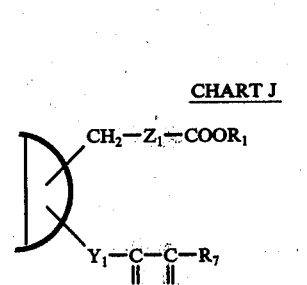 CLXI
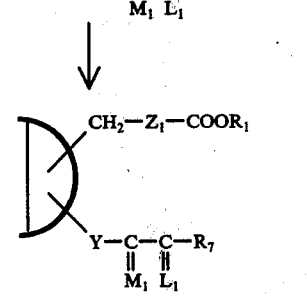 CLXII

CHART K
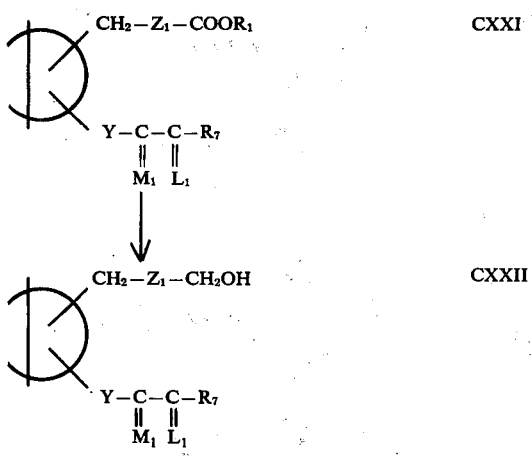
CXXI
CXXII
CHART L
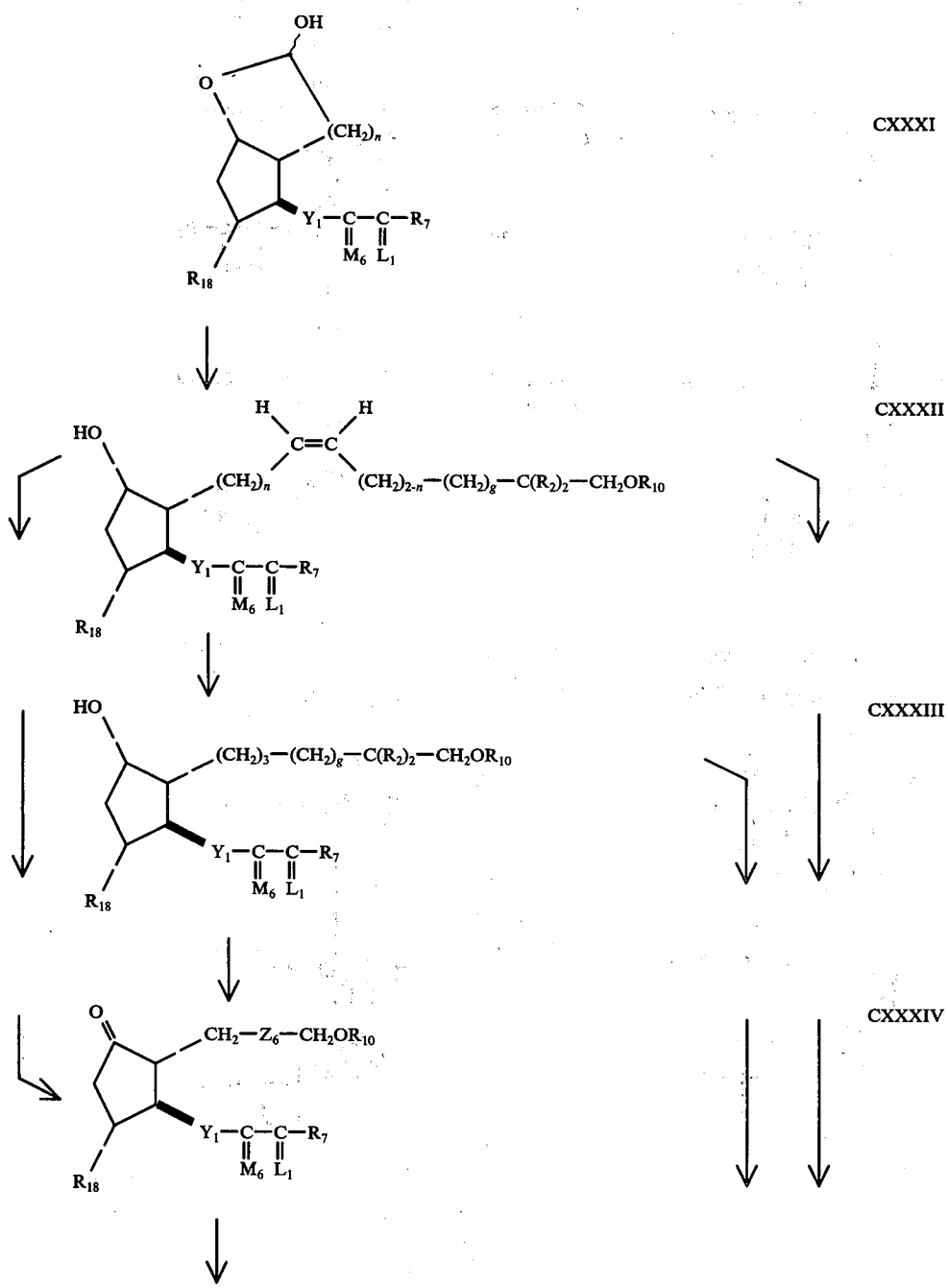
CXXXI
CXXXII
CXXXIII
CXXXIV -continued
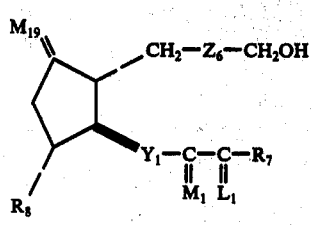
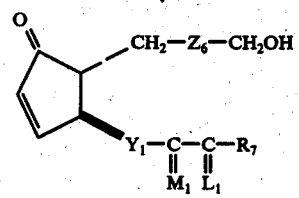
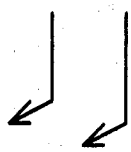 CXXXV
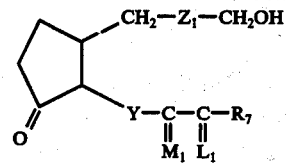 CXXXVI
Chart M
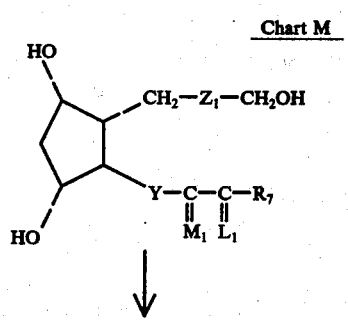
CXXXVII 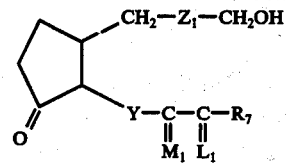
With respect to the Charts $R_2$, $R_7$, $R_8$, $M_1$, $L_1$, Y, $Z_1$, $Z_3$, and g are as defined above. $\mathbb{D}$ is as defined above. The symbol n is one or two. $M_5$ is
CXXXVIII
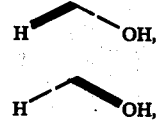
or a mixture of
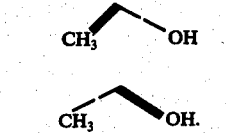
and
CXXXIX
$M_6$ is
or
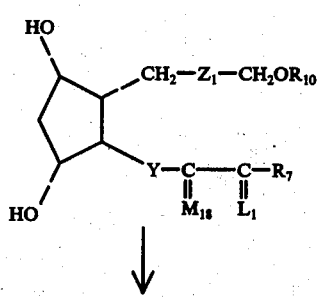
or the mixture of epimers thereof wherein $R_{10}$ is a blocking group and $R_5$ is as defined above. $M_7$ is
CXL
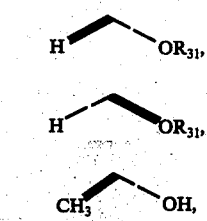
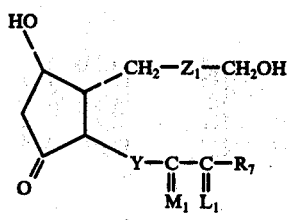
or
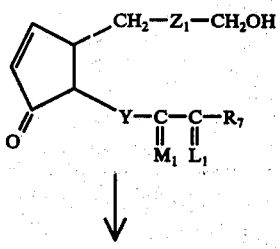

-continued

wherein $R_{31}$ is a blocking group as defined herein below.
$M_8$ is

or

wherein $R_{10}$ is a blocking group. $M_9$ is

or

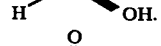

$M_{19}$ is

$M_{18}$ is

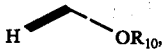

or

wherein $R_{10}$ is a blocking group. $R_{18}$ is hydrogen or —$OR_9$, wherein $R_9$ is an acyl protecting group. $R_{18}$ is hydrogen or —$OR_{10}$, wherein $R_{10}$ is a blocking group. $R_{26}$ is hydrocarbyl, including alkyl aralkyl, cycloalkyl, and the like. Examples of these hydrocarbyl groups include 2-methylbutyl, isopentyl, heptyl, octyl, nonyl, tridecyl, octadecyl, benzyl, phenethyl, p-methylphenethyl, 1-methyl-3-phenylpropyl, cyclohexyl, phenyl, and p-methylphenyl.

$G_1$ is alkyl of one to 4 carbon atoms, aralkyl of 7 to 12 carbon atoms, phenyl, or phenyl substituted with one or 2 fluoro, chloro, or alkyl of one to 4 carbon atoms, with the proviso that in the —Si—$(G_1)_3$ moiety the various $G_1$'s are the same or different. Preferably one of $G_1$ is tert-butyl; and the remaining 2 are methyl.

$R_1$ is hydrogen, alkyl, cycloalkyl, aralkyl, or phenyl.

$Y_1$ is trans-CH═C(Hal)—, wherein Hal is chloro, bromo, or iodo, being preferably chloro. $Y_2$ is trans-CH═CH—.

$R_9$ is an acyl protecting group. Acyl protecting groups according to $R_9$, include:

a. benzoyl;
b. benzoyl substituted with one to 5 alkyl of oneto 4 carbon atoms, inclusive, phenylalkyl of 7 to 12 carbon atoms, inclusive, or nitro, with the proviso that not more than 2 substituents are other than alkyl, and that the total number of carbon atoms in the substituents does not exceed 10 carbon atoms, with the further proviso that the substituents are the same or different;
c. benzoyl substituted with alkoxycarbonyl of 2 to 5 carbon atoms, inclusive;
d. naphthoyl;
e. naphthoyl substituted with one to 9, inclusive, alkyl of one to 4 carbon atoms, inclusive, phenylalkyl of 7 to 10 carbon atoms, inclusive, or nitro, with the proviso that not more than 2 substituents on either of the fused aromatic rings are other than alkyl and that the total number of carbon atoms in the substituents on either of the fused aromatic rings does not exceed 10 carbon atoms, with the further proviso that the various substituents are the same or different; or
f. alkanoyl of 2 to 12 carbon atoms, inclusive.

In preparing these acyl derivatives of a hydroxy-containing containing compound herein, methods generally known in the art are employed. Thus, for example, an aromatic acid of the formula $R_9OH$, wherein $R_9$ is as defined above (e.g., benzoic acid), is reacted with the hydroxy-containing compound in the presence of a dehydrating agent, e.g. sulfuric acid, zinc chloride, or p-toluenesulfonic acid; or alternatively an anhydride of the aromatic acid or the formula $(R_9)_2O$ (e.g., benzoic anhydride) is used.

Preferably, however, the process described in the above paragraph proceeds by use of the appropriate acyl halide, e.g., $R_9Hal$, wherein Hal is chloro, bromo, or iodo. For example, benzoyl chloride is reacted with the hydroxyl-containing compound in the presence of a hydrogen chloride scavenger, e.g. a tertiary amine such as pyridine, triethylamine or the like. The reaction is carried out under a variety of conditions, using procedures generally known in the art. Generally mild conditions are employed: 0°-60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_9$, the following compounds are available as acids ($R_9OH$), anhydrides (($R_9)_2O$), or acyl chlorides ($R_3Cl$): benzoyl; substituted benzoyl, e.g., 2-, 3-, or 4-)-methylbenzoyl, (2-, 3-, or 4-)-ethyl benzoyl, (2-, 3-, or 4-)-isopropylbenzoyl, (2-, 3-, or 4-)-tert-butylbenzoyl, 2,4-dimethylbenzoyl, 3,5-dimethylbenzoyl, 2-isopropyltoluyl, 2,4,6-trimethylbenzoyl, pentamethylbenzoyl, alphaphenyl-(2-, 3-, or 4-)-toluyl, (2-, 3-, or 4-)-phenethylbenzoyl, (2-, 3-, or 4-)-nitrobenzoyl, (2,4-, 2,5-, or 2,3-)dinitrobenzoyl, 2,3-dimethyl-2-nitrobenzoyl, 4,5-dimethyl-2-nitrobenzoyl, 2-nitro-6-phenethylbenzoyl, 3-nitro-2-phenethylbenzoyl, 2-nitro-6-phenethylbenzoyl, 3-nitro-2-phenethylbenzoyl; mono esterified phthaloyl, isophthaloyl, or terephthaloyl; 1- or 2- naphthoyl; substituted naphthoyl, e.g., (2-, 3-, 4-, 5-, 6-, or 7-)-methyl-1-naphthoyl, (2- or 4-) ethyl-1-naphthoyl, 2-isopropyl-1-naphthoyl, 4,5-dimethyl-1 naphthoyl, 6-isopropyl-4-methyl-1-naphthoyl, 8-benzyl-1naphthoyl, (3-, 4-, 5-, or 8-)-nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl.

There may be employed, therefore, benzoyl chloride, 4-nitrobenzoyl chloride, 3,5-dinitrobenzoyl chloride, or the like, i.e. $R_9Cl$ compounds corresponding to the above $R_9$ groups. If the acyl chloride is not available, it is prepared from the corresponding acid and phosphorus pentachloride as is known in the art. It is preferred that the ($R_9OH$, ($R_9)_2O$, or $R_9Cl$ reactant does not have For example, when $R_3$ and $R_4$ of the $L_1$ moiety are both hydrogen there are available butyric, pentanoic, hexanoic, heptanoic, and octanoic acids.

For example, when one and only one of $R_3$ and $R_4$ of the $L_1$ moiety is methyl, there are available 2-methyl alkanoic acids derived from: butyric, pentanoic, hexanoic, heptanoic, and octanoic acids.

For example, when both $R_3$ and $R_4$ of the $L_1$ moiety is fluoro there are available 2,2-difluoro alkanoic acids derived from: butyric, pentanoic, hexanoic, heptanoic, and octanoic acids.

The acids of the above general formula wherein $R_7$ is alkyl and $R_3$ and $R_4$ of the $L_1$ moiety are fluoro are conveniently prepared from the corresponding 2-oxo-alkanoic acids corresponding to butyric, pentanoic, hexanoic, heptanoic, and octanoic acids. The transformation of these 2-oxo-alkanoic acids to the corresponding 2,2-difluoro alkanoic acids proceeds by methods known in the art, using known ketonic fluorinating reagents. For example, $MF_6.BF_3$ is advantageously employed in the fluorination. See Mathey et al., Tetrahedron Letters 27, 2965 (1971).

The formula XXIII compound is prepared from the formula XXII 3-oxo bicyclic lactone by first halogenating and thereafter transforming the 3-oxo-moiety of the 2-halo compound so formed.

The 2-halo compound is prepared from the formula XXII compound by dihalogenation, followed by dehydrohalogenation. The halogenation proceeds by methods known in the art, conveniently by reaction of the formula XXII compound with a reagent such as N-halosuccinimide. The reaction proceeds slowly to completion, ordinarily within three to ten days. Alternatively the molelcular form of the halide (Hal)$_2$ in a diluent (e.g., carbon tetrachloride or a mixture of acetic acid and sodium acetate) is employed in this dihalogenation. Thereafter dehydrohalogenation proceeds by addition of an organic base, preferably amine base, to the halide. For example pyridine, or a diazobicycloalkene, is an especially useful amine base, although non-amine bases such as methanolic sodium acetate are likewise employed.

In any event, the 2-chloro intermediates are preferred 2-halo products, in that they lead to PG intermediates which are more easily dehydrohalogenated at C-13 and C-14 according to the procedure described hereinafter.

Optionally the 2-halo compound is prepared directly from the formula XXI compound using a Wittig reagent derived from a 1-halophosphonate corresponding to the phosphonate described above for the preparation of the formula XXII compound. These phosphonates are known in the art or are readily prepared by methods known in the art. For example, a phosphonate as described above is transformed to the corresponding 1-halophosphonate by dripping the molecular halogen into a solution of the phosphonate and a strong organic base, e.g. sodium methoxide.

The 1-halophosphonate as prepared above is then reacted with the formula XXI compound in a manner described for the preparation of the formula XXII compound from the formula XXI compound to prepare the 2-halo compound.

In each of the above described methods for the preparation of the 2-halo compound the desired 2-halo product is often contaminated with its corresponding cis isomer. In performing the below steps it is particularly desirable to obtain pure trans-2-halo-product in order to avoid creation of complicated mixtures of steroisomers. Accordingly, the 2-halo compound is subjected to conventional separation techniques (e.g. silica gel chromatography) to obtain pure product.

The formula XXIV compound is prepared from the formula XXIII 3-oxo bicyclic lactone by transformation of the 3-oxomoiety to the $M_5$ moiety.

The above 2-halo compound is transformed to the corresponding 3α- or 3β-hydroxy bicyclic lactone, wherein $M_5$ is

by reduction of the 3-oxo moiety, followed by separation of the 3α- and 3β-hydroxy epimers. For this reduction the known ketonic carbonyl reducing agents which do not reduce ester or acid groups or carbon-carbon double bonds (when such reduction is undesirable) are employed. Examples of these agents are the metal borohydrides, especially sodium, potassium, and zinc borohydrides, lithium (tri-tert-butoxy)aluminum hydride, metal trialkyl borohydrides, e.g. sodium trimethoxy borohydride, lithium borohydide, and the like. In those cases in which carbon-carbon double bond reduction need not be avoided, the boranes, e.g. disiamylborane (bis3-methyl-2-butyl borane) are alternatively employed.

For the production of C-15 epimerically pure prostaglandins, the 15-epi compound is separated from the mixture by methods known in the art. For example, silica gel chromatography is advantageously employed.

The 2-halo compound is transformed into the corresponding (3RS)-3-methyl bicyclic lactone wherein $M_5$ is a mixture of

by reaction of the 2-halo compound with a Grignard reagent, $CH_3MgHal$, wherein Hal is chloro, bromo, or iodo. The Grignard complex is thereafter hydrolyzed, for example, using saturated aqueous ammonium chloride as is known in the art. An alternate method for transforming the 2-halo compound to a 3(RS)-3-methyl compound is by reaction of the 3-oxo bicyclic lactone with trimethylaluminum.

The preferred method for separation of these (3RS)-3-methyl epimers is by separation of the corresponding C-15 epimers of the PG-type, methyl esters using silica gel chromatography or high pressure liquid chromatography (HPLC).

The formula XXIV compound is prepared from the formula XXIII compound by deacylation, as described above. The formula XXV compound is then prepared from the formula XXIV compound by replacing any free hydroxy moieties with blocking groups according to $R_{10}$ by the procedure described above. The formula XXVI compound is then prepared from the formula XXV compound by reduction of the formula XXV lactone to a lactol. Methods known in the art are employed. For example, diisobutylaluminum hydride is employed at −60° to −80° C.

The formula XXVI compound undergoes condensation to form the formula XXVII enol ether. For this purpose a hydrocarbyloxy, and preferably an alkoxymethylenetriphenylphosphorane is useful. See for refernce, Levine, Journal of the American Chemical Society 80, 6150 (1958). The reagent is conveniently prepared from a corresponding quaternary phosphonium halide in a base, e.g. butyllithium or phenyllithium, at low temperature, e.g. preferably below −10° C. The formula XXVI lactol is mixed with the above reagent and the condensation proceeds smoothly within the temperature range of −30° C. - +30° C. At higher temperatures the reagent is unstable, whereas at low temperatures the rate of condensation is undesirably slow. Examples of alkoxymethylenetriphenylphosphoranes preferred for the above purposes are methoxy-, ethoxy-, propoxy-, isopropoxy-, butoxy-, isobutoxy-, s-butoxy-, and t-butoxy- methylenetriphenylphosphorane. Various hydrocarbyloxymethylenetriphenylphosphoranes which are optionally substituted for the alkoxymethylenetriphenylphosphoranes and are accordingly useful for preparing the formula XXVII intermediates wherein $R_{26}$ is hydrocarbyl, include alkoxy-, aralkoxy-, cycloalkoxy-, and aryloxymethylenetriphenylphosphoranes. Examples of these hydrocarbyloxytriphenylphosphoranes are 2-methyl butyloxy-, isopentyloxy-, heptyloxy-, octyloxy-, nonyloxy-, tridecyloxy-, octadecyloxy-, benzyloxy-, phenethyloxy-, p-methylphenethyloxy-, 1-methyl-3-phenylpropyloxy-, cyclohexyloxy-, phenoxy-, and p-methylphenoxy-, phenoxymethylenetriphenylphosphorane. See for reference, Organic Reactions, Vol. 14, pg. 346–348, John Wiley and Sons, New York, New York, (1965). The formula XXVII enol intermediates are then hydrolyzed to the formula XXVIII lactols. This hydrolysis is done under acidic conditions for example with perchloric acid or acetic acid. Tetrahydrofuran is a suitable diluent for this reaction mixture. Reaction temperatures of from 10° to 100° C. are employed. The length of time required for hydrolysis is determined in part by the hydrolysis temperature and using acetic acid-water-tetrahydrofuran at about 60° C. several hr. are sufficient to accomplish the hydrolysis.

The formula XXIX compound is then prepared from the formula XXVIII compound by oxidation of the formula XXVIII lactol to a lactone. This transformation is carried out, using for example, silver oxide as an oxidizing reagent, followed by treatment with pyridine hydrochloride and by transformation of any free hydroxy moieties to blocking groups, according to $R_{10}$, following the procedures herein described for these transformations to obtain XXX.

Thereafter the formula XXXI compound or formula XXXII compound (wherein $n$ is 2) is prepared from the formula XXX compound by reduction of the formula XXX lactone to a lactol. For example, diisobutylaluminum hydride is employed as is described above for the reduction of lactones to lactols. The formula XXVI lactols are alternately represented by the formula XXXII compound when n is one.

The formula XXXIII compound is prepared from the formula XXXII compound by a Wittig alkylation, using the appropriate (ω-carboxyalkyl)triphenylphosphonium bromide. The reaction proceeds as is generally known in the art, by first mixing the appropriate (ω-carboxyalkyl)-triphenylphosphonium bromide with sodio dimethyl sulfinylcarbanide, at ambient temperature, and adding the formula XXXII lactol to this mixture. Thereafter the carboxy hydrogen of the compound so formed is transformed to an $R_1$ moiety by the methods and procedures hereinbelow described. Accordingly, there is prepared the formula XXXIII cis-4,5-didehydro-14-halo-11-deoxy-$PGF_{1\alpha}$-, 14-halo-11-deoxy-$PGF_{2\alpha}$-, cis-4,5-dide-hydro-14-halo-$PGF_{1\alpha}$-, or 14-halo-$PGF_{2\alpha}$-type intermediate.

The formula XXXIV compound is then prepared from the formula XXXIII compound by catalytic hydrogenation of the formula XXXIII compound. Methods known in the art for transformation of $PG_2$-type compounds to $PG_1$-type compounds are employed. Accordingly, metal catalysts (e.g. palladium) on a suitable support (e.g. carbon) at about 0° C. are employed under a hydrogen atmosphere. See for reference B. Samuelsson, Journal of Biological Chemistry, 239, 491 (1974).

The formula XXXII lactol is transformed into the corresponding formula XXXVI 5-oxa-14-halo-$PGF_{1\alpha}$-type intermediate first by reduction of the formula XXXII lactol, for example, with aqueous methanolic or ethanolic sodium borohydride to the formula XXXV compound. Alternatively, and preferably, the formula XXXV compound is obtained by a one step reduction of the formula XXV lactone, for example, with lithium aluminum hydride or diisobutyl aluminum hydride at a temperature ranging from 0° to 35° C. For preparing the formula XXXVI compound, a Williamson synthesis is employed. For example, the formula XXXV compound is condensed with a haloalkanoate within the scope of

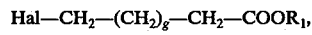

wherein Hal is chloro, bromo, or iodo and $g$ is as defined above. Normally the reaction is done in the presence of a base such as n-butyllithium, phenyllithium, trimethyllithium, sodium hydride, or potassium t-butoxide.

Alternatively and preferably, an ortho-4-bromoalkanoate is employed. Such reagents are available or are prepared by methods known in the art, for example, from the appropriate halonitrile by way of the corresponding imino ester hydrohalide as illustrated hereinafter.

The condensation is conveniently run in a solvent, such as tetrahydrofuran or dimethyl sulfoxide or especially if an organolithium compound is employed, preferably in dimethylformamide or hexamethylphosphoramide. The reaction proceeds smoothly at −20° to 50° C., but is preferably performed at ambient temperature. Following the condensation by formula XXXVI compound is obtained by methods known in the art, for example, by hydrolysis in cold dilute mineral acid.

Thereafter, the formula XXXVII compound is prepared from the formula XXXIII, XXXIV, or XXXVI compound by oxidation of the 9-hydroxy to a 9-oxo. Oxidation methods known in the art for the transformation of PGF-type compounds to corresponding PGE-type compounds are employed. For example, the Jones reagent or the Collins reagent is advantageously used.

Thereafter the formula XXXVIII compound is prepared from the formula XXXVII compound by a ring carbonyl reduction. These ring carbonyl reductions are carried out by methods known in the art for ring carbonyl reductions of known prostanoic acid derivatives. See for example, Bergstrom, et al., Arkiv. Kemi. 19,563

For example, when R₃ and R₄ of the L₁ moiety are both hydrogen there are available butyric, pentanoic, hexanoic, heptanoic, and octanoic acids.

For example, when one and only one of R₃ and R₄ of the L₁ moiety is methyl, there are available 2-methyl alkanoic acids derived from: butyric, pentanoic, hexanoic, heptanoic, and octanoic acids.

For example, when both R₃ and R₄ of the L₁ moiety is fluoro there are available 2,2-difluoro alkanoic acids derived from: butyric, pentanoic, hexanoic, heptanoic, and octanoic acids.

The acids of the above general formula wherein R₇ is alkyl and R₃ and R₄ of the L₁ moiety are fluoro are conveniently prepared from the corresponding 2-oxo-alkanoic acids corresponding to butyric, pentanoic, hexanoic, heptanoic, and octanoic acids. The transformation of these 2-oxo-alkanoic acids to the corresponding 2,2-difluoro alkanoic acids proceeds by methods known in the art, using known ketonic fluorinating reagents. For example, MF₆·BF₃ is advantageously employed in the fluorination. See Mathey et al., Tetrahedron Letters 27, 2965 (1971).

The formula XXIII compound is prepared from the formula XXII 3-oxo bicyclic lactone by first halogenating and thereafter transforming the 3-oxo-moiety of the 2-halo compound so formed.

The 2-halo compound is prepared from the formula XXII compound by dihalogenation, followed by dehydrohalogenation. The halogenation proceeds by methods known in the art, conveniently by reaction of the formula XXII compound with a reagent such as N-halosuccinimide. The reaction proceeds slowly to completion, ordinarily within three to ten days. Alternatively the molelcular form of the halide (Hal)₂ in a diluent (e.g., carbon tetrachloride or a mixture of acetic acid and sodium acetate) is employed in this dihalogenation. Thereafter dehydrohalogenation proceeds by addition of an organic base, preferably amine base, to the halide. For example pyridine, or a diazobicycloalkene, is an especially useful amine base, although non-amine bases such as methanolic sodium acetate are likewise employed.

In any event, the 2-chloro intermediates are preferred 2-halo products, in that they lead to PG intermediates which are more easily dehydrohalogenated at C-13 and C-14 according to the procedure described hereinafter.

Optionally the 2-halo compound is prepared directly from the formula XXI compound using a Wittig reagent derived from a 1-halophosphonate corresponding to the phosphonate described above for the preparation of the formula XXII compound. These phosphonates are known in the art or are readily prepared by methods known in the art. For example, a phosphonate as described above is transformed to the corresponding 1-halophosphonate by dripping the molecular halogen into a solution of the phosphonate and a strong organic base, e.g. sodium methoxide.

The 1-halophosphonate as prepared above is then reacted with the formula XXI compound in a manner described for the preparation of the formula XXII compound from the formula XXI compound to prepare the 2-halo compound.

In each of the above described methods for the preparation of the 2-halo compound the desired 2-halo product is often contaminated with its corresponding cis isomer. In performing the below steps it is particularly desirable to obtain pure trans-2-halo-product in order to avoid creation of complicated mixtures of steroisomers.

Accordingly, the 2-halo compound is subjected to conventional separation techniques (e.g. silica gel chromatography) to obtain pure product.

The formula XXIV compound is prepared from the formula XXIII 3-oxo bicyclic lactone by transformation of the 3-oxomoiety to the M₅ moiety.

The above 2 -halo compound is transformed to the corresponding 3α- or 3β-hydroxy bicyclic lactone, wherein M₅ is

or by reduction of the 3-oxo moiety, followed by separation of the 3α- and 3β-hydroxy epimers. For this reduction the known ketonic carbonyl reducing agents which do not reduce ester or acid groups or carbon-carbon double bonds (when such reduction is undesirable) are employed. Examples of these agents are the metal borohydrides, especially sodium, potassium, and zinc borohydrides, lithium (tri-tert-butoxy)aluminum hydride, metal trialkyl borohydrides, e.g. sodium trimethoxy borohydride, lithium borohydide, and the like. In those cases in which carbon-carbon double bond reduction need not be avoided, the boranes, e.g. disiamylborane (bis3-methyl-2-butyl borane) are alternatively employed.

For the production of C-15 epimerically pure prostaglandins, the 15-epi compound is separated from the mixture by methods known in the art. For example, silica gel chromatography is advantageously employed.

The 2-halo compound is transformed into the corresponding (3RS)-3-methyl bicyclic lactone wherein M₅ is a mixture of

by reaction of the 2-halo compound with a Grignard reagent, CH₃MgHal, wherein Hal is chloro, bromo, or iodo. The Grignard complex is thereafter hydrolyzed, for example, using saturated aqueous ammonium chloride as is known in the art. An alternate method for transforming the 2-halo compound to a 3(RS)-3-methyl compound is by reaction of the 3-oxo bicyclic lactone with trimethylaluminum.

The preferred method for separation of these (3RS)-3-methyl epimers is by separation of the corresponding C-15 epimers of the PG-type, methyl esters using silica gel chromatography or high pressure liquid chromatography (HPLC).

The formula XXIV compound is prepared from the formula XXIII compound by deacylation, as described above. The formula XXV compound is then prepared from the formula XXIV compound by replacing any free hydroxy moieties with blocking groups according to R₁₀ by the procedure described above. The formula XXVI compound is then prepared from the formula XXV compound by reduction of the formula XXV lactone to a lactol. Methods known in the art are employed. For example, diisobutylaluminum hydride is employed at −60° to −80° C.

The formula XXVI compound undergoes condensation to form the formula XXVII enol ether. For this purpose a hydrocarbyloxy, and preferably an alkoxymethylenetriphenylphosphorane is useful. See for refernce, Levine, Journal of the American Chemical Society 80, 6150 (1958). The reagent is conveniently prepared from a corresponding quaternary phosphonium halide in a base, e.g. butyllithium or phenyllithium, at low temperature, e.g. preferably below −10° C. The formula XXVI lactol is mixed with the above reagent and the condensation proceeds smoothly within the temperature range of −30° C. - +30° C. At higher temperatures the reagent is unstable, whereas at low temperatures the rate of condensation is undesirably slow. Examples of alkoxymethylenetriphenylphosphoranes preferred for the above purposes are methoxy-, ethoxy-, propoxy-, isopropoxy-, butoxy-, isobutoxy-, s-butoxy-, and t-butoxy- methylenetriphenylphosphorane. Various hydrocarbyloxymethylenetriphenylphosphoranes which are optionally substituted for the alkoxymethylenetriphenylphosphoranes and are accordingly useful for preparing the formula XXVII intermediates wherein $R_{26}$ is hydrocarbyl, include alkoxy-, aralkoxy-, cycloalkoxy-, and aryloxymethylenetriphenylphosphoranes. Examples of these hydrocarbyloxytriphenylphosphoranes are 2-methyl butyloxy-, isopentyloxy-, heptyloxy-, octyloxy-, nonyloxy-, tridecyloxy-, octadecyloxy-, benzyloxy-, phenethyloxy-, p-methylphenethyloxy-, 1-methyl-3-phenylpropyloxy-, cyclohexyloxy-, phenoxy-, and p-methylphenoxy-, phenoxymethylenetriphenylphosphorane. See for reference, Organic Reactions, Vol. 14, pg. 346–348, John Wiley and Sons, New York, New York, (1965). The formula XXVII enol intermediates are then hydrolyzed to the formula XXVIII lactols. This hydrolysis is done under acidic conditions for example with perchloric acid or acetic acid. Tetrahydrofuran is a suitable diluent for this reaction mixture. Reaction temperatures of from 10° to 100° C. are employed. The length of time required for hydrolysis is determined in part by the hydrolysis temperature and using acetic acid-water-tetrahydrofuran at about 60° C. several hr. are sufficient to accomplish the hydrolysis.

The formula XXIX compound is then prepared from the formula XXVIII compound by oxidation of the formula XXVIII lactol to a lactone. This transformation is carried out, using for example, silver oxide as an oxidizing reagent, followed by treatment with pyridine hydrochloride and by transformation of any free hydroxy moieties to blocking groups, according to $R_{10}$, following the procedures herein described for these transformations to obtain XXX.

Thereafter the formula XXXI compound or formula XXXII compound (wherein n is 2) is prepared from the formula XXX compound by reduction of the formula XXX lactone to a lactol. For example, diisobutylaluminum hydride is employed as is described above for the reduction of lactones to lactols. The formula XXVI lactols are alternately represented by the formula XXXII compound when n is one.

The formula XXXIII compound is prepared from the formula XXXII compound by a Wittig alkylation, using the appropriate (ω-carboxyalkyl)triphenylphosphonium bromide. The reaction proceeds as is generally known in the art, by first mixing the appropriate (ω-carboxyalkyl)-triphenylphosphonium bromide with sodio dimethyl sulfinylcarbanide, at ambient temperature, and adding the formula XXXII lactol to this mixture. Thereafter the carboxy hydrogen of the compound so formed is transformed to an $R_1$ moiety by the methods and procedures hereinbelow described. Accordingly, there is prepared the formula XXXIII cis-4,5-didehydro-14-halo-11-deoxy-PGF$_{1\alpha}$-, 14-halo-11-deoxy-PGF$_{2\alpha}$-, cis-4,5-dide-hydro-14-halo-PGF$_{1\alpha}$-, or 14-halo-PGF$_{2\alpha}$-type intermediate.

The formula XXXIV compound is then prepared from the formula XXXIII compound by catalytic hydrogenation of the formula XXXIII compound. Methods known in the art for transformation of PG$_2$-type compounds to PG$_1$-type compounds are employed. Accordingly, metal catalysts (e.g. palladium) on a suitable support (e.g. carbon) at about 0° C. are employed under a hydrogen atmosphere. See for reference B. Samuelsson, Journal of Biological Chemistry, 239, 491 (1974).

The formula XXXII lactol is transformed into the corresponding formula XXXVI 5-oxa-14-halo-PGF$_{1\alpha}$-type intermediate first by reduction of the formula XXXII lactol, for example, with aqueous methanolic or ethanolic sodium borohydride to the formula XXXV compound. Alternatively, and preferably, the formula XXXV compound is obtained by a one step reduction of the formula XXV lactone, for example, with lithium aluminum hydride or diisobutyl aluminum hydride at a temperature ranging from 0° to 35° C. For preparing the formula XXXVI compound, a Williamson synthesis is employed. For example, the formula XXXV compound is condensed with a haloalkanoate within the scope of

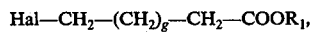

Hal—CH$_2$—(CH$_2$)$_g$—CH$_2$—COOR$_1$, wherein Hal is chloro, bromo, or iodo and g is as defined above. Normally the reaction is done in the presence of a base such as n-butyllithium, phenyllithium, trimethyllithium, sodium hydride, or potassium t-butoxide.

Alternatively and preferably, an ortho-4-bromoalkanoate is employed. Such reagents are available or are prepared by methods known in the art, for example, from the appropriate halonitrile by way of the corresponding imino ester hydrohalide as illustrated hereinafter.

The condensation is conveniently run in a solvent, such as tetrahydrofuran or dimethyl sulfoxide or especially if an organolithium compound is employed, preferably in dimethylformamide or hexamethylphosphoramide. The reaction proceeds smoothly at −20° to 50° C., but is preferably performed at ambient temperature. Following the condensation by formula XXXVI compound is obtained by methods known in the art, for example, by hydrolysis in cold dilute mineral acid.

Thereafter, the formula XXXVII compound is prepared from the formula XXXIII, XXXIV, or XXXVI compound by oxidation of the 9-hydroxy to a 9-oxo. Oxidation methods known in the art for the transformation of PGF-type compounds to corresponding PGE-type compounds are employed. For example, the Jones reagent or the Collins reagent is advantageously used.

Thereafter the formula XXXVIII compound is prepared from the formula XXXVII compound by a ring carbonyl reduction. These ring carbonyl reductions are carried out by methods known in the art for ring carbonyl reductions of known prostanoic acid derivatives. See for example, Bergstrom, et al., Arkiv. Kemi. 19,563

(1963), Acta, Chem. Scand. 16, 969 (1962), and British Specification No. 1,097,533. Any reducing agent is used which does not react with carbon-carbon double bonds or ester groups, for example, lithium (tri-tert-butoxy) aluminum hydride, the metal borohydrides (especially sodium, potassium, and zinc borohydride) and the metal trialkoxy borohydrides (e.g. sodiumtrimethoxy borohydride) are employed. The $PGF_\beta$-type intermediate is then separated from the mixture of alpha and beta hydroxy reduction products so prepared by methods known in the art for separation of analogous pairs of known isomeric prostanoic acid derivatives. See, for example, Bergstrom, et al. cited above, Granstrom et al., Journal of Biological Chemistry 240, 457 (1965), and Green et al., Journal of Lipid Research 5, 117 (1974). For this purpose silica gel chromatography or high pressure liquid chromatography are employed.

The formula XXXIX compound is then prepared from the formula XXXVIII compound, the formula XXXVII compound, the formula XXXVI compound, the formula XXXIV compound, or the formula XXXIII compound. This preparation proceeds by first separating any mixed C-15 epimers, and thereafter hydrolyzing any blocking groups according to $R_{10}$. Acidic conditions are employed as is described above.

Thereafter the formula XXXIX compound wherein $M_{19}$ is $$\overset{O}{\underset{\|}{\phantom{X}}}$$

and $R_8$ is hydroxy is dehydrated under acidic conditions to form the formula XL compound. Methods known in the art for the transformation of PGE-type compounds to PGA-type compounds are employed. For example acetic acid at ambient temperature is advantageously used.

In the employment of the processes above when C-15 tertiary alcohols are to be prepared ($R_5$ is methyl) the use of blocking groups is not required when preparing 11-deoxy-PG's. In the above charts the introduction and hydrolysis of blocking groups are thereby omitted by the preferred process when 11-deoxy-PG-type compounds are prepared.

Certain (3RS)-3-methyl lactones of Chart A may be separated into their respective (3S)- or (3R)-epimers by silica gel chromatographic separation techniques. Where such separation is possible, this route is preferred. Accordingly, in these cases the separation is effected and $M_5$ is $$CH_3 \diagup \diagdown OH$$

or $$CH_3 \diagup \diagdown OH$$

and $M_6$ is $$CH_3 \diagup \diagdown OR_{10}$$

or $$CH_3 \diagup \diagdown OR_{10}$$

wherein R10 is a blocking group. Accordingly, the separation procedure of PG-type intermediates is omitted when the optional lactone separation is employed.

When a formula XXXIII cis-4,5-didehydro-14-halo-$PGF_{1\alpha}$ or cis-4,5-didehydro-14-halo-11-deoxy-$PGF_{1\alpha}$-type compound is to be prepared by the procedure of Chart A, the Wittig alkylation step XXXII to XXXIII may be performed on the formula XXVIII lactol, instead of the formula XXXII lactol, thereby eliminating the oxidation, etherification, and reduction steps of Chart A (XXIX through XXXI).

Charts B, C, and D provide methods whereby 3-oxa-3,7-inter-m-phenylene-4,5,6-trinor- or 3,7-inter-m-phenylene-4,5,6-trinor-14-halo-PG-type intermediates are prepared. With respect to Charts B and C, $R_7$ is preferred to be $-(CH_2)_m-CH_3$, or $$-CH_2-\underset{\phantom{X}}{\bigcirc}-(T)_s$$

wherein $m$, T, and $s$ are as defined above. In Chart D a method is provided for preparing those novel compounds of this specification wherein $R_7$ is preferably $$-O-\underset{\phantom{X}}{\bigcirc}-(T)_s$$

wherein T and $s$ are as defined above, respectively. Accordingly the Charts B-D provide methods whereby intermediates useful in producing all inter-m-phenylene-PG-type compounds are prepared.

In Chart B both the endo and exo forms of bicyclo hexene LXI are available or are made by methods known in the art, in either their racemic or enantiomerically pure forms. See U.S. Pat. No. 3,711,515. Either the endo or exo starting material will yield the ultimate intermediates of formula LXXIII by the process of Chart B.

Oxetane LXII is obtained by reaction of the formula LXI bicyclo hexene with an aldehyde of the formula $$HC(=O)-\underset{\phantom{X}}{\bigcirc}-OR_{63}$$

wherein $R_{63}$ is carboxyacyl of the formula $$R_{64}\overset{O}{\underset{\|}{C}}-$$

wherein $R_{64}$ is hydrogen, alkyl of one to 19 carbon atoms, inclusive, or aralkyl of 7 to 12 carbon atoms, inclusive, wherein alkyl or aralkyl are substituted with zero to 3 halo atoms.

The above benzaldehydes are available or readily prepared by methods known in the art. Examples of such compounds within this scope are:

$$HC(=O)-\underset{\phantom{X}}{\bigcirc}-OCCH_3(=O)$$

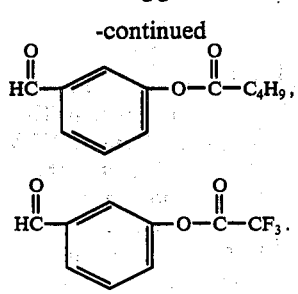

and

The formation of oxetane LXII is accomplished by photolysis of a mixture of the bicyclo hexene and the aldehyde in a solvent. The bicyclo hexene is preferably used in excess over the molar equivalent, for example 2 to 4 times the stoichiometric equivalent amount. The solvent is a photochemically inert organic liquid, for example liquid hydrocarbons, including benzene or hexane, 1,4-dioxane, and diethyl ether. The reaction is conveniently done at ambient conditions, for example 25° C., but may be done over a wide range of temperature, from about −78° C. to the boiling point of the solvent. The irradiation is done with mercury vapor lamps of the low or medium pressure type, for example those peaking at 3500 A. Such sources are available from The Southern New England Ultraviolet Co., Middletown, Conn. Alternatively, those lamps which emit a broad spectrum of wavelengths and which may be filtered to transmit only light of λ ∼ 3000–3700 A may also be used. For a view of photolysis see D. R. Arnold in "Advances in Photochemistry", Vol. 6, W. A. Noyes et al, Wiley-interscience, New York, 1968, pp. 301–423.

The cleavage of the oxetane ring to yield the formula LXIII compound from the formula LXII compound is accomplished with an alkali metal in the presence of a primary amine or an alcohol. Preferred is lithium in ethylamine, or sodium in butyl alcohol. See L. J. Altman et al., Snythesis 129 (1974). The cleavage transformation may also be accomplished by catalytic hydrogenation over an inert metal catalyst, e.g. Pd-on-carbon, in ethyl acetate or ethanol.

The formula LXIV compound is prepared from the formula LXIII diol by preferably blocking the two hydroxyl groups with carboxyacyl groups according to $R_{63}$, i.e.

as defined above. For example, the diol is treated with an acid anhydride such as acetic anhydride, or with an acyl halide in a tertiary amine. Especially preferred is pivaloyl chloride in pyridine.

Other carboxyacylating agents useful for this transformation are known in the art or readily obtainable by methods known in the art, and include carboxyacyl halides, preferably chlorides, bromides, or fluorides, i.e. $R_{64}C(O)Cl$, $R_{64}C(O)Br$, or $R_{64}C(O)F$, and carboxy acid anhydrides, $(R_{64}C-)_2O$, wherein $R_{64}$ is as defined above. The preferred reagent is an acid anhydride. Examples of acid anhydrides useful for this purpose are acetic anhydride, propionic anhydride, butyric anhydride, pentanoic anhydride, nonanoic anhydride, tridecanoic anhydride, steric anhydride, (mono, di, or tri)chloroacetic anhydride, 3-chlorovaleric anhydride, 3-(2-bromoethyl)-4,8-dimethylnonanoic anhydride, cyclopropaneacetic anhydride, 3-cycloheptanepropionic anhydride, 13-cyclopentanetridecanoic anhydride, phenylacetic anhydride, (2 or 3)-phenylpropionic anhydride, 13-phenyltridecanoic anhydride, phenoxyacetic anhydride, benzoic anhydride, (o, m, or p)-bromobenzoic anhydride, 2,4-(or 3,4)-dichlorobenzoic anhydride, p-trifluoromethylbenzoic anhydride, 2-chloro-3-nitrobenzoic anhydride, (o, m, or p)-nitrobenzoic anhydride, (o, m, or p)-toluic anhydride, 4-methyl-3-nitrobenzoic anhydride, 4-octylbenzoic anhydride, (2,3, or 5)-biphenylcarboxylic anhydride, 3-chloro-4-biphenylcarboxylic anhydride, 5-isopropyl-6-nitro-3-biphenylcarboxylic anhydride, and (1 or 2)-napthoic anhydride. The choice of anhydride depends upon the identity of $R_{64}$ in the final acylated product, for example when $R_{64}$ is to be methyl, acetic anhydride is used; when $R_{64}$ is to be 2-chlorobutyl, 3-chlorovaleric anhydride is used.

When $R_{64}$ is hydrogen,

is formyl. Formylation is carried out by procedures known in the art, for example, by reaction of the hydroxy compound with the mixed anhydride of acetic and formic acids or with formylimidazole. See, for example, Fieser et al., Reagents for Organic Synthesis, John Wiley and Sons, Inc., pp. 4 and 407 (1967) and reference cited therein. Alternatively, the formula LXIII diol is reacted with two equivalents of sodium hydride and then with excess ethyl formate.

In formula LXIV, $R_{68}$ may also represent a blocking group including benzoyl, substituted benzoyl, monoesterified phthaloyl and substituted or unsubstituted naphthoyl. For introducing those blocking groups, methods known in the art are used. Thus, an aromatic acid of the formula $R_{63}OH$, wherein $R_{63}$ is as defined above, for example benzoic acid, is reacted with the formula LXIII compound in the presence of a dehydrating agent, e.g. zinc chloride; or an anhydride of the aromatic acid of the formula $(R_{63})_2O$, for example benzoic anhydride, is used.

Preferably, however, an acyl halide e.g. $R_{63}Cl$, for example benzoyl chloride, is reacted with the formula-LXIII compound in the presence of a tertiary amine such as pyridine, triethylamine, and the like. The reaction is carried out under a variety of conditions using procedures generally known in the art. Generally, mild conditions are are employed, e.g. 20°–60° C., contacting the reactants in a liquid medium, e.g. excess pyridine or an inert solvent such as benzene, toluene, or chloroform. The acylating agent is used either in stoichiometric amount or in excess.

As examples of reagents providing $R_{63}$ for the purposes of this invention, see the discussion above pertaining to the use of acyl protecting groups.

The formula LXIV acetal is converted to aldehyde LXV by acid hydrolysis, known in the art, using dilute aqueous mineral acids, acetic or formic acids, and the like. Solvents such as acetone, dioxane, and tetrahydrofuran are used.

For the conversion of LXV to LXIX, it is optional whether $R_{66}$ be hydrogen or a "blocking group" as defined below. For efficient utilization of the Wittig reagent it is preferred that $R_{66}$ be a blocking group. If the formula LXIV compound is used wherein $R_{66}$ is hydrogen, the formula LXV intermediate will have hydrogen at $R_{66}$. If $R_{66}$ is to be a blocking group, that may be readily provided prior to conversion of LXV to LXVI by reaction with suitable reagents as discussed below.

The blocking group, $R_{65}$, is any group which replaces hydrogen of the hydroxyl groups, which is not attacked by nor is reactive to the reagents used in the respective transformations to the extent that the hydroxyl group is, and which is substantially replaceable by hydrogen at a later stage in the preparation of the prostaglandin-like products.

Several blocking groups are known in the art, e.g. tetrahydropyranyl, acetyl, and p-phenylbenzoyl (see Corey et al., J. Am. Chem. Soc. 93, 1491 (1971)).

Those which have been found useful include (a) carboxyacyl within the scope of $R_{63}$ above, i.e. acetyl, and also benzoyl, napthoyl, and the like; (b) blocking groups according to $R_{10}$; and (c) —Si(G$_1$)$_3$ wherein G$_1$ is as defined above.

In replacing the hydrogen atoms of the hydroxyl groups with a carboxyacyl blocking group, methods known in the art are used. The reagents and conditions are discussed above for $R_{66}$ on the compound of formula LXIV.

When the blocking group is according to $R_{10}$ appropriate reagents and conditions are as defined above.

When the blocking group is silyl of the formula —Si(G$_1$)$_3$, the formula LXV compound is transformed to a silyl derivative of formula LXV by procedures known in the art. See, for example, Pierce, "Silylation of Organic Compounds," Pierce Chemical Co., Rockford, Illinois (1968). The necessary silylating agents for these transformations are known in the art or are prepared by methods known in the art. See, for example, Post "Silicones and Other Silicon Compounds," Reinhold Publishing Corp., New York, N. Y. (1949). These reagents are used in the presence of a tertiary base such as pyridine at temperatures in the range of about 0° to +50° C. Examples of trisubstituted mono-chlorosilanes suitable for this purpose include chloromethylsilane, chlorotriisobutylsilane, chlorotriphenylsilane, chlorotris(p-chlorophenyl)silane, chlorotrim-tolylsilane, and tribenzylchlorosilane. Alternatively, a chlorosilane is used with a corresponding disilazane. Examples of other silylating agents suitable for forming the formula LXV intermediates include pentamethylsilylamine, pentaethylsilylamine, N-trimethylsilyldiethylamine, 1,1,1-triethyl-N,N-dimethylsilylamine, N,N-diisopropyl-1,1,1-trimethylsilylamine, 1,1,1-tributyl-N,N-dimethylsilylamine N,N-dibutyl-1,1,1-trimethylsilylamine, 1-isobutyl-N,N,1,1-tetramethylsilylamine, N-benzyl-N-ethyl-1,1,1-trimethylsilylamine, N,N1,1-tetramethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilylamine, and 1-methyl-N,N,1,1-tetraphenylsilylamine.

In transforming the formula LXV compound to the formula LXVI compound the aldehyde group is transformed by the Wittig reaction to a moiety of the formula

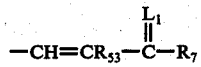

For this purpose a photophonium salt prepared from an organic chloride or bromide of the formula

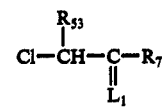

or

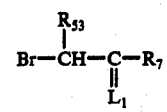

is employed, wherein $L_1$, $R_7$, and $R_{53}$ are as defined above. These organic chlorides or bromides are known in the art or are readily prepared by methods known in the art. See for example the above-identified German Offenlegungsschrift No. 2,209,990. As to the Wittig reaction, see, for example, U.S. Pat. No. 3,776,941 and reference cited therein.

The formula LXVII compound is obtained by deblocking if necessary. When $R_{66}$ is a hindered carboxyacyl, $R_{66}$ on the phenolic hydroxy is selectively replaced with hydrogen by hydrolysis with sodium or potassium hydroxide or carbonate ethanol-water. Other water-miscible solvents may be substituted, for example 1,4-dioxane, tetrahydrofuran, or 1,2-dimethoxyethane. The selective hydrolysis is preferably carried out at −15° to 25° C. Higher temperatures may be used but with some decrease in selectivity.

Total hydrolysis of $R_{66}$ blocking groups on the formula LXVI compound is accomplished, when $R_{66}$ is carboxyacyl, with an alkali alkoxide in an alcoholic solvent, preferably sodium methoxide in methanol at a temperature from 25° C. to 50° C. When $R_{66}$ is trialkylsilyl, either aqueous acid or base are used at 25° to 50° C.

Continuing with Chart B, a Williamson synthesis is employed to obtain the formula LXVIII compound. The formula LXVII phenol is condensed with a haloalkanoate within the scope of Hal—(CH$_2$)$_g$—COOR$_1$ wherein Hal is chloro, bromo, or iodo and g and R$_1$ are as defined above. Preferably, however, the reaction proceeds by the Method of Chart A for preparing 5-oxa-PG-type compounds, i.e., the transformation of XXXV to XXXVI.

The transformation of the formula LXVIII compound to the formula LXIX is accomplished by any one of several routes known in the art. See U.S. Pat. No. 3,711,515. Thus, the alkene LXVIII is hydroxylated to glycol LXIX. For this purpose osmium tetroxide is a suitable reagent, for example in conjunction with N-methylmorpholine oxidehydrogen peroxide complex (see Fieser et al., "Reagents for Organic Synthesis", p. 690, John Wiley and Sons, Inc., New York (1967)). Thereafter, several methods are available for obtaining the formula LXX product. In one method the glycol is converted to a bis(alkanesulfonic acid) ester and subsequently hydrolyzed to the formula LXX compound by methods known in the art (See, for example German Offenlegungsschrift No. 1,936,676, Derwent Farmdoc No. 6862R). Another method is by way of a diformate by formolysis of of the glycol (see U.S. Pat. No. 3,711,515).

Still another method is by way of a cyclic ortho ester. For this purpose, glycol LXIX is reacted with an ortho ester of the formula

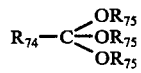

wherein R$_{74}$ is hydrogen, alkyl of one to 19 carbon atoms, inclusive, or aralkyl of 7 to 12 carbon atoms, inclusive, substituted with zero to 3 halo atoms; and R$_{75}$ is methyl or ethyl. There is then formed a cyclic ortho- ester of the formula

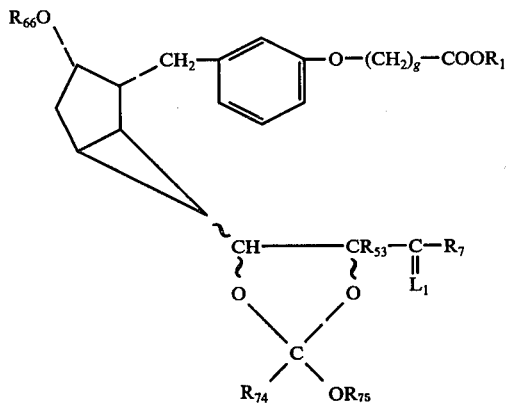

wherein g, R$_1$, R$_{53}$, R$_{66}$, R$_{74}$, R$_{75}$, L$_1$ and R$_7$ are as defined above. The reaction goes smoothly in a temperature range of $-50°$ C. to $+100°$ C., although for convenience $0°$ C to $+50°$ C. is generally preferred. From 1.5 to 10 molar equivalents of the ortho ester are employed, together with an acid catalyst. The amount of the catalyst is usually a small fraction of the weight of the glycol, e.g., about 1%, and typical catalysts include pyridine hydrochloride, formic acid, hydrogen chloride, p-toluenesulfonic acid, trichloroacetic acid, or trifluroacetic acid. The reaction is preferably run in a solvent, for example benzene, dichloromethane, ethyl acetate, or diethyl ether. It is generally completed within a few minutes and is conveniently followed by TLC (thin layer chromatography on basic silica gel plates).

The ortho ester reagents are known in the art or readily available by methods known in the art. See for example S. M. McElvain et al., J. Am. Chem. Soc. 64, 1925 (1942), starting with an appropriate nitrile. Examples of useful ortho esters include:

trimethyl orthoformate,
triethyl orthoacetate,
triethyl orthopropionate,
trimethyl orthobutyrate,
trimethyl orthovalerate,
trimethyl orthooctanoate,
trimethyl orthophenylacetate, and
trimethyl ortho (2,4-dichlorophenyl)acetate.

Preferred are those ortho esters wherein R$_{74}$ is alkyl of one to 7 carbon atoms; especially preferred are those wherein R$_{74}$ is alkyl of one to 4.

Next, the cyclic orthoester depicted above is reacted with anhydrous formic acid to yield a diol diester of the formula

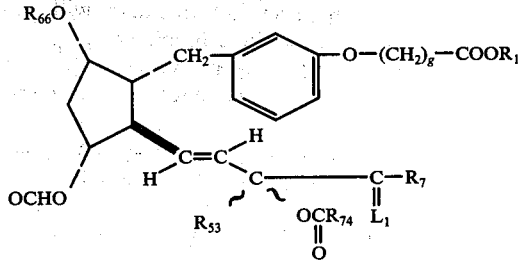

wherein g, R$_1$, R$_7$, R$_{53}$, R$_{66}$, and L$_1$ are as defined above.

Anhydrous formic acid refers to formic acid containing not more than 0.5% water. The reaction is run with an excess of formic acid, which may itself serve as the solvent for the reaction. Solvents may be present, for example dichloromethane, benzene, or diethyl ether, usually not over 20% by volume of the formic acid. There may also be present organic acid anhydrides, for example acetic anhydride, or alkyl orthoesters, for example trimethyl orthoformate, which are useful as drying agents for the formic acid. Although the reaction proceeds over a wide range of temperatures, it is conveniently run at about $20°$-$30°$ C. and is usually completed within about 10 minutes.

Finally, the diol diester above is converted to product LXX by methods known in the art, for example by hydrolysis in the presence of a base in an alcoholic medium. Examples of the base are sodium or potassium carbonate or sodium or potassium alkoxides including methoxides or ethoxides. The reaction is conveniently run in an excess of the solvolysis reagent, for example methanol or ethanol. The temperature range is from $-50°$ C. to $100°$ C. The time for completion of the reaction varies with nature of R$_{74}$ and the base, proceeding in the case of alkali carbonates in a few minutes when R$_{74}$ is hydrogen but taking up to several hours when R$_{74}$ is ethyl, for example.

When the solvolysis proceeds too long or when conditions are too severe, an ester group (R$_1$) is often removed. They are, however, readily replaced by methods known in the art. See the discussion below.

The formula LXXI compound is prepared from the formula LXX compound first by oxidation of the C-15 hydroxy to a 15-oxo. Accordingly, as is known in the art, 2,3-dichloro-5,6-dicyano-1,4-benzoquinone, activated manganese dioxide, or nickel peroxide (See Fieser, et al., "Reagents for Organic Synthesis", John Wiley and Sons, New York, N.Y., pgs. 215, 637, and 731) is advantageously employed. Thereafter, the formula LXXI compound is prepared from the 15-oxo compound by transforming the C-9 and C-11 hydroxy hydrogens to R$_{65}$ blocking groups. Procedures known in the art are employed. See for reference Pierce, "Silylation of Organic Compounds," Pierce Chemical Company, Rockford, Ill. (1968) and the discussion above pertaining to the introduction of blocking groups according to R$_{10}$. The necessary silylating reagents for these transformations are known in the art or are prepared by methods known in the art. See for reference, Post, "Silicones and Other Silicone Compounds," Reinhold Publishing Corp., New York, N.Y. (1949).

The formula LXXII compound is then prepared from the formula LXXI compound by the procedure described in Chart A for transforming the formula XXII compound to the formula XXIII compound, followed by hydrolysis of the silyl groups, using, for example, dilute aqueous acetic acid in a water miscible solvent, such as ethanol (sufficient to yield a homogeneous reaction mixture). At 25° C., the hydrolysis is ordinarily complete in 2 to 12 hrs. Further, the hydrolysis preferably carried out in an inert atmosphere, e.g., nitrogen or argon.

The formula LXXIII compound is prepared from the formula LXII compound by separation of the 15-epimers when present. Such separation proceeds by methods discussed above for accomplishment of this purpose (e.g., silica gel chromatography or high pressure liquid chromatography).

Referring to Chart C, there are shown process steps by which the formula LXXVI bicyclo hexene is transformed first to an oxetane (Formula LXXVII) with a fully developed side chain, e.g.,

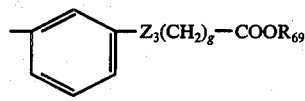

wherein $Z_3$ is oxa or methylene and ultimately to the formula LXXXIV compound. In Chart C, $R_{69}$ is hydrogen or alkyl of one to 4 carbon atoms, inclusive, and $R_{70}$ is hydrogen, alkyl of one to 4 carbon atoms, inclusive, or silyl of the formula $(G_1)_3Si$- wherein $G_1$ is as defined herein above.

In transforming LXXVI to LXXVII in Chart C, there is employed an aldehyde of the formula

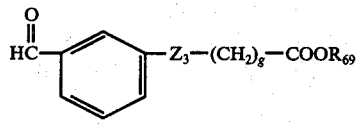

wherein $Z_3$ and $R_{69}$ are as defined above. Such aldehydes are available or are readily prepared by methods known in the art, e.g.

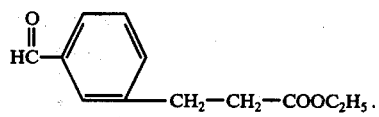

The conditions for this transformation are essentially the same as for the corresponding step of Chart B (i.e., LXI to LXII). Thereafter, the preparation of the formula LXXXI compound proceeds by methods analogous to the corresponding steps of Chart B (i.e., LXII to LXVI) with the preference that LXXVII to LXXVIII is accomplished catalytically.

The steps transforming LXXXI to LXXXIV then proceed in similar fashion, employing the same or similar reagents and conditions as the corresponding steps of Chart B discussed above.

As discussed above, Chart D provides a method whereby the formula XCI PG-type intermediate, prepared according to Chart B or Chart C is transformed to the corresponding formula XCIV 16-phenoxy-PG-type intermediates.

The formula XCII compound is prepared from the formula XCI compound by cleavage of the 13,14-trans double bond, conveniently by ozonolysis. Ozonolysis proceeds by bubbling dry oxygen, containing about 3 percent ozone, through a mixture of a formula XCI compound in a suitable nonreactive diluent. For example, n-hexane is advantageously employed. The ozone may be generated using methods known in the art. See, for example, Fieser, et al., "Reagents for Organic Synthesis," John Wiley and Sons, Inc. (1967), pages 773-777. Reaction conditions are maintained until the reaction is shown to be complete, for example, by silica gel thin layer chromatography or when the reaction mixture no longer rapidly decolorizes a dilute solution of bromine in acetic acid.

The formula XCIII compound is then prepared from the formula XCII compound by blocking with an $R_{65}$ blocking group and thereafter employing a phosphonate of the formula:

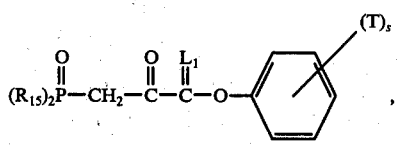

wherein $R_{15}$, $L_1$, T, and s are as defined above. Phosphonates of this general formula are prepared by methods known in the art. See the text hereinabove accompanying Chart A for discussion of the preparation and the appropriate reaction conditions by which the Wittig reaction proceeds. The formula XCIV compound is prepared from the formula XCIII compound by transformation of the 15-oxo moiety to an $M_1$ moiety. Methods hereinabove, particularly those discussed in Chart A above, are employed.

Optionally the method of Chart D is used to introduce the various other $R_7$ moieties to the formula XCII compound using the appropriate phosphonate.

Chart E provides a method whereby the formula CI 14-halo-PGF$_\alpha$-type intermediate prepared above is transformed to the corresponding CIX formula 14-halo-PGD-type compound; formula CX 14-halo-9-deoxy-9,10-didehydro-PGD-type compound; or formula CXV 14-halo-9-deoxy-PGD-type compound.

The formula CII compound is prepared from the formula CI compound by cycloalkylboronization when and only when $R_5$ is hydrogen. Accordingly, the bicyclic formula CII compound is prepared by reaction of the formula CI compound with a slight stoichiometric excess of an alkylboronic acid. The course of the reaction is conveniently monitored by silica gel thin layer chromatography and the reaction is preferably carried forth under vigorous stirring at reflux temperatures. The preferred reaction diluent for this transformation is methylene chloride, though other suitable organic solvents are likewise employed. The formula CII compound so formed is then etherified by replacing the free hydroxy hydrogen of the $M_1$ moiety with a blocking group according to $R_{10}$. Procedures hereinabove described are advantageously employed. Thereafter the formula CIV compound, which is represented by formula CI when $R_5$ is methyl, is prepared from the formula CIII compound by decycloboronization. For this purpose an alkali metal hydroxide (e.g., sodium, lithium, or potassium hydroxide) is combined with the formula CIII compound in a water-miscible diluent capable of yielding a homogeneous reaction mixture (e.g., methanol or ethanol), and the resulting solution thereafter treated with dilute aqueous hydrogen peroxide. The formula CIX compound is then prepared from the formula CIV compound by one of two methods.

By the first method the formula CIV compound is selectively oxidized at the C-11 over the C-9 position using, for example, the Jones reagent. In order to achieve high selectivity, it is desirable that the reaction be carried out at between $-20°$ and $-60°$ C. Especially preferred are reaction temperatures between $-55°$ and $-40°$ C. Accordingly, upon separation of mixtures of product, the pure formula CXI PGD-type intermediate is obtained.

By the second procedure the formula CIX compound is prepared from the formula CIV compound by first selectively silylating the C-11 hydroxy of the formula CIV compound over the C-9 hydroxy. Silyl groups according to the formula -Si-$(G_1)_3$ are advantageously employed. For selective monosilylation procedures see U.S. Pat. No. 3,822,303, issued July 2, 1974, German Offenlegungschrift 2259195, Derwent Farmdoc CPI 36457U-B or Netherlands Pat. No. 7214142, Derwent Farmdoc CPI 26221U-B. Thereafter the silylated compound so formed (formula CV) is transformed to the corresponding C-9 ether (formula CVI), employing blocking groups according to $R_{10}$, in place of the 9-hydroxy hydrogen. Thereafter the C-11 silyl moiety is hydrolyzed by methods hereinabove described and the resulting 11-hydroxy compound (formula CVII) oxidized by the procedure described above, yielding the corresponding 11-oxo compound (formula CVIII).

Thereafter, the formula CIX compound is prepared from this 11-oxo compound (formula CVIII or CXI) by replacing any blocking groups according to $R_{10}$ with hydrogen. Methods described hereinabove are employed.

Additionally Chart E provides a method whereby formula CIX or CXI 14-halo-PGD-type compound is transformed variously into the formula CX or CXII 14-halo-9-deoxy-9,10-didehydro-PGD-type compound, respectively, and to the formula CXV 14-halo-9-deoxy-PGD-type compound.

The formula CX or CXII compound is prepared, respectively, from the formula CIX or CXI compound by mild acid catalyzed dehydration of the formula CIX or CXI compound. Organic acids such as acetic acid, trifluoroacetic acid, citric acid, oxalic acid, or p-toluenesulfonic acid are useful for this purpose. Diluents such as tetrahydrofuran, methanol, ethanol, or water are usefully employed. Preferably, however, a diluent is employed which will result in a homogeneous reaction mixture. The dehydration proceeds rapidly at temperatures between ambient temperature and 40° C. Alternatively, a formula CIX or CXI compound is left standing on a column of acid washed silica gel, thereby dehydrating to the formula CX or CXII compound usually within one to 5 days. The formula CXIII compound is thereafter prepared from the CXII compound by reduction of the formula CXII compound. This reduction selectively reduces the endocyclic double bond and transforms the 11-oxo to an 11-hydroxy, without affecting side chain unsaturation. For this purpose, an alkali metal borohydride, e.g. sodium, potassium, or lithium borohydride is effectively employed in aqueous alcoholic solution. The reaction is carried out at about $-20°$ C. and is ordinarily complete within a few minutes. The formula CXIV compound is then prepared by one of two methods.

The formula CXII compound is optionally converted into the formula CXIV compound by selective catalytic hydrogenation of the endocyclic double bond. This transformation is selectively effective without affecting side chain unsaturation. For this purpose the 5 to 10 percent palladium or rhodium catalyst on carbon, alumina, or other suitable support is employed. The reaction is carried out in any sutiable organic solvent, e.g. ethyl acetate, methanol, ethanol, or diethyl ether, at temperatures of between $-30°$ and 50° C. and pressures greater than or equal to atmospheric pressure.

Alternatively the formula CXIV compound is prepared from the formula CXIII compound by oxidation as described above in the transformation of the formula CIV compound to the formula CXI compound. For this purpose an oxidizing agent such as the Jones reagent (acidified chromic acid) is employed. See for reference, Journal of the Chemical Society 39 (1946). A slight stoichiometric excess beyond the amount necessary to oxidize the secondary hydroxy group of the formula CXIII compound is employed. Acetone is a useful diluent for this purpose. Reaction temperatures at least as low as about 0° C. are useful. Preferred reaction temperatures are in the range of $-10°$ to $-50°$ C. An especially useful reagent for this purpose is the Collins reagent (chromium trioxide in pyridine). See for reference J. C. Collins, et al., Tetrahedron Letters 3363 (1968). Dichloromethane is a suitable diluent for this purpose. Reaction temperatures below 30° C. are preferred. Reaction temperatures in the range of about $-10°$ to $+10°$ C. are especially preferred. The oxidation proceeds rapidly and is ordinarily complete within several minutes. Pure product is then isolated by conventional means, e.g. silica gel chromatography.

Examples of other oxidation agents useful for this transformation are mixtures of chromium trioxide in pyridine (Journal of the American Chemical Society 75, 422 (1953)), and tert-butyl chromate in pyridine (Biological Chemistry Journal, 84, 195 (1962)), mixtures of sulfur trioxide in pyridine and dimethyl sulfoxide (Journal of the American Chemical Society 89, 5505 (1967)), and mixtures of dicyclohexylcarbodiimide and dimethylsulfoxide (Journal of the American Chemical Society 87, 5661 (1965)).

Thereafter the formula CXV compound is prepared from the formula CXIV compound by hydrolysis of blocking groups according to $R_{10}$, as described hereinabove.

Chart F provides a method whereby the formula CXXI compound (as known in the art, or as prepared herein) is transformed to the corresponding formula CXXVI 14-halo-PGF- or 11-deoxy-14-halo-PGF-type compound.

The formula CXXII compound is prepared from the formula CXXI compound by selective oxidation of the C-15 alcohol. The oxidation is accomplished employing conventional methods known in the art, for example, the use of 2,3-dichloro-5,6-dicyanobenzoquinone, activated manganese dioxide, or nickel peroxide. See Fieser, et al. "Reagents for Organic Synthesis" John Wiley and Sons, New York, N.Y. pages 215, 637, and 731.

The formula CXXII compound is prepared from the formula CXXII compound by protection of free hydroxy moieties with acyl protecting groups according to $R_9$. Methods described hereinabove for preparing these acyl derivatives are employed. Optionally, however, silyl groups within the scope of -Si$(G_1)_3$, wherein $G_1$ is defined above, are employed in place of the acyl protecting groups. Finally, the acyl protection or silylation described herein is optionally omitted, particularly, where $R_5$ and $R_6$ of the $M_1$ moiety of the formula CXXVI compound are both hydrogen.

The formula CXXIV compound is prepared from the formula CXXIII compound by 14-halogenation. This 14-halogenation is achieved by one of several general methods known in the art. For example, following the procedure of Chart A wherein the 14-halo compound is prepared from the formula XXII compound, formula CXXIV compound herein is prepared. As especially useful reagent for the instant transformation is sulfuryl chloride, as described above. Mixtures of products produced are separated, using conventional techniques. The formula CXXV compound is then prepared from the formula CXXIV compound by transformation of the 15-oxo to an $M_1$ moiety. Techniques as described hereinabove are employed. Thereafter, the formula CXXVI compound is prepared from the formula CXXV compound by removal of the optionally present acyl or silyl protecting groups, following the procedures described hereinabove.

Chart G provides a method whereby 14-halo-PGA-type compounds are transformed into corresponding 14-halo-11-deoxy-PGE-type compounds, according to formula CXLII or CXLVI.

The formula CXLII compound is prepared from the formula CXLI compound by selective catalytic hydrogenation of the endocyclic double bond. This transformation is selectively effected without affecting side-chain unsaturation. For this purpose a 5 to 10 percent palladium or rhodium catalyst on carbon, alumina or other suitable support is employed. The reaction is carried out in any suitable organic solvent, e.g. ethyl acetate, methanol, ethanol, or diethyl ether at temperatures of $-30°$ to $+50°$ C. and pressures greater then or equal to the atmospheric pressure, but less than several atmospheres.

The formula CXLIII compound is prepared from the formula CXLI compound by replacing any free hydroxy hydrogen with a blocking group, according to $R_{31}$.

This blocking group function prevents attack on the hydroxy by subsequent reagents, especially the reagent employed herein for the transformation of the C-9 hydroxy to a C-9 oxo group. This blocking group further functions so as to be replaceable by hydrogen at a later stage in the preparation of the prostaglandin-type products. Blocking groups, according to $R_{31}$, which are useful for these purposes include alkanoyl of 2 to 12 carbon atoms, inclusive, tetrahydropyranyl, tetrahydrofuranyl, a group of the formula

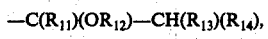

wherein $R_{11}$, $R_{12}$, $R_{13}$, and $R_{14}$ are as defined above, and a silyl group of the formula $-Si(G_1)_3$, wherein G is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive.

The transformations of Chart G which involve replacing any hydroxy hydrogen with a blocking group according to $R_{31}$ employ methods known in the art. Further subsequent hydrolysis of these blocking groups according to $R_{31}$ proceeds by methods known in the art.

When the blocking group is of the formula

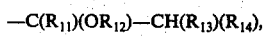

wherein $R_{11}$, $R_{12}$, $R_{13}$, and $R_{14}$ are as defined above, the appropriate reagent is a vinyl ether, e.g. isobutyl vinyl ether or any vinyl ether of the formula

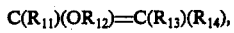

wherein $R_{11}$, $R_{12}$, $R_{13}$, and $R_{14}$ are as defined above; or an unsaturated cyclic or heterocyclic compound, e.g. 1-cyclohexen-1-yl methyl ether or 5,6-dihydro-4-methoxy-2H-pyran. See C. B. Reese, et al., Journal of the American Chemical Society 89, 3366 (1967). The reaction conditions for such vinyl ethers and unsaturates are similar to those for dihydropyran above.

The subsequent hydrolysis of these blocking groups according to $R_{31}$ proceeds by methods known in the art. Silyl groups are readily removed by prior art procedures known to be useful for transforming silyl ethers and silyl esters to alcohols and carboxylic acids, respectively. For reference see Pierce, cited above, especially page 447 thereof. A mixture of water and a sufficient quantity of a water miscible organic diluent to yield the homogeneous reaction mixture represents a suitable reaction medium. Addition of a catalytic amount of an organic or inorganic acid hastens the hydrolysis. The length of time required for hydrolysis is determined in part by temperature. With a mixture of water and methanol at 25° C. Several hours is usually sufficient for hydrolysis. At 0° C., several days are required.

For the hydrolysis of the various other blocking groups according to $R_{31}$ mild acidic conditions are employed.

The formula CXLIV compound is prepared from the formula CXLIII compound by reduction of the formula CXLIII compound with reducing agent which selectively effects reduction of the ring unsaturation and reduction of the C-9 oxo group to a C-9 hydroxy group, without reducing side chain unsaturation. For this purpose an alkali metal borohydride, e.g. sodium, potassium, or lithium borohydride is effectively employed in aqueous solution. The reaction is carried at about $-20°$ C. and is complete within a few minutes.

The formula CXLV compound is prepared by oxidation of the formula CXLIV compound using an oxidizing reagent, such as the Jones reagent (acidified chromic acid). See for reference Journal of the Chemical Society 39 (1946). A slight stoichiometric excess beyond the amount necessary to oxidize a single hydroxy group is employed. Acetone is a useful diluent for this purpose. Reaction temperatures at least as low as about 0° C. should be used. Preferred reaction temperatures are in the range of $-10°$ to $-50°$ C. An especially useful reagent for this purpose is the Collins reagent (chromium trioxide in pyridine). See for reference J. C. Collins, et al., Tetrahedron Letters 3363, (1968). Dichloromethane is a suitable diluent for this purpose. Reaction temperatures below 30° C. are preferred. Reaction temperatures in the range of $-10°$ to $+10°$ C. are especially preferred. This oxidation proceeds rapidly and is complete within several minutes. The formula CXLV compound may then be isolated by conventional methods, e.g. silica gel chromatography.

Examples of other oxidation reagents useful for this transformation are silver carbonate on celite (Chemical Communications 1102 (1969), mixtures of chromiun trioxide in pyridine (Journal of the American Chemical Society 75, 422 (1953)), and Tetrahedron Letters, 18, 1351 (1962)), tert-butyl chromate in pyridine (Biological Chemical Journal, 84, 195 (1962)), mixtures of sulfur trioxide in pyridine and dimethyl sulfoxide (Journal of the American Chemical Society 89, 5505 (1967)), and mixtures of dicyclohexylcarbodiimide and dimethyl sulfoxide (Journal of the American Chemical Society 87, 5661 (1965)).

The formula CXLVI compound is then prepared from the formula CXLV compound by hydrolysis of the blocking groups, according to $R_{31}$, as described above.

From the formula CXLVI 14-halo-11-deoxy-PGE-type compound, there is prepared the corresponding 14-halo-11-deoxy-PGF$_\alpha$- or PGF$_\beta$-type compound employing methods described in Chart A for the analogous transformation.

Chart H provides a method whereby the formula CLI 14-halo-PGF$_\alpha$ or 14-halo-11-deoxy-PGF$_\alpha$-type starting material, as prepared herein, is transformed into the corresponding 14-halo-PGE- or 14-halo-11-deoxy-PGE-type compound by selective silylation of all non-tertiary hydroxy hydrogens of the formula CLI compound, other than the C-9 hydroxy.

The formula CLII compound is prepared from the formula CLI compound by selective silylation of the various non-tertiary hydroxy groups of the formula CLI compound over the C-9 hydroxy. Silyl groups with the scope —Si(G$_1$)$_3$, wherein G is alkyl of 1 to 4 carbon atoms, inclusive, aralkyl of 7 to 12 carbon atoms, inclusive, phenyl, phenyl substituted with one or 2 chloro, fluoro, or alkyl of one to 4 carbon atoms, inclusive, with the proviso that the various G's of the —Si(G)$_3$ moiety are the same or different, are employed. These reagents are known in the art and their use is known in the art.

For the selective silylation procedure of Chart H procedures known in the art for selective silylation of known prostanoic acid derivatives are employed. See for reference U.S. Pat. No. 3,822,303 (issued July 2, 1974), German Offenlegungschrift 2,259,195 (Derwent Farmdoc CPI 36457U-B), and Netherlands Pat. No. 7,214,142 (Derwent Farmdoc CPI 26221U-B).

Examples of the -Si(G$_1$)$_3$ moiety are trimethylsilyl, dimethyl(tert-butyl)silyl, dimethyl phenyl silyl, and methylphenylsilyl. Examples of alkyl of one to 4 carbon atoms, inclusive, aralkyl of 7 to 12 carbon atoms, inclusive, and phenyl or substituted phenyl moieties are provided hereinabove.

The formula CLIII compound is prepared from the formula CLII compound by oxidation of the C-9 hydroxy to a C-9 oxo. Oxidation reagents and methods known in the art are employed. For example, the Jones reagent is advantageously employed as discussed above.

The formula CLIV compound is prepared from the formula CLIII compound by hydrolysis of any silyl groups. Hydrolysis proceeds by methods known in the art, e.g. the use of water or dilute aqueous acetic acid in diluent of water and a quantity of a water miscible solvent sufficient to yield a homogeneous reaction mixture. This hydrolysis is ordinarily complete within 2 to 12 hours at 25° C., and is preferably carried in an atmosphere of an inert gas such as nitrogen or argon.

Optionally the procedure of Chart H is used to transform 13,14-didehydro-PGF$_\alpha$- or 2-decarboxy-2-hydroxymethyl-13,14-didehydro-PGF$_\alpha$-type products to corresponding PGE-type products. Accordingly, in this alternate process Y$_1$ in this Chart is defined to be —C≡C— instead of trans-CH═C(Hal)—.

Chart J provides a method whereby the 14-halo compounds described above are transformed to corresponding 13,14-didehydro-PG-type products.

The transformation of Chart J (the formula CLXI compound to the formula CLXII compound) proceeds by dehydrohalogenation. By the preferred method the reaction proceeds using as a reaction diluent a mixture of dimethylsulfoxide, or similar aprotic solvent, and the methanol in ratio by volume between 5:1 and 10:1. Thereafter a strong organic base, for example potassium t-butoxide or sodium methoxide is added and the reaction is allowed to proceed to completion, ordinarily within about 24 hours. Reaction temperatures between 0°-25° C. are employed for convenience.

When this dehydrohalogenation procedure is employed using 14-halo-PGE-, 14-halo-PGA, or 14-halo-PGD-type compounds undesired dehydration and/or double bond migration occurs. Accordingly, it is preferred that these dehydrations be performed on PGF-type reactants and thereafter the corresponding 13,14-didehydro-PGF-type compounds be transformed respectively to 13,14-didehydro-PGE-, PGA- or PGD-type products, by procedures described hereinabove. Accordingly, by this preferred method the 14-halo-PGF compound is successively transformed to a 13,14-didehydro-PGF-type compound and thereafter to 13,14-didehydro-PGE- or PGA- or PGD-type compound.

As a further option to Chart J, the dehydrohalogenation is performed on a 2-decarboxy-2-hydroxymethyl-14-halo-PG-type compound, yielding thereby a 2-decarboxy-2-hydroxymethyl-13,14-didehydro-PG-type product. Appropriate measures are discussed in the preceeding paragraph to avoid undesired dehydration and/or double bond migrations.

Chart K provides a method whereby the PG-type intermediates prepared in preceeding charts are transformed to the corresponding 2-decarboxy-2-hydroxymethyl-13,14-didehydro-PG-type compounds of the present invention.

The present transformation (CXXI to CXXII) proceeds by reduction of the carboxylic acid or ester with reagents known to reduce carboxylic acids to corresponding primary alcohols. For example, when the formula CXXI compound is an acid or an ester, the reduction proceeds with lithium aluminum hydride or diisobutylaluminum hydride.

Useful solvents include diethyl ether, tetrahydrofuran, dimethoxyethane, or like organic solvents. The reaction is conveniently run at temperatures of about −78° C. to 100° C., although preferably at about 0° C. to 50° C. When the formula CXXI compound is an acid, reducing agents such as diborane are also employed when double bond reduction is not a problem.

When the formula CXXI compound contains a carbonyl function on the cyclopentane ring, the reduction described in the preceeding paragraph frequently reduces that carbonyl to the corresponding alcohol. Thus, the preparation of the formula CXXII compound in this case requires oxidation of the hydroxy so produced to a corresponding 9-oxo compound. In this case, it is desirable to first provide protection for the carbonyl by its transformation to a corresponding oxime, ethylene ketal, or similar carbonyl derivative before the reduction of the carboxylic acid is attempted. Thereafter, the protected carbonyl derivative is removed, preparing the formula CXXII product. Introduction and removal of these carbonyl protecting groups is accomplished by methods known in the art.

Alternatively, the formula CXXI 13,14-didehydro-PGF-type compound is transformed first to the corresponding 2-decarboxy-2-hydroxymethyl-13,14-didehydro-PGF-type compound and then to a 2-decarboxy-2-hydroxymethyl-13,14-didehydro-PGE-, PGA-, PGD-, 9-deoxy-PGD-, 9,10-didehydro-9-deoxy-PGD-type compound following the procedure described in preceding charts for transforming PGF-type compounds to PG-type compounds of the various cyclopentane ring structures described herein. Likewise, the corresponding formula CXXI 13,14-didehydro-11-deoxy-PGF-type compound is transformed to a 13,14-didehydro-2-decarboxy-2-hydroxymethyl-11-deoxy-PGF-type compound and thereafter to the corresponding formula CXXII 2-decarboxy-2-hydroxymethyl- 13,14-didehydro-11-deoxy-PGE or 11-deoxy-PGF$_\beta$-type compounds.

By another route the 2-decarboxy-2-hydroxymethyl-13,14-didehydro-PGE-type product is prepared from the 2-decarboxy-2-hydroxymethyl-13,14-didehydro-PGF-type starting material by first selectively silylating at C-1, C-11 and C-15 (where $R_5$ is hydrogen) over C-9, and then oxidizing and hydrolyzing the silyl groups. Methods known in the art are employed.

Chart L provides a method whereby the formula CXXXI lactol intermediate of Chart A is transformed to the various 2-decarboxy-2-hydroxymethyl-13,14-didehydro-PG-type products disclosed herein. The formula CXXXII compound is prepared from the formula CXXXI compound employing a Wittig alkylation as described in Chart A for the preparation of the formula XXXIII compound except that a Wittig reagent prepared from a corresponding (ω-tetrahydropyranyloxymethylalkyl)triphenphonsphonium bromide is used in place of the (ωcarboxyalkyl)triphenylphsophonium bromide of Chart A. Alternatively, and preferably when PGF- or 11-deoxy-PGF-type products are to be prepared, an (ω-hydroxymethylalkyl)triphenylphosphonium bromide is employed in this Wittig alkylation. Thereafter, the formula CXXXIV PGE or 11-deoxy-PGE-type compound is prepared from the PGF-type compound by oxidation, employing for example the Jones reagent or Collings reagent as described above. Thereafter, the formula CXXXV compound wherein $M_{18}$ is

is prepared from the formula CXXXIV compound by ring carbonyl reduction followed by separation of the 9-hydroxy epimers (employing methods hereinabove described), hydrolysis of any blocking groups, and separation of any mixed C-15 epimers. The hydrolysis of the blocking groups and separation of the epimers proceeds by methods hereinabove described. Alternatively, the formula CXXXV compound is prepared from the formula CXXXII compound or formula CXXXIII compound by hydrolysis of the blocking groups followed by separation of any mixed C-15 epimers as described above. Thereafter, the formula CXXXVI compound is prepared from the formula CXXXV compound wherein $M_{18}$ is

and $R_8$ is hydroxy by acidic dehydration employing methods hereinabove described.

The various formula CXXXV 2-decarboxy-2-hydroxymethyl-14-halo-PG-type compounds are optionally dehydrohalogenated (especially when $M_{19}$ is not $$\overset{O}{\underset{||}{}})$$

to 2-decarboxy-2-hydroxymethyl-13,14-didehydro-PG-type products.

The transformations of Chart M provide a method whereby the 2-decarboxy-2-hydroxymethyl-13,14-didehydro-PGE$_\alpha$-type compounds of formula CXXXVII are transformed to the corresponding 2-decarboxy-2-hydroxymethyl-13,14-didehydro-PGD-, 9-deoxy-PGD-, or 9,10-didehydro-9-deoxy-PGD-type products. These transformations follow the method described in Chart E for the preparation of corresponding carboxylic acids.

Accordingly, the formula CXXXVIII compound is prepared from the formula CXXXVII compound by the method described in Chart E for the preparation of the formula CIV compound from the formula CI compound. Thereafter the formula CXXXIX compound is prepared from the formula CXXXVIII compound by the method described for the preparation of the formula CIX compound from the formula CIV compound. Further, the formula CXL compound is prepared by the method described for the preparation of the formula CX compound from the formula CIX compound. Finally, the formula compound is prepared from the formula CXXXIX compound by the method described above for the preparation of the formula CXV from the formula CXI compound.

In all of the above described reactions, the products are separated by conventional means from starting material and impurities. For example, by use of silica gel chromatography monitored by thin layer chromatography the products of the various steps of the above charts are separated from the corresponding starting materials and impurities.

Finally, the various hydroxy-containing PG-type products are optionally carboxylated. The reaction time for carboxyacylation will depend on such factors as the reaction temperature, and the nature of the anhydride and tertiary amine reactants. With acetic anhydride, pyridine, and a 25° C. reaction temperature, a 6 to 24 hour reaction time is used.

The carboxyacylated product is isolated from the reaction mixture by conventional methods. For example, the excess anhydride is decomposed with water, and the resulting mixture acidified and then extracted with a solvent such as diethyl ester. The desired carboxyacylate is recovered from the diethyl ether extract by evaporation. The carboxyacylate is then purified by conventional methods, advantageously by chromatography or crystallization.

DESCRIPTION OF THE PREFERRED EMBODIMENTS

The invention can be more fully understood by the following examples and preparations.

All temperatures are in degrees centigrade.

IR (Infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer on deuterochloroform solutions with tetramethylsilane as an internal standard (downfield).

Mass spectra are recorded on an CEG model 110B Double Focusing High Resolution Mass Spectrometer or an LKB Model 9000 Gas-Chromatograph-Mass Spectrometer. Trimethylsilyl derivatives are used, except where otherwise indicated.

The collection of chromatographic eluate fractions starts when the eluant front reaches the bottom of the column. "Brine", herein, refers to an aqueous saturated sodium chloride solution.

The A-IX solvent used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas Hoover melting point apparatus.

DDQ refers to 2,3-dichloro-5,6-dicyano-1,4-benzoquinone.

THF refers to tetrahydrofuran.

Specific Rotations, [α], are determined for solutions of a compound in the specified solvent at ambient temperature with a Perkin-Elmer Model 141 Automatic Polarimeter.

EXAMPLE 1

Dimethyl 3,3-dimethyl-2-oxo-4-phenylbutylphosphonate,

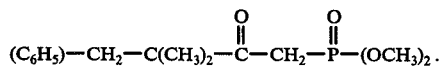

A. To a solution of 101.2 g. of diisopropylamine in 125 ml. of tetrahydrofuran under nitrogen at 0° C. is added dropwise with cooling (using an ice-methanol bath) 625 ml. of 1.6M n-butyllithium in hexane. To the resulting solution is added dropwise with cooling 46.5 ml. of isobutyric acid. This mixture is then stirred at 0° C. for 90 min. and thereafter cooled to −15° C. Benzyl chloride (60 ml.) is added with stirring at such a rate as to maintain the reaction temperature below −5° C. The resulting mixture is thereafter stirred at ambient temperature for 4 hours. This stirred mixture is then diluted with diethyl ether and excess cold dilute hydrochloric acid. The organic layer is washed with saline and thereafter dried, concentrated, and the residue distilled under vacuum. Accordingly, there is prepared 2,2-dimethyl-3-phenyl propionic acid.

B. A mixture of 48 g. of the product of part A of this example and 82 g. of thionyl chloride are heated with stirring on a steam bath for 2 hours. The mixture is then concentrated under vacuum. Thereafter dry benzene is added and the resulting mixture is concentrated again, removing all traces of thionyl chloride. Distillation of this residue yields 48.2 g. of 2,2-dimethyl-3-phenylpropionyl chloride.

C. To a solution of 63 g. of dimethylmethylphosphonate in 600 ml. of tetrahydrofuran under nitrogen at −75° C. is added with stirring 312 ml. of 1.6 molar n-butyllithium in hexane. The addition rate is adjusted so that the reaction temperature remains below 55° C. Ten minutes after the addition is complete, 48.2 g. of the reaction product of part B of this example and 50 ml. of tetrahydrofuran are added dropwise at such rate as to maintain the reaction temperature below −60° C. The resulting mixture is then stirred at −75° C. for 2 hours and then ambient temperature overnight. Acetic acid (20 ml.) is thereafter added and the resulting mixture distilled under vacuum, thereby removing most of the tetrahydrofuran. The residue is then shaken with diethyl ether in methylene chloride (3:1 by volume) and a cold dilute sodium bicarbonate solution. The organic layer is then washed with brine, dried, and concentrated. The residue is crystallized from diethyl ether, yielding 54 g. of dimethyl 3,3-dimethyl-2-oxo-4-phenylbutylphosphorate the title compound. The melting point is 48°–50° C.

Following the procedure of Example 1, but using in place of benzyl chloride substituted benzyl chlorides of the formula

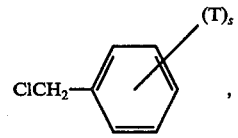

wherein T is fluoro, chloro, trifluoromethyl, alkyl of one to 3 carbon atoms, inclusive, or alkoxy of one to 3 carbon atoms, inclusive, and wherein s is zero, one, 2, or 3, with the proviso that not more than two T's are other than alkyl, and with the further proviso that the various T's may be the same or different, there are prepared the corresponding dimethyl-3,3-dimethyl-2-oxo-4-(substituted phenyl)butylphosphonates. For example, there is prepared by this procedure dimethyl 3,3-dimethyl-2-oxo-4-(p-fluorophenyl)-butylphosphonate.

Further, following the procedure of Example 1, but using in place of the isobutyric acid of Example 1, part A, propionic acid, there is prepared dimethyl 3-methyl-2-oxo-4-phenylbutylphosphonate. Following the procedure of Example 1, but using the substituted benzyl chlorides described above in place of benzyl chloride and propionic acid in place of isobutyric acid there are prepared the various dimethyl 3-methyl-2-oxo-4-(substituted phenyl)butylphosphonates wherein the phenyl substitution is as described above.

Further, following the procedure of Example 1, but using acetic acid in place of isobutyric acid as used in Example 1, part A, there is prepared dimethyl-2-oxo-4-phenylbutylphosphonate. Using acetic acid in combination with the various substituted benzyl chlorides described above according to the procedure of Example 1, there are prepared the various dimethyl 2-oxo-4-(substitutedphenyl)-butyl phosphonates, wherein the phenyl substitution is as described above.

Following the procedure of Example 1, but using 2,2-difluoroacetic acid in place of isobutyric acid as used in part A of Example 1, there is prepared dimethyl 3,3-difluoro-2-oxo-4-phenylbutylphosphonate. Further, following the procedure of Example 1, but using 2,2-difluoro acetic acid in combination with substituted benzyl chlorides described above, there are prepared the corresponding dimethyl 3,3-difluoro-2-oxo-4-(substituted)phenylbutylphosphonate, wherein the phenyl substitution is as described above.

Further, following the procedure of Example 1, but using 2-fluoro acetic acid in place of isobutyric acid there is prepared dimethyl 3-fluoro-2-oxo-4-phenyl-butylphosphonate.

Using 2-fluoro acetic acid and the various substituted benzyl chlorides described above according to the procedure of Example 1, there are prepared the various dimethyl 3-fluoro-2-oxo-4-(substituted)phenylbutyl phosphonates, wherein the phenyl substitution is as described above.

EXAMPLE 2

Triphenylphosphonium salt of 2,2-difluoro-5-bromopentanoic acid, $Br(C_6H_5)_3P—(CH_2)_3—CF_2—COOH$.

A. Methyl furoate (50.4 g.) is dissolved in 180 ml. of methanol Thereafter 1 g. of 5 percent palladium-on-charcoal is added. This mixture is then hydrogenated at 1 to 3 atmospheres. After 45 hours 0.79 moles of hydrogen are consumed. The black mixture is then filtered through Celite using 50 ml. of methanol to wash the reaction flask and filter. Evaporation of the filtrate under reduced pressure at 40°-45° C. bath temperature yields 51 g. of a yellow oil which is thereafter distilled, collecting that fraction boiling at 32°-35° C. Thereby, methyl tetrahydrofuroate (46.7 g.) is prepared.

B. Anhydrous hydrobromic acid is bubbled through 50 ml. of acetic anhydride with cooling until a specific gravity of 1.3 is obtained. This reagent is then added to 25 g. of the reaction product of step A of this example, with exclusion of moisture while cooling and stirring. Stirring in the ice water bath is continued for 15 min.; thereafter, the mixture is allowed to stand at room temperature overnight. The reaction mixture is then poured into 600 g. of crushed ice and water with stirring and extracted with diethyl ether. The ether extract is washed with aqueous sodium hydroxide, dried over sodium sulfate, filtered, and thereafter evaporated under reduced pressure to yield 38 g. of a pale yellow oil, which is thereafter distilled under high vacuum, yielding 31.6 g. of methyl 2-acetoxy-5-bromopentanoate.

C. To a solution of 60 g. of the reaction product of part B of this example in 200 ml. of methanol is added 100 ml. of methanol, which is saturated with hydrobromic acid at 0° C. and 1.3 specific gravity before the addition. The reaction mixture is then allowed to stand at room temperature overnight. The solvent is thereafter evaporated under reduced pressure at 35° C. bath temperature and 400 ml. of toluene is thereafter added. The solvent is again evaporated. This residue is then dissolved in 2 l. of ethyl acetate, washed with 5 percent aqueous sodium hydroxide solution and sodium chloride solution before being dried over sodium sulfate. Filtration and evaporation of the solvent under reduced pressure at 45° C. yields 42 g. of oil which is distilled under high vacuum, yielding 28.8 g. of methyl 2-hydroxy-5-bromopentanoate.

D. To a solution of 34.4 g. of the reaction product of part C of this example and 400 ml. of acetone is added with stirring and cooling 75 ml. of Jones reagent (26.73 g. of $CrO_3$ in 23 ml. of concentrated sulfuric acid, diluted to 100 ml. with water) at such a rate that the reaction temperature is maintained between 30° and 40° C. The reaction is complete in approximately 20 min. Thereafter the reaction mixture is stirred for 1.5 hr. Thereafter 150 ml. of isopropyl alcohol are slowly added with stirring during 30 min. The reaction mixture is then diluted with 1.8 l. of water and extracted with 2.4 l. of methylene chloride. These extracts are washed with brine and dried with sodium sulfate. Filtration and evaporation of the solvent under reduced pressure yields 30.8 g. of a pale yellow oil, containing methyl 2-oxo-5-bromopentanoate. This oil is used in the following steps of this example without further purification.

E. With the exclusion of moisture under a nitrogen atmosphere 195 ml. of $MoF_6.BF_3$ (Mathey, et al., Tet. Lett. 27, 2965; 1971) is cooled in a dry-ice acetone bath. A solution of 30.8 g. of the reaction product of step D of this example and 40 ml. of methylene chloride is added dropwise with stirring over a period of 15 min. The reaction temperature is maintained between −35° and −45° C. Stirring the dry ice acetone bath is continued for one hour, the cooling bath thereafter is removed, and the reaction mixture thereafter diluted with 200 ml. of methylene chloride and 400 ml. of water. The organic and aqueous layers are separated, the aqueous layer being extracted with methylene chloride and the combined methylene chloride extracts washed with 250 ml. of water, 250 ml. of 5 percent aqueous potassium bicarbonate, 250 ml. of brine, and thereafter dried over sodium sulfate. Filtration and evaporation of the solvent yields 31.1 g. of a dark brown oil, which when distilled under high vacuum yields methyl 2,2-difluoro-5-bromopentanoate (14 g.).

F. The reaction product of part E of this example (28 g.) is stirred in 175 ml. of aqueous hydrobromic acid (specific gravity 1.71) for 3 hours at room temperature. The reaction mixture is then cooled in an ice bath, and diluted with 1300 ml. of diethyl ether. The organic and aqueous layers are separated and the aqueous layer is extracted with diethyl ether. The combined ethereal solutions are washed with water and the aqueous solutions are backwashed with 400 ml. of ether and the combined ethereal solutions is then dried over sodium sulfate. Filtration and evaporation of the solvent yields 27.7 g. of a pale yellow oil, 2,2-difluoro-5-bromopentanoic acid, which is used in the following step of this example without further purification.

G. A mixture of 15.2 g. of the reaction product of part F of this example, 80 ml. of acetonitrile and 22 g. of triphenylphosphine are heated to reflux with stirring for 30 hours. The reaction mixture is then heated to 110° C., diluted with 160 ml. of toluene, and the mixture is allowed to cool slowly at room temperature for 12 hours with stirring. The reaction mixture is then stored at 5° C. for 24 hours. A precipitate is collected, washed with 50 ml. of toluene, and dried under vacuum at room temperature. 20.9 g. of the title compound of this example is thereby obtained.

EXAMPLE 3

(6-Carboxyhexyl)triphenylphosphonium bromide.

A mixture of 63.6 g. of 7-bromoheptanoic acid, 80 g. of triphenylphosphine, and 30 ml. of acetonitrile, is refluxed for 68 hours. Thereafter 200 ml. of acetonitrile is removed by distillation. After the remaining solution is cooled to room temperature, 30 ml. of benzene is added with stirring. The mixture is then allowed to stand for 12 hours. A solid separates which is collected by filtration, yielding 134.1 g. of product, melting point 185°–187° C.

Following the procedure of Example 3, but using 3-bromopropionic acid, 4-bromobutanoic acid, 5-bromopentanoic acid, or 6-bromohexanoic acid, in place of 7-bromoheptanoic acid, there are prepared the corresponding (ω-carboxyalkyl)tripehenylphosphonium bromides.

EXAMPLE 4

3α-Benzoyloxy-5α-hydroxy-2β-(2-chloro-3-oxo-4,4-dimethyl-trans-1-octenyl)-1α-cyclopentaneacetic acid, γ lactone (the 3-ketone of Formula XXIII: $R_7$ is n-butyl, $R_{16}$ is benzoyloxy, $R_3$ and $R_4$ of the $L_1$ moiety are methyl, and $Y_1$ is trans-CH=C(Cl)—).

Refer to Chart A.

A. A solution of 24.3 g. of thallous ethoxide in 125 ml. of dry benzene is cooled in an ice bath, and thereafter a solution of 25.3 g. of methyl 3,3-dimethyl-2-oxoheptylphosphonate in 75 ml. of benzene is added and thereafter rinsed with 50 ml. of benzene. The solution is stirred for 30 min. at 5° C. and thereafter 22.1 g. of crystalline 3α-benzoyloxy-5α-hydroxy-2β-carboxaldehyde-1α-cyclopentaneacetic acid, γ lactone is added rapidly. This reaction mixture is then stirred for 13 hours at ambient temperature yielding a brown solution of pH 9–10. Acetic acid (6 ml.) is added and the mixture is transferred to a beaker with 600 ml. of diethyl ether. Celite and 500 ml. of water is added, followed by the addtion of 30 ml. (about 33 g.) of saturated potassium iodide. The mixture (containing a bright yellow precipitate of thallous iodide) is stirred for about 45 min., and thereafter filtered through a bed of Celite. The organic layer is then washed with water, aqueous potassium bicarbonate, and brine. Thereafter the resulting mixture is dried over magnesium sulfate and evaporated at reduced pressure, yielding 33.6 g. of an oil, which is then chromatographed on 600 g. of silica gel packed in 20 percent ethyl acetate in cyclohexane. Elution, collecting 500 ml. fractions, with 2 l. of 20 percent, 2 l. of 25 percent, and 4 l. of 30 percent ethyl acetate in cyclohexane yields 20.3 g. of crude product, which upon recrystallization from 240 ml. of diethyl ether in pentane (2:1) yields 3α-benzoyloxy-5α-hydroxy-2β-(3-oxo-4,4-dimethyl-trans-1- octenyl)-1α-cyclopentaneacetic acid, γ lactone.

Alternatively this product is prepared by adding 3α-benzoyloxy-2β-carboxaldehyde-5α-hydroxy-1α-cyclopentaneacetic acid γ lactone (3 g.) in 30 ml. of dichloromethane to a solution of dimethyl 2-oxo-3,3-dimethylheptylphosphonate (6.69 g.) and sodium hydride (1.35 g.) in 15 ml. of tetrahydrofuran. The resulting reaction mixture is then stirred for 2 hours at about 25° C., acidified with acetic acid, and concentrated under reduced pressure. The residue is partitioned betwen dichloromethane and water, and the organic phase is concentrated. The residue is chromatographed on silica gel, eluting with ethyl acetate in Skellysolve B (1:1).

B. A solution of the reaction product of part A of this example (1.15 g.) in dioxane (35 ml.) is treated with N-chlorosuccinimide (9.7 g.) and stirred for 6 days. The resulting solution is then diluted with methylene chloride, washed with saline and a sodium sulfate solution, dried, and evaporated to yield a viscous residue. The residue in benzene is subjected to silica gel chromatography, eluting with hexane and ethyl acetate (9:1) whereupon pure 3α-benzoyloxy-5α-hydroxy-2β-(1,2-dichloro-3-oxo-4,4-dimethyloctyl)-1α-cyclopentaneacetic acid γ lactone is recovered (as a mixture of isomers). Thereafter the dichlorides so obtained are diluted with pyridine (20 ml.) and heated at 100° C. for 4.5 hours. The resulting solution is then diluted with diethyl ether and washed with ice cold dilute hydrochloric acid and brine. The resulting mixture is then dried and subject to silica gel chromatography, eluting with hexane and ethyl acetate (9:1), yielding 0.765 g. of pure product. NMR absorptions are observed at 0.85, 1.22, 1.0–1.9, 1.9–3.5, 4.8–5.1, 5.35, 6.28, 7.2–7.6, and 7.8–8.1 δ. The mass spectrum shows peaks at 432, 396, 376, 378, 254, and 256.

Alternatively, the reaction product of part A above (0.190 g.) in dry pyridine (5 ml.) at 0° C. is treated with freshly distilled sulfuryl chloride (0.386 g.) and the reaction is maintained for 5 hours. Thereafter additional sulfuryl chloride (0.667 g.) and pyridine (5 ml.) is added and the reaction continued for 12 hours for ambient temperature. A resulting dark solution is then diluted with methylene chloride, washed with ice cold phosphoric acid, sodium bicarbonate, dried, and evaporated. The residue is chromatographed on silica gel eluting with hexane and ethyl acetate (9:1). Pure product identical with that recovered in the preceding paragraph is obtained.

Following the procedure of Example 4, but using in place of 3α-benzoyloxy-5α-hydroxy-2β-carboxaldehyde-1α-cyclopentaneacetic acid γ lactone; 5α-hydroxy-2β-carboxaldehyde-1α-cyclopentaneacetic acid γ lactone, there is obtained 5α-hydroxy-2β-(2-chloro-3-oxo-4,4-dimethyl-trans-1-octenyl)-1α-cyclopentaneacetic acid γ lactone.

Further, following the procedure of Example 4, but using in place of dimethyl 2-oxo-3,3-dimethylheptylphosphonate, any of the various dimethyl phosphonates described hereinabove there are prepared the corresponding 3α-benzoyloxy-5α-hydroxy-1αl -cyclopentaneacetic acid γ lactones or 5α-hydroxy-1α-cyclopentane-acetic acid γ lactones with a 2β-(2-chloro-3-oxo-trans-1-alkenyl)-substituent, optionally substituted, as follows: 4,4-difluorohexenyl; 4,4-difluoroheptenyl; 4,4-difluorooctenyl; 4,4-difluorononenyl; 4,4-difluorodecenyl; 4-fluorohexenyl; 4-fluoroheptenyl; 4-fluorooctenyl; 4-fluorononenyl; 4-fluorodecenyl; 4,4-dimethylhexenyl; 4,4-dimethylheptenyl; 4,4-dimethylnonenyl; 4,4-dimethyldecenyl; 4-methylhexenyl; 4-methylheptenyl; 4-methyloctenyl; 4-methylnonenyl; 4-methyldecenyl; hexenyl; heptenyl; octenyl; nonenyl; decenyl; 5-phenylpentenyl; 5-(m-trifluoromethylphenyl)-pentenyl; 5-(m-fluorophenyl)-pentenyl; 5-(m-chlorophenyl)-pentenyl; 5-(p-trifluoromethylphenyl)-pentenyl; 5-(p-fluorophenyl)-pentenyl; 5-(p-chlorophenyl)-pentenyl; 4-methyl-5-phenylpentenyl; 4-methyl-5-(m-trifluoromethylphenyl)pentenyl; 4-methyl-5-(m-fluorophenyl)-pentenyl; 4-methyl-5-(p-trifluoromethylphenyl)-pentenyl; 4-methyl-5-(p-fluorophenyl)-pentenyl; 4-methyl-5-(p- chlorophenyl)-pentenyl; 4,4-dimethyl-5-(m-trifluoromethylphenyl)-pentenyl; 4,4-dimethyl-5-(m-fluorophenyl)-pentenyl; 4,4-difluoro-5-)m-chlorophenyl)-pentenyl; 4,4-dimethyl-5-(p-trifluoromethylphenyl)-pentenyl; 4,4-dimethyl-5-(p-fluorophenyl)-pentenyl; 4,4-dimethyl-5-(p-chlorophenyl)-pentenyl; 4-fluoro-5-phenylpentenyl; 4-fluoro-5-(m-trifluoromethylphenyl)-pentenyl; 4-fluoro-5-(m-fluorophenyl)-pentenyl; 4 -fluoro-5-(m-chlorophenyl)-pentenyl; 4-fluoro-5-(p-trifluoromethyl-phenyl)-pentenyl; 4-fluoro-5-(p-fluorophenyl)-pentenyl; 4-fluoro-5-(p-chlorophenyl)-pentenyl; 4,4-difluoro-5-phenylpentenyl; 4,4-difluoro-5-(m-trifluoromethylphenyl)-pentenyl; 4,4-difluoro-5-(m-fluorophenyl)-pentenyl; 4,4-difluoro-5-(m-chlorophenyl)-pentenyl; 4,4-difluoro-5-(p-trifluoromethylphenyl)-pentenyl; 4,4-difluoro-5-(p-fluorophenyl)-pentenyl; 4,4-difluoro-5-(p-chlorophenyl)-pentenyl; 4-phenoxybutenyl; 4-(m-trifluoromethylphenoxy)-butenyl; 4-(p-fluorophenoxy)-butenyl; 4-(m-chlorophenoxy)-butenyl; 4-(m-trifluoromethylphenoxy)-butenyl; 4-(p-fluorophenoxy)-butenyl; 4-(p-chlorophenoxy)-butenyl; 4-methyl-4-phenoxybutenyl; 4-methyl-4-(m-trifluoromethylphenoxy)-butenyl; 4-methyl-4-(m-fluorophenoxy)-butenyl; 4-methyl-4-(m-chlorophenoxy)-butenyl; 4-methyl-4-(p-trifluoromethylphenoxy)-butenyl; 4-methyl-4-(p-fluorophenoxy)-butenyl; 4-methyl-4-(p-chlorophenoxy)-butenyl; 4,4-dimethyl-4-phenoxybutenyl; 4,4-dimethyl-4-(trifluoromethylphenoxy)-butenyl; 4,4dimethyl-4-(m-fluorophenoxy)-butenyl; 4,4-dimethyl-4-(m-chlorophenoxy)-butenyl; 4,4-dimethyl-4-(p-trifluoromethylphenoxy)-butenyl; 4,4-dimethyl-4-(p-fluorophenoxy)-butenyl; 4,4-dimethyl-4-(p-chlorophenoxy)-butenyl; and the like.

PGF$_{60}$, PGE, PGF$_{62}$, and PGA analogs described herein are are prepared from the 3-ketone of formula XXIII wherein the C-3 position of the cyclopentane ring is substituted by a benzoyloxy moiety as described above (Example 4).

Likewise, intermediates useful in preparing 11-deoxy-PGF$_{60}$, 11-deoxy-PGE, and 11-deoxy-PGF$_{62}$-type compounds are those 3-ketones of formula XXIII prepared following Example 4 except the formula XXI starting material employed is a 3-unsubstituted lactone; that is 5α-hydroxy-2β-carboxaldehyde-1α-cyclopentaneacetic acid γ lactone. Accordingly there are prepared 5β-hydroxy-1α-cyclopentaneacetic acid γ lactones with the various 2β-side chains described following Example 4 which are useful in the same manner as the 3α-benzoyloxy compounds in the procedures of succeeding examples for preparing the 11-deoxy-PGF$_{60}$-, PGE-, or PGF$_{62}$-type compounds corresponding to the PGF$_a$-, PGE-, and PGF$_{62}$-type compounds therein prepared.

EXAMPLE 5

3α-Benzoyloxy-5α-hydroxy-2β-[2-chloro-(3R)-3-hydroxy-4,4-dimethyl-trans-1-octenyl]-1α-cyclopentaneacetic acid γ lactone (Formula XXIII: R$_3$ and R$_4$ of the L$_1$ moiety are methyl, M$_5$ is

R$_7$ is n-pentyl, R$_{16}$ is benzoyloxy, and Y$_1$ is trans-CH=C(Cl)) or its (3S)-hydroxy epimer.

Sodium borohydride (0.92 g.) is slowly added to a stirred suspension of 2.1 g. of anhydrous zinc chloride in 45 ml. of dimethyl ether in ethylene glycol (glyme) with ice bath cooling. The mixture is stirred for 20 hours at ambient temperature and thereafter cooled to −18° C. A solution of 0.76 g. of 3α-benzoyloxy-5α-hydroxy-2β-(2-chloro-3-oxo-4,4-dimethyl-trans-1-octenyl)-1α-cyclopentaneacetic acid γ lactone (prepared according to Example 4 ) in 12 ml. of glyme is added over a period of 20 minutes. Stirring is continued for 24 hours at −20° C. and thereafter 40 ml. of water is cautiously added. The reaction mixture is warmed to room temperature, diluted with ethyl acetate, and washed twice with brine. The aqueous layers are extracted with ethyl acetate. The combined organic extracts are dried over sodium sulfate and evaporated to yield crude product, which when chromatographed on 12 g. of silica gel eluting with hexane and in ethyl acetate (3:1) yields the epimerically pure title product.

The 3R epimer exhibits ultraviolet absorpitons at $\lambda_{max.}$ equals 229.5 nm. (E 13,550). The mass spectrum shows absorption at 337, 336, 335, 217, 216, 215, 214, and 213. NMR absorptions in CDCl$_3$ are observed at 0.85, 0.90, 0.80–1.0, 1.0–1.5, 1.9–3.0, 3.0–3.6, 4.0, 4.7–5.5, 5.65, 7.2–7.7, and 7.8–8.2 δ.

The 3S epimer exhibits NMR absorptions in CDCl$_3$ at 0.86, 0.90, 0.8–1.0, 1.0–1.5, 2.1–3.0, 3.0–3.8, 4.0, 7.1–7.7, and 7.8–8.2 δ.

Following the procedure of Example 5, but using in place of the 3α-benzoyloxy-5α-hydroxy-2β-(2-chloro-3-oxo-4,4-dimethyl-trans-1-octenyl)-1α-cyclopentaneacetic acid γ lactone starting material employed therein, the various 3α-benzoyloxy-5α-hydroxy-2γ-(2-chloro-3-oxo-trans-1-alkenyl, or substituted alkenyl)-1α-cyclopentaneacetic acid γ lactones there are prepared the corresponding (3R)' or (3S)-hydroxy products.

Following the procedure of Example 5, but using in place of the 3α-benzoyloxy-5α-hydroxy-2β-(2-chloro-3-oxo-4,4-dimethyl-trans-1-octenyl)-1α-cyclopentaneacetic acid γ lactone used therein, 5α-hydroxy-2γ-(2-chloro-3-oxotrans-1-alkenyl or substituted alkenyl)-1α-cyclopentaneacetic acid γ lactones described following Example 4, there are prepared the corresponding (3R)' or (3S)-hydroxy products. For example, there are obtained the above 3α-benzoyloxy-5α-hydroxy- or 5α-hydroxy-1α-cyclopentaneacetic acid γ lactones wherein the 2γ-side chain in either the (3R) or (3S) form consists of 2-chloro-3-hydroxy-trans-1-hexenyl;
2-chloro-3-hydroxy-trans-1-heptenyl;
2-chloro-3-hydroxy-trans-1-octenyl;
2-chloro-3-hydroxy-trans-1-nonenyl;
2-chloro-3-hydroxy-trans-1-decenyl;
2-chloro-3-hydroxy-4-methyl-trans-1-octenyl;
2-chloro-3-hydroxy-4-fluoro-trans-1-octenyl;
2chloro-3-hydroxy-4,4-difluoro-trans-1-octenyl;
2-chloro-3-hydroxy-5-phenyl-trans-1-pentenyl;
2-chloro-3-hydroxy-5-(p-fluorophenyl)-trans-1-pentenyl;
2-chloro-3-hydroxy-5-(m-chlorophenyl)-trans-1-pentenyl;
2-chloro-3-hydroxy-5-(m-trifluoromethylphenyl)-trans-1-pentenyl;
2-chloro-3-hydroxy-4,4-dimethyl-5-phenyl-trans-1-pentenyl;
2-chloro-3-hydroxy-4,4-dimethyl-5-(p-fluorophenyl)-trans-1-pentenyl;
2-chloro-3-hydroxy-4,4-dimethyl-5-(m-chlorophenyl)-trans-1-pentenyl;

2-chloro-3-hydroxy-4,4-dimethyl-5-(m-trifluoromethylphenyl)-trans-1-pentenyl;
2-chloro-3-hydroxy-4,4-difluoro-5-phenyl-trans-1-pentenyl;
2-chloro-3-hydroxy-4,4-difluoro-5-(p-fluorophenyl)-trans-1-pentenyl;
2-chloro-3-hydroxy-4,4-difluoro-5-(m-chlorophenyl)-trans-1-pentenyl;
2-chloro-3-hydroxy-4,4-difluoro-5-(m-trifluoromethylphenyl)-trans-1-pentenyl;
2-chloro-3-hydroxy-4-phenoxy-trans-1-butenyl;
2-chloro-3-hydroxy-4-(p-fluorophenoxy)-trans-1-butenyl;
2-chloro-3-hydroxy-4-(m-chlorophenoxy)-trans-1-butenyl;
2 -chloro-3-hydroxy-4-(m-trifluoromethylphenoxy)-trans-1-butenyl;
2-chloro-3-hydroxy-4,4-dimethyl-4-phenoxy-trans-1-butenyl;
2-chloro-3-hydroxy-4,4-dimethyl-4-(p-fluorophenoxy)-trans-1-butenyl;
2-chloro-3-hydroxy-4,4-dimethyl-4-(m-chlorophenoxy)-trans-1-butenyl;
2-chloro-3-hydroxy-4,4-dimethyl-4-(m-trifluoromethylphenoxy)-trans-1-butenyl; and the like.

EXAMPLE 7

3α-Benzoyloxy-5α-hydroxy-2β-[2-chloro-(3S)-3-hydroxy-3-methyl-trans-1-trans-1-octenyl]-1α-cyclopentaneacetic acid γ lactone (Formula XXIII as in Example 6 except M$_5$ is

Refer to Chart A.

A solution of 18 g. of 3α-benzoyloxy-5α-hydroxy-2β-(2-chloro-3-oxo-trans-1-octenyl)-1α-cyclopentaneacetic acid γ lactone in 890 ml. of dry benzene is cooled to 9° C. under a nitrogen atmosphere. A toluene solution of trimethylaluminum (60 ml.) is added over a period of 4 min. to the resulting mixture. This mixture is then stirred for 1.5 hours at 20°–25° C. then cooled to 10° C. Thereupon 370 ml. of saturated ammonium chloride is slowly added at such a rate so as to maintain the reaction mixture at ambient temperature. After 0.5 hours the reaction mixture is diluted with ethyl acetate and water and filtered, the filter cake being washed with the ethyl acetate-water solvent. The aqueous layer is extracted with ethyl acetate and the combined organic extracts are washed with brine, dried over magnesium sulfate, and evaporated to yield crude product, which is chromatographed on one kg. of silica gel packed in 10 percent ethyl acetate and Skellysolve B. Elution with 10 to 16 percent ethyl acetate in Skellysolve B (18 l.), 28 percent ethyl acetate in Skellysolve B (8 l.) yields pure title compound or pure (3R)-epimer.

Omitting the chromatographic separation described above, the (3RS)-epimeric mixture obtained on trimethylaluminum alkylation are separated in high yield as prostaglandin-type products.

Following the procedure of Example 7, but using in place of the 2-chloro-3-oxo lactone starting material therein, the various lactones described following Examples 4, there are obtained 2-chloro-3-hydroxy-3-methyl products corresponding to each of the 2-chloro-3-hydroxy products of Example 5.

EXAMPLE 8

3α,5α-dihydroxy-2β-[2-chloro-(3S)-3-hydroxy-4,4-dimethyl-trans-1-octenyl]-1α-cyclopentaneacetaldehyde, γlactol, bis-tetrahydropyranyl ether (Formula XXVI : R$_3$ and R$_4$ of the L$_1$ moiety are methyl, M$_6$ is

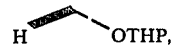

R$_7$ is n-butyl, R$_{18}$ is tetrahydropyran-2-yloxy, and Y$_1$ is trans-CH=C(Cl)—) and its (3R)-epimer.

Refer to Chart A.

A. A solution of 100 mg. of the reaction product of Example 5 in 20 ml. of methanol is purged with nitrogen. Thereafter, potassium carbonate (30 mg.) is added and the resulting mixture is stirred at ambient temperature until thin layer chromatographic analysis shows the solvolysis to be complete (about 12 hours). The solution is then diluted with ice water and neutralized with cold, dilute phosphoric acid. The resulting mixture is then dried and evaporated under reduced pressure. The residue is then chromatographed using silica gel eluting with hexane and ethylacetate (3:2). Accordingly, 40 mg. of the deacylated lactone are prepared. NMR absorptions are observed at 0.92, 0.95, 1.1–1.6, 2.0–3.3, 4.02, 4.8–5.2, 5.57, and 5.66 δ.

B. A solution of 0.39 g. of the reaction product of part A above, in 25 ml. of methylene chloride (containing 1.2 ml. of dihydropyran and 1.2 mg. of a saturated solution of pyridine in methylene chloride) is allowed to stand for one hour at ambient temperature. Additional dihydropyran (1.2 ml.) is added and the reaction continued for 36 hours. The reaction mixture is then washed with water, aqueous sodium bicarbonate, dried, and evaporated, yielding an oil (0.371 g.), the bis-tetrahydropyranyl lactone corresponding to the lactone reaction product of part A above. NMR absorptions are observed at 0.6–1.05, 1.05–1.4, 1.4–1.9, 1.9–3.0, 3.0–4.3, 4.0, 4.3–5.2, and 5.48 δ.

C. A solution of the reaction product of part B above (0.39 g.) in 10 ml. of toluene is cooled to −70° C. and thereafter 10 ml. of 10 percent diisobutylaluminum hydride (1.64 mmoles) in toluene (10 ml.) is slowly added. The reaction mixture is then stirred at −70° C. until thin layer chromatographic analysis indicates that the reduction is complete (about 10 min.). Thereafter the cooling bath is removed and 9 ml. of a mixture of tetrahydrofuran and water (3:1) is added slowly. The reaction mixture is then stirred and allowed to warm to room temperature, and is then filtered through a cellulose bed. The filter cake is rinsed with benzene, combined organic extracts are then dried and evaporated to yield 0.40 g. of the title compound. NMR absorptions are observed at 0.7–1.05, 1.05–1.35, 1.35–1.9, 1.9–2.8, 2.8–4.2, 4.00, and 5.60 δ.

Following the procedure of Example 8, the 3α-benzoyloxy-5-hydroxy or 5-hydroxy lactones described in and following Examples 5 and 7 are transformed into corresponding γ-lactols.

Following the procedure of Example 8 there is prepared from (3S) starting material, respectively:

1. 3α,5α-Dihydroxy-2β-[2-chloro-(3S)-3-hydroxy-4,4-dimethyl-trans-1-octenyl]-1α-cyclopentaneacetic γ lactone. NMR absorptions are observed at 0.92, 1.1–1.7, 1.8–3.2, 3.2–3.5, 4.0, 4.8–5.2, and 5.66 δ. The mass spectrum shows peaks at 312, 233, 232, 231, 216, and 215.

2. 3α,5α-Dihydroxy-2β-[2-chloro-(3S)-3-hydroxy-4,4-dimethyl-trans-1-octenyl]-1α-cyclopentaneacetic acid γlactone bis-tetrahydropyranyl ether. NMR absorptions are observed at 0.6–1.05, 1.05–1.4, 1.4–2.0, 2.0–3.0, 3.0–4.4, 4.00, 4.4–5.7, and 5.48 δ.

3. 3α,5α-Dihydroxy-2β[2-chloro-(3S)-3-hydroxy-4,4-dimethyl-trans-1-octenyl]-1α-cyclopentane acetaldehyde γlactol bis-tetrahydropyranyl ether. NMR absorptions are observed at 0.6–1.1, 1.35–1.85, 1.85–3.0, 3.2–4.3, 4.00, 4.3–5.1, and 5.58 δ.

Further following the procedure of Example 8, but using the various lactones described following Examples 5 and 7 wherein $R_{16}$ is hydrogen, there are prepared the corresponding 5α-hydroxy-1α-cyclopentaneacetaldehyde γlactol bis-tetrahydropyranyl ethers.

Further following the procedure of Example 8, but using as starting material the various lactols described following Example 5 and in and following Example 7, wherein $R_{16}$ is benzoyloxy, there are prepared the corresponding 3α,5α-dihydroxy-1α-cyclopentaneacetaldehyde γ lactol bis-tetrahydropyranyl ethers.

EXAMPLE 10

5-Oxa-14-chloro-PGF$_{1\alpha}$, methyl ester, 11,15-bis-(tetrahydropyranyl) ether (Formula XXXVI: g is one, $R_3$ and $R_4$ of the $L_1$ moiety are hydrogen, $M_6$ is

$R_1$ is methyl, $R_7$ is n-butyl, $R_{18}$ is tetrahydropyranyloxy, and $Y_1$ is trans-CH=C(Cl)—) or its 15-epimer.

Refer to Chart A.

A. A mixture of lactol starting material of Example 9 (6.3 g.) and 50 ml. of 95 percent ethanol is treated at 0° C. with stirring with a solution of sodium borohydride in 10 ml. of water (added over a period of one minute). The resulting mixture is then stirred at 0° C. for 10 minutes and then shaken with 10 ml. of water, 250 ml. of ethyl acetate, and 150 ml. of brine. The organic phase is then washed with brine, dried, and concentrated under reduced pressure to yield 2-decarboxy-2-hydroxymethyl-2,3,4,5,6-pentanor-14-chloro-PGF$_{1\alpha}$, 11,15-bis-tetrahydropyranyl ether.

B. A solution of potassium tert-butoxide (1.77 g.) in 30 ml. of tetrahydrofuran is mixed at 0° C., with stirring, with a solution of the reaction product of part A (5.8 g.) in 30 ml. of tetrahydrofuran. The resulting mixture is then stirred at 0° C. for 5 minutes and thereafter 5 ml. of trimethyl ortho-4-bromobutyrate is added. Stirring is continued at 0° C. for 2 hours and at about 25° C. for 16 hours. To this mixture is added 30 ml. of dimethylformamide and 0.5 g. of potassium-t-butoxide. The resulting mixture is then stirred for 20 hours. Some of the solvent is then removed under reduced pressure and the residue is then shaken with water and diethyl ether and dichloro methane (3:1). The organic phase is then washed with water and brine, dried, and concentrated. The residue, containing the ortho ester, is dissolved in 6 ml. of methanol at 0° C. and treated with 15 ml. of cold water containing 2 drops of concentrated hydrochloric acid. The resulting mixture is then stirred at 0° C. for 5 minutes, shaken with 200 ml. of diethyl ether, 50 ml. of dichloromethane, and 200 ml. of brine. The organic phase is then washed with brine, dried, and concentrated under reduced pressure. The residue is subjected to silica gel chromatography, yielding the title compounds.

C. Trimethylortho-4-butyrate is prepared as follows:
Refer to S. M. McEldian, et al., Journal of the American Chemical Society 64, 1825 (1942). A mixture of 4-bromobutyronitrile (74 g.), 21 ml. of methanol, and 150 ml. of diethyl ether is treated at 0° C. with stirring, with hydrogen bromide (40 g.). The mixture is then stirred for an additional 4 hours at 0° C. and 100 ml. of hexane is added. The precipitated imino ester hydrobromide is separated from the liquid by filtration and washed with 400 ml. of diethyl ether in hexane (1:1). The imino ester salt is treated in 250 ml. of diethyl ether with 150 ml. of methanol and 25 ml. of methyl orthoformate, with stirring, at about 25° C. for 24 hours. The resulting mixture is then cooled to about 10° C. and the organic solution is separated from the ammonium bromide thereby formed. Diethyl ether (100 ml.) is then added. The resulting solution is then immediately and quickly washed with an ice cold solution prepared from potassium carbonate (20 g.) and 300 ml. of brine. The organic phase is washed with brine, treated with 3 drops of pyridine, and dried over anhydrous magnesium sulfate. The solution is then concentrated under reduced pressure, diluted with 150 ml. of benzene, and again concentrated. The residue is then distilled to yield the title ortho-4-bromobutyrate.

Following the procedure of part C of Example 10, but using 5-bromo pentanonitrile or 6-bromo hexanonitrile there is prepared trimethylortho-5-pentanoate or trimethylortho-6-bromo hexanoate.

Following the procedure of Example 10, but using the corresponding (3S) lactone, there is obtained the corresponding 15-epi-14-chloro-PGF$_{1\alpha}$-type product.

Following the procedure of Example 10, but using any of the various lactols described following Example 8, there is prepared the corresponding 5-oxa-14-chloro-PGF$_{1\alpha}$-type product. For those lactols wherein the C-3position of the cyclopentane ring is unsubstituted ($R_{18}$ is hydrogen), the corresponding 11-deoxy-PGF$_{1\alpha}$-type product produced is not etherified at the C-11 position. For those lactols described following Example 8, wherein the C-3 position of the side chain contains a methoxy group, the corresponding 3-oxa-14-chloro-13-PGF$_{1\alpha}$-type product contains no tetrahydropyranyl ether at the C-15 position.

Further, following the procedure of Example 10, but using trimethylortho-5-bromopentanoate or trimethylortho-6-bromohexanoate there is prepared the corresponding 5-oxa-14-chloro-PGF$_{1\alpha}$-type product wherein g is 3 or 4. Likewise using the various lactols described following Example 8, corresponding 2a-homo or 2a,2b-dihomo products are obtained.

EXAMPLE 12 cis-4,5-Didehydro-14-14-chloro-PGF$_{1\alpha}$11,15-bis-(tetrahydropyranyl)ether (Formula XXXIII: g is one, n is two, $R_2$ is hydrogen $R_3$ and $R_4$ of the $L_1$ moiety are hydrogen, $M_6$ is

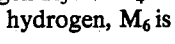

$R_1$ is hydrogen, $R_7$ is n-butyl, $R_{18}$ is tetrahydropyranyloxy, and $Y_1$ is trans-CH=C(Cl)—).

Refer to Chart A.

A. A suspension of methoxymethyltriphenylphosphonium chloride (32.4 g.) in 150 ml. of tetrahydrofuran is cooled to −15° C. To the suspension is added 69.4 ml. of n-butyllithium in hexane (1.6 molar) in 45 ml. of tetrahydrofuran. After 30 minutes there is added a solution of 3α,5α-dihydroxy-2β-[2-chloro-(3S)-3-hydroxy-trans-1-octenyl]-1α-cyclopentaneacetaldehyde γ lactol bis-(tetrahydropyranyl)ether, (10 g.), in 90 ml. of tetrahydrofuran. The mixture is stirred for 1.5 hours while warming to 25° C. The resulting solution is thereafter concentrated under reduced pressure. The residue is partitioned between dichloromethane and water, the organic phase being dried and concentrated. This dry residue is then subjected to chromatography over silica gel eluting with cyclohexane and ethyl acetate (2:1). Those fractions as shown by thin layer chromatography to contain pure formula XXVIII product are combined.

B. The reaction product of part A above in 20 ml. of tetrahydrofuran is hydrolyzed with 50 ml. of 66 percent aqueous acetic acid at about 57° C. for 2.5 hours. The resulting mixture is then concentrated under reduced pressure. Toluene is added to the residue and the solution is again concentrated. Finally the residue is subjected to chromatography on silica gel, eluting with chloroform and methanol (6:1). The title compound is thereby obtained by combining and concentrating fractions as shown by thin layer chromatography to contain pure product. Accordingly, there is obtained the corresponding formula XXVIII δ-lactol.

C. Silver oxide is prepared by the addition of silver nitrate (1.14 g.) in water (3 ml.) dropwise to a 2 normal sodium hydroxide solution (6.8 ml.). A precipitate is formed. Added to the precipitate in ice water bath is the δ lactol of part B above (1 g.) in tetrahydrofuran (4 ml.). When the addition is complete, the ice bath is removed and the reaction mixture allowed to warm to ambient temperature. When the reaction is complete, as shown by thin layer chromatography (chloroform and methanol), (9:1), impurities are removed by filtration. The filtrate is then extracted with diethyl ether. The aqueous layer is then chilled in an ice bath and acidified with 10 percent potassium bisulfate solution to pH less than 2. This aqueous mixture is then extracted with diethyl ether. The ethereal extracts are then combined, washed with brine, dried over magnesium sulfate, filtered, and evaporated under reduced pressure to yield the formula XXIX lactone.

D. The formula XXIX lactone prepared in part C above is then transformed to its bis-tetrahydropyranyl ether derivative following the procedure described in Example 8, part B.

E. The formula XXX compound prepared in part D above is then reduced to the corresponding δ lactol bis-tetrahydropyranyl ether by the procedure described in Example 8, part C.

F. 3-Carboxypropyltriphenylphosphonium bromide (prepared by heating 4-bromobutyric acid and triphenylphosphine in benzene at reflux for 18 hours, and thereafter purifying), 106 g., is added to sodiomethylsulfinylcarbanide prepared from sodium hydride (2.08 g., 57 percent) and 30 ml. of dimethylsulfoxide. The resulting Wittig reagent is combined with the formula lactol of part above and 20 ml. of dimethylsulfoxide. The mixture is stirred overnight, diluted with about 200 ml. of benzene, and washed with potassium hydrogen sulfate solution. The two lower layers are washed with dichloromethane, the organic phases are combined, washed with brine, dried, and concentrated under reduced pressure. The residue is subjected to chromatography over acid washed silica gel, eluting with ethyl acetate and isomeric hexanes (3:1). Those fractions as shown to contain the desired compound by thin layer chromatography are combined to yield pure product.

Following the procedure of Example 12, but using in place of the (3S) starting material the corresponding (3R) starting material there is obtained the corresponding 15-epi-14-chloro-PGF$_{1\alpha}$-type compound.

Following the procedure of Example 12, but using in place of the 3-carboxypropyltriphenylphosphonium bromide, 4-carboxybutyltriphenylphosphonium bromide, or 5-carboxypentyltriphenylphosphonium bromide, there are prepared the corresponding formula XXXIII compounds wherein g is 2 or 3.

Further, following the procedure of Example 12, but using in place of the starting material the various formula XXVI lactols, there are prepared the corresponding cis-4,5-didehydro-14-chloro-PGF$_{1\alpha}$- or 11-deoxy-PGF$_{1\alpha}$-type products.

EXAMPLE 13

14-Chloro-16,16-dimethyl-PGF$_{2\alpha}$, methyl ester, 11,15-bis-tetrahydropyranyl ether (Formula XXXIII: g is one, n is one, R$_3$ and R$_4$ of the L$_1$ moiety are methyl, M$_6$ is

R$_1$ is methyl, R$_2$ is hydrogen, R$_7$ is n-butyl, R$_{18}$ is tetrahydropyranyloxy, and Y$_1$ is trans-CH=C(Cl)—) or its 15-epimer.

Refer to Chart A.

A. Sodium hydride (0.40 g., 57 percent in mineral oil) in 20 ml. of dimethylsulfoxide, is added to 1.82 g. of 4-carboxybutyltriphenylphosphonium bromide. The reaction mixture is maintained at 20° C. with stirring for 25 min. A solution of the title compound of Example 8 (0.39 g.) in 10 ml. of toluene is added. The reaction mixture is stirred at ambient temperature for 2 hours and diluted with benzene. Potassium bisulfate (2.7 g. in 30 ml. of water) is slowly added, maintaining the reaction temperature at less than or equal to 10° C. The aqueous layer is extracted with 50 ml. of benzene and the organic extracts are washed successfully with 50 ml. of water and 50 ml. of brine before combining, drying, and evaporating. Evaporation yields semi-crystalline residue which is chromatographed on 100 g. of acid washed silica gel eluting 20 percent ethyl acetate m-hexane. Thereby 0.241 g. of the pure free acid of the title product is obtained. NMR absorptions are observed at 0.65–1.1, 1.1–1.4, 1.4–1.8, 1.8–2.6, 2.8–4.4, 4.05, 4.4–4.8, 5.2–5.75, and 6.0–6.0 δ.

B. A solution of the reaction product of part A above and 15 ml. of diethyl ether is esterified with diazomethane, used in stoichiometric excess. The crude methyl ester is chromatographed on 100 g. of silica gel packed in 2 percent acetone methylene chloride. Elution with 2–12 percent acetone in methylene chloride, yields the title compound.

Following the procedure of Example 13, but using the (3R) lactol there is obtained the corresponding 15-epi-14-chloro-PGF$_{2\alpha}$, methyl ester, 11,15-bis-tetrahydropyranyl ether. NMR absorptions are observed at 0.7–1.1, 1.1–1.4, 1.4–1.8, 1.8–2.55, 3.15–4.2, 3.66, 4.05, 4.5–4.8, 5.2–5.8, and 5.6 δ.

Following the procedure of Example 13, but using 5-carboxypentyltriphenylphosphonium bromide or 6-carboxyhexyltriphenylphosphonium bromide in place of 4-carboxybutyltriphenylphosphonium bromide there is obtained the corresponding 2a-homo or 2a,2b-dihomo-14-chloro-PGF$_{2\alpha}$-type compound or its 15-epimer.

Further, following the procedure of Example 13, but using in place of 4-carboxybutyltriphenylphosphonium bromide, b 4,4-difluoro-4-carboxybutyltriphenylphosphonium bromide there is obtained the corresponding 2,2-difluoro-14-chloro-PGF$_{2\alpha}$-type tetrahydropyranyl ether or its 15-epimer.

Further, following the procedure of Example 13, but using in place of the formula XXXII lactol starting material therein one of the various lactols described following Example 8, and optional by any of the Wittig reagents described above, there are prepared the corresponding 14-chloro or 11-deoxy-14-chloro-PGF$_{2\alpha}$-type products.

EXAMPLE 14

15-Methyl-14-chloro-PGF$_{2\alpha}$, methyl ester (Formula XXXIX: R$_3$ and R$_4$ of the L$_1$ moiety are hydrogen, M$_1$ is

M$_{19}$ is

R$_1$ is methyl, R$_7$ is n-butyl, R$_8$ is hydroxy, Y$_1$ is trans-CH=C(Cl)—, and Z$_2$ is cis-CH=CH(CH$_2$)$_3$—) or its 15-epimer.

A. A solution of 5.7 g. of the reaction product of Example 7, 3α-benzoyloxy-5α-hydroxy-2β-[(3S)-3-hydroxy-3-methyl-cis-1-octenyl]-1α-cyclopentaneacetic acid γ lactone in 150 ml. of methanol is deacylated according to the procedure of Example 8, part A, yielding of 3α,5α-dihydroxy-2β-[2-chloro-(3S)-3-hydroxy-3-methyl-trans-1-octenyl]-1α-cyclopentaneacetic acid γ lactone.

A sample of the corresponding (3R) starting material is deacylated in a similar fashion, yielding the corresponding (3R) product.

B. A solution of 3.65 g. of the reaction product of part A in 150 m. of tetrahydrofuran is cooled to −60° C. Diisobutylaluminum hydride and toluene (85 ml.) is added over a period of 23 minutes at a temperature of −70° C. The reaction mixture is stirred for an additional 24 minutes. Thereafter 100 ml. of saturated aqueous ammonium chloride solution is slowly added at a temperature of −60° C. The resulting mixture is then stirred and allowed to warm to room temperature, yielding a gelatin as precipitate. This mixture is then diluted with 70 ml. of water and 150 ml. of ethyl acetate, mixed thoroughly and filtered. The filter cake is washed with water and ethyl acetate. The aqueous layer is extracted with ethyl acetate. The combined organic extracts are washed with brine, dried over sodium sulfate, and evaporated to yield the lactol corresponding to lactone starting material.

C. Following the procedure of Example 13, sodium hydride in dimethylsulfoxide is combined with 4-carboxybutyltriphenylphosphonium bromide to yield the title compound in free acid form.

The reaction product of part C above is esterified with diazomethane following the procedure described above, yielding the title compound.

Following the procedure of steps B-D above, but using the deacylated (3R)-lactone there is obtained 1. 15-epi-15-methyl-14-chloro-PGF$_{2\alpha}$, methyl ester.

The preparation of the above title compound or its 15-epimer is optionally accomplished by omitting the chromatographic separation step therein. Thereafter, by the procedure of Example 8 the corresponding 3(RS)-3-methyl lactol is prepared. Thereafter, following the procedure of Example 13, the (15RS)-15-methyl-14-chloro-PGF$_{2\alpha}$-bis-tetrahydropyranyl ether, methyl ester is prepared by methyl esterification of the free acid so formed. The tetrahydropyranyl ether moieties may then be hydrolyzed and the C-15 epimers separated by chromatographic techniques.

Following the procedure of Example 14, or the optional procedure discussed above, there are prepared 15-epi-15-methyl or 15-methyl-PGF$_{2\alpha}$-type compounds from the corresponding lactols described following Example 8.

Further, using the compounds described in or following Examples 10, 12, or 13 there are prepared the corresponding 5-oxa-, or cis-4,5-didehydro-15-methyl- or 15-epi-15-methyl-14-chloro-PGF$_{2\alpha}$-type products.

EXAMPLE 15

15-Methyl-14-chloro-PGF$_{2\alpha}$(Formula: R$_3$ and R$_4$ of the L$_1$ moiety are hydrogen, M$_1$ is

M$_{19}$ is

R$_1$ is hydrogen, R$_7$ is n-butyl, R$_8$ is hydroxy, Y$_1$ is trans-CH=C(Cl)—, and Z$_2$ is cis-CH=CH—(CH$_2$)$_3$—) or its 15-epimer.

A solution of 2.0 g. of the reaction product of Example 14, or its 15-epimer, in 20 ml. of methanol is cooled to 0° C. The resulting mixture is thereafter treated dropwise under a nitrogen atmosphere with 12 ml. of 10 percent aqueous sodium hydroxide solution. The mixture is then allowed to warm to room temperature and stirred for 2 hours. After removal of the methanol by evaporation under reduced pressure the residue is diluted with water and extracted with methylene chloride. The aqueous layer is then cooled with ice, treated with 24 ml. of 2 molar aqueous sodium bisulfate solution and extracted immediately with ethyl acetate. The combined organic extracts are washed with brine, dried over anhydrous sodium sulfate, and concentrated. Crude product may then be chromatographed on 150 g. of silica gel, yielding the title compound or its 15-epimer.

Following the procedure of Example 15, but using any of the 15-methyl-14-chloro-PGF$_\alpha$ or 11-deoxy-15-methyl-14-chloro-PGF$_\alpha$-type methyl esters, there are prepared the corresponding free acid products.

EXAMPLE 16

14-Chloro-16,16-dimethyl-PGF$_{2\alpha}$ methyl ester (Formula XXXIX: R$_3$ and R$_4$ of the L$_1$ moiety are methyl, M$_1$ is M$_{19}$ is

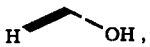

R$_1$ is methyl, R$_7$ is n-butyl, R$_8$ is hydroxy, Y is trans-CH=C(Cl)—, and Z$_2$ is cis-CH=CH—(CH$_2$)$_3$—) or its 15-epimer.

Refer to Chart A.

14-Chloro-16,16-dimethyl-PGF$_{2\alpha}$, bis-tetrahydropyranyl ether (0.241 g.) is reacted with 20 ml. of tetrahydrofuran, water, and acetic acid (1:3:6) at 40° C. for 4 hours. Thereafter, the resulting mixture is diluted with 60 ml. of water and lyophylized. The residue is then esterified with diazomethane, quenching with ethereal acetic acid, and thereafter washing with sodium bicarbonate and brine, drying and evaporating to a residue. The chromatographed (eluting with methylene chloride and acetone, 3:1) residue yields 0.056 g. of pure product. NMR absorptions are observed at 0.44, 0.98, 1.1–1.42, 1.42–2.6, 2.7–3.4, 3.7, 3.8–4.5, 4.04, 5.25–5.8, and 5.65 δ. The mass spectrum shows peaks at 395, 340, 331, 296, and 281. Characteristic ester IR absorptions are observed at 1550, 1577, 1760, and 3450 cm$^{-1}$.

Using corresponding 15-epimeric starting material the corresponding 15-epimeric product is prepared.

Following the procedure of Example 16, but using as starting material any of the 11,15-bis-tetrahydropyranyl ethers, 11-tetrahydropyranyl ethers, or 15-tetrahydropyranyl esters described in and following Examples 10, 12, or 13, there are prepared respectively the corresponding 14-chloro-PGF$_{2\alpha}$-, or 11-deoxy-14-chloro-PGF$_{2\alpha}$-type compounds.

EXAMPLE 17

15-Methyl-14-chloro-PGE$_2$, methyl ester, (Formula XXXIX: R$_3$ and R$_4$ of the L$_1$ moiety are hydrogen, M$_{19}$ is

R$_1$ and R$_5$ are methyl, R$_7$ is n-butyl, R$_8$ is hydroxy, Y$_1$ is transCH=C(Cl), Z$_2$ is cis-CH=CH—(CH$_2$)$_3$—) or its 15-epimer.

A. A solution of 15-methyl-14-chloro-PGF$_{2\alpha}$, methyl ester, 11,15-bis-tetrahydropyranyl ether, prepared above, in 60 ml. of acetone is cooled to −25° C. Thereupon 1.9 ml. of Jones reagent is added. The reaction mixture is then stirred for 25 minutes at −25° C. and isopropyl alcohol (1.9 ml.) is added after an additional 15 minutes at −25° C. The reaction mixture is diluted with 200 ml. of water (0° C.) and extracted with diethyl ether. Ethereal extracts are washed with 75 ml. of cold 0.1 normal potassium bicarbonate, 150 ml. of brine, dried over magnesium sulfate, and evaporated, thereby yielding 15-methyl-14-chloro-PGE$_2$, methyl ester, 11,15-bis-tetrahydropyranyl ether.

B. A solution of the crude product of part A above is reacted with 16 ml. of tetrahydrofuran, water, and acetic acid (1:3:6) and allowed to stand at 40° C. for 4 hours. The resulting mixture is thereafter diluted with 120 ml. of water and freeze dried. The residue is dissolved in diethyl ether and washed with potassium bicarbonate, brine, and thereafter dried and evaporated to yield crude product. The crude product is chromatographed on 25 g. of silica gel packed in 5 percent acetone in methylene chloride. Elution with 5 to 40 percent acetone in methylene chloride yields the pure product.

Following the above procedure but using 15-epimeric starting material, the corresponding 15-epimer is prepared.

Following the procedure of Example 17, but using the various 15-methyl-14-chloro-PGF$_\alpha$or 11-deoxy-PGF$_\alpha$methyl ester, 11,15-bis-tetrahydropyranyl ethers, or 15-tetrahydropyranyl ethers, as prepared in or following Examples 9, 10, 11, 12, and 13 there are prepared the corresponding 15-methyl-14-chloro-PGE or 11-deoxy-14-chloro-PGE-type products.

EXAMPLE 18

15-Methyl-14-chloro-PGE$_2$ or its 15-epimer.

The title compound is prepared by enzymatic hydrolysis of the methyl ester of the reaction product of Example 17 or its 15-epimer.

The enzyme is prepared as follows:

Freshly harvested colony pieces of Plexaura homomalla (Esper), 1792, forma S (10 kg.), are chopped into pieces less than 3 cm. in their longest dimension and then covered with about 3 volumes (20 l.) of acetone. The mixture is stirred at about 25° C. for one hour. The solids are separated by filtration, washed with a quantity of acetone, air dried, and finally stored at about 20° C. as a coarse enzymatic powder.

The esterase hydrolysis then proceeds as follows:

The suspension of the esterase composition prepared above in 25 ml. of water is combined with the solution of the above indicated starting material. 8 ml. of methanol is added, and the resulting mixture is stirred at about 25° C. for 24 hours. 50 ml. of acetone is then added and the mixture is stirred briefly, filtered, and the filtrate is then concentrated under reduced pressure. The aqueous residue is then acidified to pH 3.5 with citric acid and extracted with dichloromethane. The combined extracts are concentrated under reduced pressure to yield the title acid.

Following the procudure of Example 18, but using the various methyl esters described following Example 17, the corresponding products are prepared.

EXAMPLE 19

14-Chloro-PGF$_{1\alpha}$, methyl ester, or its 15-epimer.

A solution of 4.8 g. of 14-chloro-PGF$_{2\alpha}$, methyl ester in 90 ml. of acetone and 60 ml. of benzene containing 0.75 g. of tris(triphenylphosphine)rhodium (l) chloride is shaken under hydrogen atmosphere at ambient temperature at 1 to 3 atmospheres pressure for 3.5 hours. Thereafter the solvent is evaporated and the residue chromatographed on 400 g. of silica gel packed in methylene chloride eluting with one to 6 percent methanol in methylene chloride. There is recovered 0.90 g. of impure product. The above product is purified using silica gel chromatography, thereby preparing pure product.

Following the above procedure, but using 15-epi-14-chloro-PGF$_{2\alpha}$, methyl ester, there is prepared the corresponding 15-epi-14-chloro-PGF$_{1\alpha}$, methyl ester.

Following the procedure of Example 20, but using in place of the indicated starting material any of the PGF$_{2\alpha}$ or 11-deoxy-PGF$_{2\alpha}$-type compounds described in or following Example 13, there are prepared the corresponding PGF$_{1\alpha}$ or 11-deoxy-PGF$_{1\alpha}$-type products.

EXAMPLE 20

14-Chloro-PGE$_1$, methyl ester, or its 15-epimer.

The title compound of this Example is prepared by oxidation of the compound of Example 19, using the procedure described in Example 17, part A.

Using the corresponding 15-epimer, there is prepared 15-epi-14-chloro-PGE$_1$, methyl ester.

Following the procedure of Example 20, but using any of the 11-deoxy-PGF$_{1\alpha}$- or PGF$_{1\alpha}$-type compounds described following Example 19, there are prepared the corresponding 11-deoxy-PGE$_1$- or PGE$_1$-type compounds.

Accordingly, following the procedures of Examples 14–20 there are prepared the various 14-chloro-PGF$_{2\alpha}$-, 2,2-difluoro-PGF$_{2\alpha}$-, 2a,2b-dihomo-PGF$_{2\alpha}$-, 5-oxa-PGF$_{1\alpha}$-, cis-4,5-didehydro-PGF$_{1\alpha}$-, PGF$_{1\alpha}$-, 2,2-difluoro-PGF$_{1\alpha}$-, or 2a,2b-dihomo-PGF$_{1\alpha}$-type compounds or the corresponding PGE-type compounds, optionally substituted at C-15 with methyl at C-16 with one or 2 methyl, or one or 2 fluoro, or phenoxy, or optionally substituted at C-17 with a phenyl or substituted phenyl moiety.

EXAMPLE 21

14-Chloro-16,16-dimethyl-PGF$_{2\beta}$, methyl ester (Formula XXXIX: R$_3$ and R$_4$ of the L$_1$ moiety are methyl, M$_1$ is 

M$_{19}$ is 

R$_1$ is methyl, R$_7$ is n-butyl, R$_8$ is hydroxy, Y$_1$ is trans-CH=C(Cl)—, and Z$_2$ is cis-CH=CH—(CH$_2$)$_3$—).

Refer to Chart F.

A solution of 0.3 g. of 14-chloro-16,16-dimethyl-PGE$_2$, methyl ester, in 15 ml. of methanol is cooled to −15° C. Thereafter 16 mg. of borohydride is added. After 45 minutes, 2 ml. of 50 percent acetic acid in water is slowly added. The reaction mixture is then allowed to warm to ambient temperature and then evaporated at reduced pressure. The residue is then shaken with ethyl acetate and water. The organic phase is then washed with aqueous sodium bicarbonate, brine, and then dried and evaporated to yield crude product. A column of 25 g. of silica gel packed in ethyl acetate is eluted with 70-100 percent ethyl acetate in cyclohexane. Crude product is then rechromatographed eluting with 0.5 to 3 percent methanol in methylene chloride. Rechromatographing yields the 9β-epimer.

Using the corresponding 15-epimeric starting material the corresponding 15-epimeric product is prepared.

Following the procedure of Example 21, but using the various PGE$_2$-, 11-deoxy-PGE$_2$-, PGE$_1$-, or 11-deoxy-PGE$_1$-type compounds described in the preceding examples, there are obtained the corresponding PGF$_{2\beta}$, 11-deoxy-PGF$_{2\beta}$, PGF$_{1\beta}$, or 11-deoxy-PGF$_{1\beta}$-type compounds.

EXAMPLE 22

14-Chloro-16,16-dimethyl-PGA$_2$ (Formula XL: R$_3$ and R$_4$ of the L$_1$ moiety are methyl, M$_1$ is

R$_1$ is hydrogen, R$_7$ is n-butyl, Y$_1$ is trans-CH=C(Cl)—, and Z$_2$ is cis-CH=CH—(CH$_2$)$_3$—).

Refer to Chart A.

A solution of 14-chloro-16,16-dimethyl-PGE$_2$ (300 mg.), 4 ml. of tetrahydrofuran, and 4 ml. of 0.5 normal hydrochloric acid is left standing at ambient temperature for 5 days. Brine and dichloromethane in ether (1:3) are added and the mixture is stirred. The organic phase is separated, dried, and concentrated. The residue is dissolved in diethyl ether and the solution is extracted with aqueous sodium bicarbonate. The aqueous phase is acidified with dilute hydrochloric acid and then extracted with dichloromethane. This extract is then dried and concentrated to yield the title compound.

Following the procdure of Example 22, but using any of the PGE$_2$- or PGE$_1$-type compounds described above there are respectively prepared the corresponding PGA$_2$- or PGA$_1$-type compounds.

EXAMPLE 24

14-Chloro-16,16-dimethyl-PGF$_{2\alpha}$ sodium salt.

A solution of 14-chloro-16,16-dimethyl-PGF$_{2\alpha}$ (100 mg.) in 50 ml. of water ethanol mixture (1:1) is cooled at 5° C. and neutralized with an equivalent amount of .1 normal aqueous sodium hydroxide solution. The neutral solution is then concentrated to a residue of the title compound.

Following the procdure of Example 24, using potassium hydroxide, calcium hydroxide, tetramethyl ammonium hydroxide, or benzyltrimethylammonium hydroxide in place of sodium hydroxide there is obtained the corresponding salts of 14-chloro-16,16-dimethyl-PGF$_{2\alpha}$. Likewise following the procedure of Example 24 each of the various other prostaglandin-type acids described above is transformed to the corresponding sodium, potassium, calcium, trimethylammonium, or benzyltrimethylammonium salt.

EXAMPLE 25

3-oxa-3,7-inter-m-phenylene-4,5,6-trinor-PGF$_{1\alpha}$ (Formula LXX: R$_1$ is hydrogen, R$_3$ and R$_4$ of the L$_1$ moiety are hydrogen, g is one, and R$_7$ is n-butyl) or 3,7-inter-m-phenylene-4,5,6-trinor-PGF$_{1\alpha}$.

Refer to Chart B.

A. Optically Active Bicyclo[3.1.0]-hex-2-ene-6-endocarboxaldehyde.

Following the procedure of Preparation 1 of U.S. Pat. No. 3,711,515, racemic bicyclo[3.1.0]hex-2-ene-6-endo-carboxaldehyde is prepared from bicyclo[2.2.1]-hepta-2,5-diene and peracetic acid.

The racemic compound is resolved by the procedure of Example 13 of U.S. Pat. No. 3,711,515, forming an oxazolidine as follows:

Racemic bicyclo[3.1.0]hex-2-ene-6-endo-carboxaldehyde (12.3 g.) and l-ephedrine (16.5 g.) are dissolved in about 150 ml. of benzene. The benzene is removed under vacuum and the residue taken up in about 150 ml. of isopropyl ether. The solution is filtered, then cooled to −13° C. to yield crystals of 2-endo-bicyclo-[3.1.0]hex-2-en-6-yl-3,4-dimethyl-5-phenyl-oxazolidine, 11.1 g., m.p. 90°-92° C. Three recrystallizations from isopropyl ether, cooling each time to about −2° C., yield crystals of the oxazolidine, 2.2 g., m.p. 100°-103° C., now substantially a single isomeric form as shown by NMR.

The above re-crystallized oxazolidine (1.0 g.) is dissolved in a few ml. of dichloromethane, charged to a 20 g. silica gel column and eluted with dichloromethane. The silica gel is chromatograph-grade (Merck), 0.05-0.2 mm particle size, with about 4-5 g. of water per 100 g. Fractions of the eluate are collected, and those shown by thin layer chromatography (TLC) to contain the desired compound are combined and evaporated to an oil (360 mg.). This oil is shown by NMR to be the desired title compound, substantially free of the ephedrine, in substantially a single optically-active isomeric form. Points on the circular dichroism curve are (λ in nm., θ): 350, 0; 322.5, 4,854; 312, −5,683; 302.5, −4,854; 269, 0; 250, 2,368; 240, 0; and 210, −34,600.

B. 1-Bicyclo[3.1.0]hex-2-ene-6-endo-carboxaldehyde Neopentyl Glycol Acetal (Formula LXI: $R_{55}$ and $R_{56}$ taken together are —CH$_2$—C(CH$_3$)$_2$—CH$_2$— and ~ is endo).

A mixture of 2,2-dimethyl-1,3-propanediol (900 g.), 5 l. of benzene, and 3 ml. of 85 percent phosphoric acid is heated at reflux. To it is added, in 1.5 hours, a solution of optically active bicyclo[3.1.0]hex-2-ene-6-endo-carboxaldehyde (part A, 500 g.) in one liter of benzene. Provision is made to take off azeotropically distilled water with a Dean-Stark trap. After 3 hours the mixture is cooled and extracted with 2 liters of 5 percent sodium bicarbonate. The organic phase is dried over sodium sulfate and concentrated under reduced pressure. The resulting semisolid residue is taken up in methanol and recrystallized, using a total of 1200 ml. of methanol to which 600 ml. of water is added, then chilled to −13° C. to yield 300 g. of the title compound, m.p. 52°-55° C., and having NMR peaks at 0.66, 1.20, 0.83-2.65, 3.17-3.8, 3.96, and 5.47-5.88 δ, [α]$_D$−227° (C=0.8976 in methanol), and R$_f$0.60 (TLC on silica gel in 25 percent ethyl acetate in mixed isomeric hexanes). Further work-up of the mother liquors yields 50-100 g. of additional product.

C. d-8-(m-Acetoxyphenyl)-7-oxa-tricyclo-[4.2.0.0$^{2,4}$]-octene-6-endo-carboxaldehyde Neopentyl Glycol Acetal (Formula LXII: $R_{55}$ and $R_{56}$ taken together are —CH$_2$—C(CH$_3$)$_2$—CH$_2$—, $R_{63}$ is

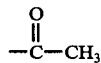

and ~ is endo).

A solution of the formula LXI 1-bicyclo[3.1.0]hex-2-ene-6-endo-carboxaldehyde neopentyl glycol acetate (Part B, 5.82 g.) and m-acetoxy-benzaldehyde (1.64 g.) in 25 ml. of benzene is charged to a Pyrex photolysis vessel equipped with an immersible water-cooled cold-finger and a fritted gas inlet tube. Dissolved oxygen is removed by bubbling nitrogen through the solution. The mixture is then irradiated at 350 nm. with a Rayonet Type RS Preparative Photochemical Reactor (The Southern New England Ultraviolet Co., Middletown, Conn.) equipped with six RUL 3500 A lamps. After 24 hours the photolysate is concentrated under reduced pressure to a pale yellow oil, 10 g., which is subjected to silica gel chromatography. Elution with 10-70 percent ethyl acetate in Skellysolve B (mixture of isomeric hexanes) yields separate fractions of the recovered starting materials and the formula LXXXII title compound, a pale yellow oil, 0.86 g., having NMR peaks at 0.68, 1.20, 0.8-2.5, 2.28, 2.99, 3.12-3.88, 3.48, 4.97-5.52, and 6.78-7.60 δ; infrared absorption bands at 3040, 2950, 2860, 2840, 1765, 1610, 1590, 1485, 1470, 1370, 1205, 1115, 1020, 1005, 990, 790 and 700 cm.$^{-1}$; mass spectral peaks at 358, 357, 116, 115, 108, 107, 79, 70, 69, 45, 43, and 51; [α]$_D$ +55° (C=0.7505 in 95 percent ethanol); and R$_f$0.18 (TLC on silica gel in 25 percent ethyl acetate in mixed isomeric hexanes).

D. d-2-Exo-[m-(pivaloyloxy)benzyl]-3-exo-bicyclo[3.1.0]hexane-6-endo-carboxaldehyde Neopentyl Glycol Acetal (Formula LXIV: $R_{55}$ and $R_{56}$ taken together, $R_{68}$ is

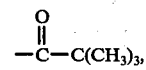

and ~ is endo).

A mixture of lithium (0.25 g.) in 70 ml. of ethylamine is prepared at 0° C. and cooled to −78° C. A solution of the formula LXII d-8-(m-acetoxyphenyl)-7-oxa-tricyclo[4.2.0.0$^{2,4}$]-octane-6-endo-carboxaldehyde neopentyl glycol acetal (part C 1.83 g.) in 10 ml. of tetrahydrofuran is added dropwise in about 5 minutes. After stirring at −78° C. for about 3.5 hours the reaction is quenched with solid ammonium chloride and water-tetrahydrofuran. Unreacted lithium is removed, the mixture is warmed slowly to about 25° C., and ethylamine is removed. The residue is neutralized with dilute acetic acid, mixed with 200 ml. of brine, and extracted with ethyl acetate. The organic phase is washed with brine and a mixture of brine and saturated aqueous sodium bicarbonate (1:1), and dried over sodium sulfate. Concentration under reduced pressure yields the formula LXIII diol as a pale tan foamed oil, 1.64 g., having R$_f$ 0.03 (TLC on silica gel in 25 percent ethyl acetate in mixed isomeric hexanes).

The product of the preceeding paragraph is dissolved in 30 ml. of pyridine and treated with 1.5 ml. of pivaloyl chloride over a period of 22 hours at about 25° C. The reaction mixture is mixed with water, then brine and extracted with ethyl acetate. The organic phase is washed successively with brine, water, saturated aqueous copper (II) sulfate, saturated aqueous sodium bicarbonate, and brine, and dried over sodium sulfate. Concentration under reduced pressure yields a residue, 2.53 g., which is subjected to silica gel chromatography to yield the formula LXIV title compound, 1.87 g., having NMR peaks at 0.71, 1.20, 1.33, 0.9-3.1, 3.28-4.00, 4.17, 4.7-5.2, and 6.77-7.53 δ; mass spectral peaks at 486, 485, 115, 73, 72, 57, 44, 43, 42, 41, 30, 29, 15; [α]$_D$ +10° (C=0.8385 in ethanol); and R$_f$0.50 (TLC on silica gel in 25 percent ethyl acetate in mixed isomeric hexanes).

E. 2-Exo-[m-(pivaloyloxy)benzyl]-3-exo-(pivaloyloxy)-bicyclo[3.1.0]hexane-6-endo-carboxaldehyde Formula LXV: $R_{66}$ is

and ~ is endo).

The formula LXIV acetal, i.e. d-2-exo-[m-(pivaloyloxy)benzyl]-3-exo-(pivaloyloxy)-bicyclo[3.1.0]hexane-6-endo-carboxaldehyde neopentyl glycol acetal (part D, 0.48 g.) is treated at 0° C. with 25 ml. of 88 percent formic acid for 4 hours. The mixture is diluted with 200 ml. of brine and extracted with ethyl acetate. The organic phase is washed with brine and saturated aqueous sodium bicarbonate, and dried over magnesium sulfate. Concentration under reduced pressure yields an oil, 0.55 g., which is subjected to silica gel chromatography. Elution with 5-15 percent ethyl acetate in Skellysolve B yields the formula LXV title compound as an oil, 0.37 g., having NMR peaks at 1.20, 1.33, 0.6–3.2, 5.1–5.5, 6.6–7.5, and 9.73 $\delta$; and $R_f$ 0.50 (TLC on silica gel in 25 percent ethyl acetate in mixed isomeric hexanes).

F. 2-Exo-[m-(pivaloyloxy)benzyl]-3-exo-(pivaloyloxy)-6-endo-(cis-1-heptenyl)-bicyclo[3.1.0]hexane (Formula LXVI: $R_3$ and $R_4$ of the $L_1$ moiety are both hydrogen, $R_7$ is n-butyl, $R_{66}$

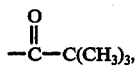

$R_{53}$ is hydrogen, and ~ is endo); and 2-Exo-(m-hydroxybenzyl)-3-exo-hydroxy-6-endo-(cis-1-heptenyl)bicyclo[3.1.0]-hexane (Formula LXVII: $R_3$ and $R_4$ of the $L_1$ moiety are both hydrogen, $R_7$ is n-butyl, $R_{53}$ and $R_{66}$ are hydrogen, and ~ is endo).

A Wittig ylid reagent is prepared in 10 ml. of benzene from n-hexyltriphenylphosphonium bromide (0.79 g.) and n-butyllithium (0.6 ml. of 2.32 M. solution in hexane) at about 25° C. for 0.5 hours. After the precipitated lithium bromide has settled, the solution is removed and added to a cold (0° C.) slurry of the formula LXV aldehyde (part E, 0.37 g.). After 15 minutes there is added 1.0 ml. of acetone and the mixture is heated to 60° C. for 10 minutes. The mixture is concentrated under reduced pressure. The residue is washed with 10 percent ethyl acetate in Skellysolve B and these washings are concentrated to the formula LXVI title compound, an oil, 0.33 g. having NMR peaks at 1.18, 1.33, 0.6–3.2, 4.5–6.0, and 6.67–7.62 $\delta$; and $R_f$ 0.78 (TLC or silica gel in 25 percent ethyl acetate in Skellysolve B).

The above product of the preceeding paragraph is transformed to the formula LXVII diol by treatment with sodium methoxide (2.5 ml. of a 25 percent solution in methanol) for 4 hours, followed by addition of 0.5 g. of solid sodium methoxide and further stirring for 15 hours at 25° C. then at reflux for 6 hours. The mixture is cooled, mixed with 300 ml. of brine, and extracted with ethyl acetate. The organic phase is washed with brine, dried over magnesium sulfate, and concentrated under reduced pressure to a residue, 0.27 g. The residue is subjected to silica gel chromatography, eluting with 25-35 percent ethyl acetate in Skellysolve B, to yield the formula-LXVII title compound as an oil, 0.21 g., having NMR peaks at 0.87, 0.6–3.25, 3.88–4.35, 4.82–5.92, and 6.47–7.33 $\delta$; and $R_f$ 0.13 (TLC on silica gel in 25 percent ethyl acetate in Skellysolve B).

G. 2-Exo-{m-[(methoxycarbonyl)methoxybenzyl]}-3-exo-hydroxy-6-endo-(cis-1-heptenyl)bicyclo[3.1.0]-hexane (Formula LXVIII : $R_3$ and $R_4$ of the $L_1$ moiety are both hydrogen, $g$ is one, $R_7$ is n-butyl, $R_1$, $R_{53}$, and $R_{66}$ are hydrogen, and ~ is endo).

The formula LXVII diol, i.e. 2-exo(m-hydroxybenzyl)-3-exo-hydroxy-6-endo(cis-1-heptenyl)bicyclo[3.1.0]hexane (part F, 0.19 g.) is treated in 8 ml. of dioxane with bromoacetic acid (0.61 g.) and 6 ml. of 1N aqueous sodium hydroxide. After the mixture has been heated at reflux for 3 hours, with sodium hydroxide solution added when necessary to maintain a pH of about 10, the mixture is cooled, diluted with 100 ml. of water, and extracted with diethyl ether. The aqueous phase is acidified to pH 1-2 and extracted with ethyl acetate to yield the formula -LXVII title compound, a pale yellow oil, 0.20 g. Recovered formula LXVII diol is obtained from the diethyl ether organic phase on drying and concentrating, 0.025 g.

H. 3-Oxa-3,7-inter-m-phenylene-4,5,6-trinor-PGF$_{1\alpha}$- (Formula LXX: $R_3$ and $R_4$ of the $L_1$ moiety and $R_5$ and $R_6$ of the $M_1$ moiety are all hydrogen, $R_7$ is n-butyl, $g$ is one, and $R_1$ is hydrogen).

The formula LXVIII alkene is transformed to formula LXIX compound applying the procedure disclosed in U.S. Pat. No. 3,711,515. Thus, compound LXVIII (part G) is hydroxylated by the procedures of Example 6 of that patent to the formula LXIX glycol of Chart B, using osmium tetroxide either alone or in combination with N-methylmorpholine oxide-hydrogen peroxide complex.

The glycol is then either (1) sulfonated, for example to yield the bismesylate, and then hydrolyzed to a mixture of the title compound and its 15-epimer, applying the procedures of Example 7 of that patent, or (2) treated with substantially 100 percent formic acid to form the diformate and thereafter hydrolyzed to a mixture of the title compound and its 15-epimer, applying the procedures of Examples 20 and 21 of that patent. The epimers are separated by silica gel chromatography to yield the formula LXX compound or its 15-epimer.

A third route from glycol LXIX to the formula LXX compound is by way of a cyclic ortho ester

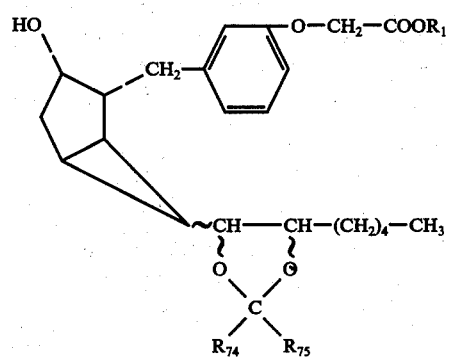

wherein $R_{74}$, $R_{75}$, and ~ are as defined above. The glycol is treated as a 1-20 percent solution in benzene with trimethyl orthoformate (1.5-10 molar equivalents) and a catalytic amount (1 percent of the weight of the glycol) of pyridine hydrochloride at about 25° C. The reaction is followed by TLC (thin layer chromatography) and is complete in a few minutes. There is thus obtained the cyclic ortho ester in 100 percent yield.

The cyclic ester is then treated with 20 volumes of 100 percent formic acid at about 25° C. In about 10 minutes the reaction mixture is quenched in water or aqueous alkaline bicarbonate solution and extracted with dichloromethane. The organic phase is shaken with 5 percent aqueous sodium bicarbonate, dried over sodium sulfate, and concentrated to yield the corresponding diester. The diester is contacted with 10–50 volumes of anhydrous methanol and 10–20 percent of its weight of potassium carbonate at about 25° C. unitl the ester groups are removed. The mixture of epimers thusly obtained is separated by silica gel chromatography yielding the two 15-epimeric forms of the formula LXX compound.

I. 2-Exo-[m-(carboxyethyl)benzyl]-3-exo-hydroxy-6-endo(cis-1-heptenyl)bicyclo-[3.1.0]hexane (Formula LXXXII: $Z_3$ is methylene, g is one, $R_3$ and $R_4$ of the $L_1$ moiety are hydrogen, $R_7$ $_L$is n-butyl, $R_1$ and $R_{53}$ are hydrogen and $\sim$ is endo).

With respect to Chart C, there is first prepared the formula LXXVII oxetane. Following the procedures of parts B and C, but replacing the m-acetoxybenzaldehyde of part B with the aldehyde of the formula

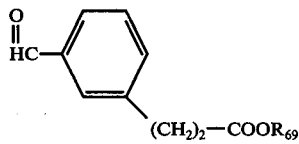

wherein $R_{69}$ is as defined above, the corresponding formula LXXVII oxetanes are obtained with a fully developed side chain.

Thereafter, following the procedures of parts D, E, and F, but replacing the formula LXII oxetane of part D with the oxetane obtained by the procedure of the preceeding paragraph of this part, there are obtained the corresponding formula LXXXI products.

Finally, the blocking groups on each LXXXI compound are removed by methods disclosed herein or known in the art to yield the formula LXXXII compound.

J. 3,7-inter-m-phenylene-4,5,6-trinor-PGF$_{1\alpha}$. Following the procedures of part H, the formula LXXXII alkene is transformed in several steps to the title product.

Following the procedure of Example 25 or optionally following the procedure described in the text accompanying Charts I or J, there are prepared the various 3,7-inter-m-phenylene-3-oxa-4,5,6-trinor- or 3,7-inter-m-phenylene-4,5,6-trinor-PGF$_{1\alpha}$-type compounds described in Charts B, C, or D, particularly those optionally substituted at C-16 with methyl, fluoro, phenoxy, or substituted phenoxy, or at C-17 with phenyl or substituted phenyl.

EXAMPLE 26

15-Methyl-13,14-didehydro-PGF$_{2\alpha}$, methyl ester (Formula CLXII : $R_1$ and $R_5$ are methyl, $R_3$ and $R_4$ of the $L_1$ moiety are hydrogen, $R_7$ is n-butyl, Y is —C≡C—, $Z_1$ is cis—CH═CH—(CH$_2$)$_3$— and ⌐D⌐ is

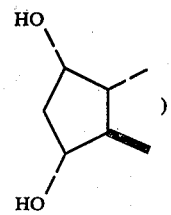

or its 15-epimer.

Refer to Charts F and J.

A. 15-Keto-PGF$_{2\alpha}$, methyl ester (14.4 g.) a formula CXXII compound, in pyridine (35 ml.) is treated with benzoyl chloride (10.5 ml.) and the reaction is allowed to continue for 2 hours. Thereafter, the resulting mixture is diluted with ice water, cooled, and diluted with ice cold 10 percent sulfuric acid and methylene chloride. The layers are then separated and the organic layer is then dried and evaporated yielding 24.18 g. of crude formula CXXIII product ($R_{16}$ is benzoyloxy). Chromatographic purification of this crude product (15.8 g.) on silica gel (600 g.) eluting with 15 percent ethyl acetate in hexane yields 13.6 g. of pure compound.

B. The reaction product of part A (5.0 g.) in carbontetrachloride (35 ml.) is cooled to freezing and bromine (1.38 g.) is added dropwise. The reaction is then diluted with methylene chloride, washed with sodium bicarbonate, dried, and evaporated to yield 5.6 g. of a crude 13,14-dibromo product. This crude dibromo product in pyridine (25 ml.) is heated to 90°–95° C for 1.5 hours. The mixture is then allowed to stand at room temperature for 24 hours and thereafter diluted with methylene chloride. The resulting dark solution is then partitioned with ice cold 5 percent sulfuric acid. The organic extract is washed with brine and sodium bicarbonate, dried, and evaporated to yield 5 g. of crude formula CXXIV product. Chromatographic purification on silica gel (320 g.), eluting with 5 percent ethyl acetate in benzene, yields 2.13 g. of product.

C. A solutuion of the reaction product of part B (6.32 g.) in tetrahydrofuran (45 ml.) at −78° C. is treated dropwise with excess ethereal methyl magnesium bromide. The reaction proceeds for 5 minutes, and is thereafter quenched by addition of aqueous potassium bisulfate. The reaction is then diluted with diethyl ester, washed with brine, dried, and evaporated to yield 6.5 g. of crude formula CXXV compound. The crude product is then purified on silica gel (315 g.), eluting with 7.5 percent ethyl acetate in benzene, yielding 4.28 g. of the formula CXXV compound as a mixture of C-15 epimers.

D. A solution of the reaction product of part C above (4.28 g.) in methanol (45 ml.) is treated with potassium carbonate (1.5 g.) at ambient temperature for 72 hours. The resulting solution is thereafter concentrated under reduced pressure, diluted with 5 percent sodium chloride solution, and extracted with methylene chloride. The aqueous phase is then cooled, acidified with 0.2 molar potassium bisulfate, and thereafter extracted successively with methylene chloride in methyl acetate.

The carboxylic acid containing fraction is washed with brine, dried and evaporated to yield 3.2 g. of the formula CXXVI compound ($R_1$ is hydrogen) as an epimeric mixture. This epimeric mixture is then esterified with excess diazomethane, yielding 2.32 g. of the corresponding methyl ester. High pressure liquid chromatography of this mixture of methyl esters on silica gel (512 g.) yields 15-epi-15-methyl-14-bromo-PGF$_{2\alpha}$, methyl ester, (0.75 g.) and 15-methyl-14-bromo-PGF$_{2\alpha}$, methyl ester (0.21 g.). Additional chromatographic runs yield 0.26 g. of the (15S)-compound.

The reaction product of part A exhibits NMR absorption at 0.89, 1.3–1.5, 3.61, 5.25–5.75, 6.3, 6.8–7.25, 7.25–7.7, and 7.75–8.2 $\delta$. Infrared absorptions are observed at 1250, 1575, 1594, 1625, 1680, and 1740.

The reaction product of part B exhibits NMR absorptions of 0.70–1.1, 1.1–3.05, 3.63, 5.25–5.8, 7.17, and 7.2–8.25 $\delta$. The mass spectrum shows peaks at 652, 530, 451, 408, 328, 497, and 105. Characteristic infrared absorptions are observed at 1720, 1610, and 1270 cm$^{-1}$.

The (15RS) epimeric mixture produced in part C exhibits NMR absorptions at 0.8–1.1, 1.1–3.4, 1.48, 3.62, 3.9–5.8, 6.15, 6.06, and 7.10–8.2 $\delta$.

For 15-methyl-14-bromo-PGF$_{2\alpha}$, methyl ester, NMR absorptions are observed at 0.7–1.1, 1.1–1.3, 1.49, 3.68, 3.85–4.4, 5.2–5.6, and 5.90 $\delta$. The mass spectrum shows base peak absorption at 604.2587, and other peaks at 586, 571, 533, 525, 507, 347, and 217. For 15-epi-15-methyl-14-bromo-PGF$_{2\alpha}$, methyl ester, NMR absorptions are observed at 0.7–1.1, 1.1–3.4, 1.47, 3.8–4.4, 4.25–5.6, and 5.93 $\delta$. Mass spectrum shows base peak absorption at 504.2615 and other peaks at 586, 573, 571, 533, 525, 514, 507, 496, 437, and 217.

E. A solution of the reaction product of part D, the 15-epi compound (0.19 g.) in dimethyl sulfoxide (9 ml.) is treated with 0.5 molar potassium tert-butoxide in dimethyl sulfoxide (0.9 ml.). Silver nitrate impregnated silica gel thin layer chromotography is used to monitor the progress of the reaction. After 2 hours, the reaction being complete, the reaction mixture is diluted with diethyl ether, washed with ice cold potassium bisulfate, a 5 percent sodium chloride solution, and a 5 percent sodium bicarbonate solution. Thereafter drying and evaporation of solvent yields 0.126 g. of crude (15R) title product.

The 15-epimer is prepared by the above process or is alternatively prepared by saponification of the methyl ester of the formula CXVI compound, dehydrohalogenation of the saponified product, and finally methyl esterification of the dehydrohalogenated product. According to this route a solution of the reaction product of part D (0.55 g.) in methanol (30 ml.) is treated with 2N sodium hydroxide (5 ml.) for 18 hours. The reaction is thereafter diluted with benzene and 0.2 M potassium bisulfate solution. The organic phase is then washed with 5 percent sodium chloride solution, dried, and evaporated to yield 0.49 g. of 15-epi-15-methyl-14-bromo-PGF$_{2\alpha}$. NMR absorptions are observed at 0.7–1.1, 1.1–3.4, 3.7–4.4, 5.1–5.75, and 5.95 $\delta$. Characteristic infrared absorptions are observed at 3300, 2600, and 1725 cm$^{-1}$. Thereafter dehydrohalogenation proceeds by reacting the above free acid (0.49 g.) in 10 percent methanolic dimethylsulfoxide (7 ml.) with sodium methoxide (4.43 mmol) in 10 percent methanolic dimethyl sulfoxide (10.2 ml.). This mixture reacts for 20 hours. Thereafter the reaction mixture is diluted with benzene, washed with ethyl acetate and benzene (1:1). The combined organic extracts are then washed with saturated sodium chloride, dried, and evaporated to yield 0.31 g. of crude 15-epi-15-methyl-13,14-didehydro-PGF$_{2\alpha}$. This crude product is then esterified with excess diazomethane, under a nitrogen atmosphere, followed by evaporation to yield 2.8 g. of crude methyl ester. Purification on silica gel (25 g.) eluting with methylene chloride in acetone yields 0.211 g. of pure 15-epi-15-methyl-13,14-didehydro-PGF$_{2\alpha}$, methyl ester. For the free acid NMR absorptions are observed at 0.7–1.1, 1.1–3.2, 1.45, 4.0–4.5, and 5.4–6.0 $\delta$. Characteristic absorptions are observed at 3200 to 3400, 2600 to 2700, 2220, and 1710 cm$^{-1}$. For the methyl ester NMR absorption are observed at 0.8–1.1, 1.1–3.2, 1.46, 4.0–4.5, 5.3–5.6 $\delta$.

Following the alternate procedure described above for the preparation of 15-epi-15-methyl-13,14-didehydro-PGF$_{2\alpha}$, methyl ester, there is prepared 15-methyl-13,14-didehydro-PGF$_{2\alpha}$, methyl ester. Accordingly, a solution of 15-methyl-14-bromo-PGF$_{2\alpha}$, methyl ester (0.41 g.) in methanol (25 ml.) is treated with 10 percent aqueous sodium hydroxide (6 ml.) and the resulting reaction is allowed to proceed overnight at ambient temperature. The corresponding acid is thereafter isolated as in the procedure described above for the preparation of 15-epimer to yield 0.34 g. of crude free acid.

Without further purification 0.32 g. of the free acid obtained above in a mixture of dimethylsulfoxide in methanol (9:1; 10 ml.) is treated with 0.43 M sodium methoxide in a mixture of dimethyl sulfoxide and methanol (9:1; 6.6 ml.). After 20 hours the resulting solution is partitioned by adding ice cold 0.2 M potassium bisulfate in benzene. The aqueous phase is extracted with the mixture of benzene and ethyl acetate (1:1) and the combined extracts are washed with brine, dried, and evaporated to yield 0.180 g. of crude 15-methyl-13,14-didehydro-PGF$_{2\alpha}$. After diazomethane esterification (following the procedure described above) crude title product is prepared which is subjected to silica gel chromatography (25 g.), eluting with acetone and methylene chloride (4:1). Thereby pure 15-methyl-13,14-didehydro-PGF$_{2\alpha}$, methyl ester (0.109 g.) is obtained. NMR absorptions are observed at 0.7–1.1, 1.1–3.5, 1.46, 3.69, 4.0–4.5, and 5.3–5.7 $\delta$. The mass spectrum shows base peak absorption at 581.3508 and other peaks at 596, 525, 506, 491, 435, 416, 345, 255, and 217. Characteristic infrared absorptions are observed at 3350, 2900, 2220, and 1740 cm$^{-1}$.

Following the procedure of Example 26, but using in place of 15-keto-PGF$_{2\alpha}$, methyl ester, each of the various 15-keto-PGF-type compounds known in the art or readily available by methods known in the art, there are prepared the corresponding 13,14-didehydro-PGF-type products. Accordingly, 3,7-inter-m-phenylene-3-oxa-4,5,6-trinor-PGF$_{1\alpha}$ is transformed to 15-keto-3,7-inter-m-phenylene-3-oxa-4,5,6-trinor-PGF$_{1\alpha}$, (employing DDQ as an oxidizing agent) and this 15-keto compound is transformed following the procedure of Example 26 to 3,7-inter-m-phenylene-3-oxa-4,5,6-trinor-13,14-didehydro-PGF$_{1\alpha}$. Likewise, 3,7-inter-m-phenylene-4,5,6-trinor-PGF$_{1\alpha}$ is transformed to 3,7-inter-m-phenylene-4,5,6-trinor-13,14-didehydro-PGF$_{1\alpha}$. Further, following the procedure described in Examples 4–16 and Example 19, but omitting the 2-chlorination of Example 4, there are prepared various PGF-type compounds which are transformed, as described above to corresponding 15-keto-PGF-type compounds. Each of these 15-keto-PGF-type compounds are transformed according to the procedure of Example 26 to the corresponding 13,14-didehydro-PGF-type compound. Accordingly, each of the various 13,14-didehydro-PGF$_{60}$-type compounds disclosed herein is prepared according to the procedure of Example 26, by selection of the appropriate PGF$_{60}$-type starting material.

EXAMPLE 27

15-Methyl-13,14-didehydro-PGE$_2$, methyl ester
(Formula CLXII: $\supset$ is

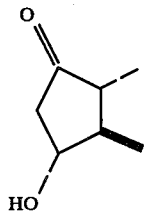

$R_1$ and $R_5$ are methyl, $R_3$ and $R_4$ of the $L_1$ moiety are hydrogen, $R_7$ is n-butyl, $R_8$ is hydroxy, Y is —C≡C—, and $Z_1$ is cis—CH≡CH—(CH$_2$)$_3$—) or its 15-epimer.

Refer to Chart H and J.

A. A solution of 15-methyl-13,14-didehydro-PGF$_{2\alpha}$, methyl ester (Example 26, 0.142 g.), in acetone (18 ml.) at −45° C. is treated with trimethylsilyldiethylamine (0.6 ml.). After 2.5 hours additional reagent (2.1 ml.) is added and the reaction is continued for 5 hours. The resulting mixture is then diluted with pre-cooled diethyl ether and partitioned with aqueous sodium bicarbonate solution. The organic layer is then dried and evaporated to a yellow oil (15-methyl-13,14-didehydro-PGF$_{2\alpha}$, methyl ester, 11-(trimethylsilyl ether).

B. The oil obtained in part A is thereafter dissolved in methylene chloride (10 ml.) and thereafter added to a solution of CrO$_3$ (0.26 g.), methylene chloride (20 ml.), and pyridine (0.4 ml.) at 0° C. This oxidation mixture is then vigorously agitated at 0° C. for 5 minutes and thereafter at ambient temperature for 10 minutes. The resulting suspension is then filtered through silica gel, with the combined filtrate and methylene chloride components being thereafter evaporated to yield 0.103 g. of 15-methyl-13,14-didehydro-PGE$_2$, methyl ester, 11-trimethylsilylether (a formula CLIII compound).

C. Crude reaction product of part B above in methanol (20 ml.) is treated with water (10 ml.) and acetic acid (1 ml.) and reacted with 5 minutes at 0° C. and thereafter stirred for 10 minutes at ambient temperature. The reaction is then diluted with diethyl ether and partitioned with 0.2 M sodium bisulfate. The organic layer is then washed with sodium chloride and sodium bicarbonate solutions, dried, and evaporated to yield 0.082 g. of crude title product.

Following the procedure described above, the corresponding 15-epimer is obtained.

For 15-methyl-13,14-didehydro-PGE$_2$, methyl ester, the mass spectrum shows base peak absorption at 407.2981 and other peaks at 522, 491, 451, 432, 361, 307, 277, and 187. For the 15-epimer, NMR absorptions are observed at 0.8–1.1, 1.1–3.2, 1.48, 3.68, 4.1–4.7 and 5.3–5.6 δ. The mass spectrum shows base peak absorption at 507.2981, 522, 491, 451, 432, 361, 307, 277, and 187. Characteristic infrared absorptions are observed at 3300, 2257, and 1740 cm.$^{-1}$.

Following the procedure of Example 27, the various 13,14-didehydro-PGF-type compounds described following Example 26 are transformed to corresponding 13,14-didehydro-PGE-type compounds.

EXAMPLE 28

15-Methyl-13,14-didehydro-PGF$_{1\alpha}$, methyl ester, or its 15-epimer.

Refer to Charts F and J.

A. A solution of 8.5 g. of PGF$_{1\alpha}$, methyl ester in dioxane (60 ml.) is treated with 2,3-dichloro-5,6-dicyano-1,4-benzoquinone (6.8 g.). The reaction proceeds for 21 hours and thereafter the suspension so formed is filtered, the filter cake being washed with dioxane and the combined filtrate and wash concentrated under reduced pressure. The residue is triturated with methylene chloride, filtered, and the solvent removed to yield 11.6 g., of crude 15-keto-PGF$_{1\alpha}$, methyl ester. Crude product is chromatographed on silica gel (450 g.), eluting with hexane and ethyl acetate (1:1). Pure compound (7.04 g.) is thereby obtained. NMR absorptions are observed at 0.89, 1.05–2.05, 2.05–2.75, 3.20–3.8, 3.67, 6.13, and 6.76 δ.

B. A solution of the reaction product of part A (7.07 g.) in pyridine (40 ml.) is treated with benzoyl chloride (6.3 ml.) and the reaction is allowed to proceed to ambient temperature for 3 hours. The resulting mixture is then diluted with ice water and extracted with methylene chloride. The methylene chloride extract is washed with solutions of ice cold dilute sulfuric acid, sodium bicarbonate, and sodium chloride. The washed extract is then dried and evaporated to yield 11.4 g. of a viscous oil. This oil is chromatographed on silica gel (200 g.) and pure product is obtained diluting with hexane in ethyl acetate (85:15). Accordingly, there is recovered pure 15-keto-9,11-dibenzoyl-PGF$_{1\alpha}$, methyl ester (10.76 g.). NMR absorptions are observed at 0.89, 1.5–1.80, 2.0–2.3, 2.3–2.7, 3.63, 5.1–5.65, 6.26, 6.92, 7.2–7.7, and 7.8–8.2 δ.

C. A solution of the reaction product of part B (4.77 g.) in carbon tetrachloride (20 ml.) is treated dropwise with a solution of bromine (8.3 mmol.) in tetrachloroethane (30 ml.) Coloration is observed to disappear in 10 minutes. The solvent is then removed under reduced pressure to yield 5.0 g. of 13,14-dibromo-9,11-dibenzoyl-15-keto-PGF$_{1\alpha}$, methyl ester. NMR absorptions are observed at 0.9, 1.10–2.0, 2.0–3.3, 3.65, 4.4–4.95, 5.08, 5.45–5.85, 7.10–7.8, and 7.9–8.2 δ.

D. The reaction product of part C (2.56 g.) in pyridine (18 ml.) is heated at 90°–95° C. for 1 hour. Thereafter the resulting dark green solution is diluted with methylene chloride, washed with ice cold 10 percent sulfuric acid, 5 percent sodium bicarbonate, and 5 percent sodium chloride solutions, dried, and evaporated. This process is then repeated for 2 additional runs and 9.0 g. of crude product is thereby recovered. Crude product is chromatographed on silica gel (210 g.), eluting with hexane and ethyl acetate (85:15). Thereby 5.5 g. of pure 14-bromo-9,11-dibenzoyl-15-keto-PGF$_{1\alpha}$, methyl ester is prepared. NMR absorptions are observed at 0.92, 1.1–2.0, 2.0–2.6, 2.6–3.1, 3.64, 5.1–5.7, 7.12, 7.2–7.7, and 7.8–8.7 δ.

E. A solution of the reaction product of part D above (0.43 g.) in tetrahydrofuran (15 ml.) is cooled at −78° C. and treated with ethereal methyl magnesium bromide (1.6 ml.) in tetrahydrofuran (10 ml.). After 3.5 hours the reaction mixture thereby obtained is poured with stirring into a cold mixture of diethyl ether and saturated ammonium chloride. The combined ethereal extracts are then washed with sodium chloride, dried and evaporated to yield 0.43 g. of crude (15RS)-15-methyl-14-bromo-9,11-dibenzoyl-PGF$_{1\alpha}$, methyl ester. Chromatographing on silica gel (25 g.), eluting with benzene in acetone (97:3) yields 0.280 g. of pure product. NMR absorptions are observed 0.83, 1.0–2.0, 1.47, 2.0–3.4, 3.63, 5.0–5.8, 6.13, 7.2–7.7, and 7.8–8.2 δ.

F. A solution of the reaction product of part E above (0.28 g.) in methanol (15 ml.) is treated with potassium carbonate (0.1 g.). The solution is stirred for 24 hours, thereafter being concentrated under reduced pressure, diluted with sodium chloride solution and extracted with ethyl acetate. Thereby, 0.197 g. of crude deacrylated product is obtained. This crude product (0.19 g.) is then chromatographed on silica gel (25 g.) eluting with methylene chloride in acetone (85:15). Thereby 43 mg. of 14-bromo-15-methyl-PGF$_{1\alpha}$, methyl ester is obtained. For the (15S) product NMR absorptions are observed at 0.88, 1.10–2.1, 1.45, 2.1–2.7, 3.67, 3.8–4.4, and 5.92 δ. Mass spectrum shows peaks at 426, 395, and 372. For the 15-epimeric product NMR absorptions are observed at 0.88, 1.10–2.1, 1.45, 2.1–2.5, 2.5–3.3, 3.67, 3.8–4.4, and 5.97 δ. The mass spectrum shows peaks at 408 and 329.

G. A solution of potassium t-butoxide (0.37 g.) in tert-butanol (15 ml.) is treated with the reaction product of part F above (0.36 g.). After 3.5 hours the reaction mixture is diluted with diethyl ether and one percent aqueous potassium bisulfate is added. The aqueous phase is extracted with diethyl ether and benzene solutions and the combined organic extracts washed with brine, dried, and evaporated to yield 0.35 g. of crude product. The crude product is then purified on silica gel eluting with 40 percent ethyl acetate in benzene. Thereby 78 mg. of 15-methyl-13,14-didehydro-PGF$_{2\alpha}$ is obtained.

Esterification of the product of the preceeding paragraph with diazomethane and thereafter chromatographing on silica gel, eluting with 12 percent acetone in methylene chloride yields 38 mg. of pure title product. The melting point is 50° C. The mass spectrum shows peaks at 598, 583, 527, 508, 469, 411, 217, and 187. Characteristic infrared absorptions are observed at 1740 and 2220.

Following the procedure of part G above 0.362 g. of 15-epi-15-methyl-14-bromo-PGF$_{1\alpha}$, methyl ester is transformed to 30 mg. of the 15-epimeric title product. NMR absorptions are observed at 0.9, 1.45, 2.1–2.4, 3.67, and 4.0–4.4 δ. The mass spectrum shows peaks at 598, 583, 508, 493, 477, 469, 411, 217, and 187. Characteristic infrared absorptions are observed at 1740 and 2240 cm.$^{-1}$.

EXAMPLE 29

13,14-Didehydro-PGF$_{1\alpha}$, methyl ester or its 15-epimer.

A. Sodium borohydride (0.44 g.) in methanol (30 ml.) at −35° C. is treated with a solution of the reaction product of example 28, part D (5.04 g.) and methanol. The solution is stirred for 20 minutes, quenched with acetic acid (20 ml.) diluted with diethyl ether, and ice cold 0.2 M sulfuric acid is added. The combined organic extracts are washed with sodium bicarbonate and saline solutions, dried, and evaporated. The crude residue, 14-bromo-(15RS)-9,11-dibenzoyl-PGF$_{1\alpha}$, methyl ester (5.0 g.) is used without further purification. NMR absorptions are observed at 0.7–1.0, 1.0–1.9, 1.9–2.3, 2.3–3.3, 3.63, 3.9–4.3, 5.0–5.6, 6.02, 7.2–7.7, and 7.2–8.2 δ.

B. A solution of the reaction product of part A above (5.0 g.) in methanol (35 ml.) is treated with potassium carbonate (1.5 g.) and agitated for 20 hours. The resulting suspension is then concentrated under reduced pressure, diluted with water, and extracted with ethyl acetate. Drying and evaporation of solvent yields 4.52 g. of crude epimerically mixed deacylated product. The aqueous phase above is acidified and extracted with ethyl acetate to yield 0.45 g. of the free acid of the above epimerically mixed acylated product. These acids are esterified with excess ethereal diazomethane and the combined methyl ester fractions are combined on silica gel eluting with methylene chloride and acetone (7:3) yielding 1.38 g. of 14-bromo-PGF$_{1\alpha}$, methyl ester and 1.23 g. of 15-epi-14-bromo-PGF$_{1\alpha}$, methyl ester. For the (15S) compound NMR absorptions are observed at 0.7–1.1, 1.1–2.0, 2.0–2.6, 2.6–3.5, 3.68, 3.75, 4.4, and 5.85 δ. The mass spectrum shows peaks at 414, 412, 360, 358, 351, 333, 279, and 278.

For the 15-epimeric product NMR absorptions are observed at 0.7–1.10, 1.1–2.0, 2.0–2.5, 2.5–3.5, 3.68, 3.8–4.5, and 5.88 δ. The mass spectrum shows peaks at 360, 258, 333, 279, and 278.

C. A suspension of 50 percent sodium hydride (0.7 g.) in dimethylsufoxide (10 ml.) is treated with tert-butanol (1.3 ml.) and stirred until the resulting effervescence is ceased. A solution of the reaction product of part B above (1.38 g.) in dimethylsulfoxide (15 ml.) is added. After 20 hours the reaction is diluted with benzene and diethyl ether (1:1), and ice cold potassium bisulfate in water is added. The layers are separated and combined. The organic extracts are washed with a sodium chloride solution, dried, and evaporated. The residue is esterified with diazomethane. The resulting crude ester product (1.13 g.) is chromatographed on silica gel and the product eluted with methylene chloride in acetone (7:3). Thereby 0.61 g. of pure title product is obtained. Melting point is 68° C. NMR absorptions are observed at 0.90, 1.1–2.0, 2.0–3.0, 3.0–3.9, 3.68, and 4.0–4.45 δ. Characteristic infrared absorptions are observed at 1740, 2250, and 3200 to 3600 cm.$^{-1}$. Mass spectrum shows peaks at 322, 319, 306, 297, 295, 294, 279, 278, 276, 250, and 222.

Following the procedure of Example 29, 1.23 g. of 15-epi-14-bromo-PGF$_{1\alpha}$, methyl ester is transformed to 0.53 g. of 15-epi-13,14-didehydro-PGF$_{1\alpha}$, methyl ester. NMR absorptions are observed 0.90, 1.1–2.0, 2.0–3.4, 3.68, and 3.9–4.7 δ. Characteristic infrared absorptions are observed at 1740, 2250, and 3450. The mass spectrum shows peaks at 350, 337, 332, 319, 306, 297, 295, 294, 279, 278, 276, 250, and 222.

EXAMPLE 30

13,14-Didehydro-PGE$_1$, methyl ester or its 15-epimer.

A. A solution of 13,14-didehydro-PGF$_{1\alpha}$, methyl ester (Example 29, 0.22 g.) in acetone (18 ml.) at −45° C. is treated with trimethylsilyldiethylamine (0.8 ml.) and the resulting mixture stirred for 3.5 hours. Additional silylating agent (0.8 ml.) is added. After 45 minutes the reaction is quenched by sodium bicarbonate solution and extracted with diethyl ether. Drying and evaporation of solvent yields 0.34 g. of crude 13,14-didehydro-PGF$_{1\alpha}$, methyl ester, 11,15-bis(trimethylsilyl ether). B. The reaction product of part A (0.6 g.) in methylene chloride (25 ml.) at 0° C. is treated with chromium trioxide (0.5 g.) methylene chloride (40 ml.) and pyridine (0.8 ml.). The oxidation conditions are then maintained (0° C.) for 5 minutes and thereafter the temperature is allowed to warm to ambient temperature for an additional 10 minutes. The resulting mixture is then diluted with methylene chloride, and filtered through silica gel. The resulting eluant is then evaporated to yield 0.41 g. of crude 13,14-didehydro-PGE$_1$, methyl ester, 11,15-bis(trimethylsilyl ether). C. The product of part B above is combined with a mixture of methanol water and acetic acid (20:10:1, 31 ml.). The reaction is allowed to proceed at 0° C. for 5 minutes and thereafter at ambient temperature for 15 minutes. The resulting product is then diluted with water and extracted with diethyl ether. The combined ethereal extracts are then washed with sodium bicarbonate and brine and dried and evaporated to yield 0.33 g. of crude title product. This crude product is then chromatographed on 25 g. of silica gel eluting with methylene chloride in acetone (9:1) yielding 80 ml. of pure 13,14-didehydro-PGE$_1$, methyl ester. Melting point is 46° C. characteristic 0.9, 1.1–2.05, 2.05–3.4, 3.67, and 4.0–4.6 δ. The mass spectrum shows absorptions at 348, 320, 319, 295, 292, and 263. The infrared absorption spectrum shows characteristic absorptions at 1675, 1740, 2220, and 3400 cm.$^{-1}$.

Following the procedure of Example 30, parts A, B, and C, 130 mg. of 15-epi-13,14-didehydro-PGF$_{1\alpha}$, methyl ester is transformed to 26.5 mg. of 15-epi title product. Characteristic infrared absorptions are observed at 1740, 2225, and 3450 cm.$^{-1}$. The mass spectrum shows peaks at 348, 320, 319, 317, 295, 292, and 263.

EXAMPLE 31

13,14-Didehydro-PGF$_{1\alpha}$ or its 15-epimer.

Potassium t-butoxide (6.79 g.) in tert-butanol (45 ml.) and methanol (8 ml.) is treated with 14-bromo-PGF$_{1\alpha}$ (3.02 g., see Example 29) and the reaction is allowed to proceed for 25 hours. The resulting reaction mixture is then diluted with diethyl ether, washed with ice cold 8 percent phosphoric acid, and the phases are separated. The aqueous phase is then extracted with benzene, and thereafter extracted with ethyl acetate. The combined organic extracts are then washed with a sodium chloride solution, dried, and evaporated to yield 2.86 g. of title product. The melting point is 74°-75° C. The mass spectrum shows a molecular ion at 642.3961 and other peaks at 627, 571, 552, 537, 481, and 436. Characteristic NMR absorptions are observed at 3150 to 3525, 2700, 2220, 1710, and 1680.

Following the procedure of the preceding paragraph, but using as starting material 15-epi-14-bromo-PGF$_{1\alpha}$ (1.84 g.) there is prepared 15-epi-13,14-didehydro-PGF$_{1\alpha}$ (1.46 g.). The melting point is 95°-96° C. NMR absorptions are observed at 0.8–1.1, 1.1–1.9, 2.0–2.8, and 3.9–4.7 δ. The mass spectrum shows base peak absorptions at 642. 4021 and other peaks at 627, 571, 552, 537, 481, and 217. The infrared absorption spectrum shows characteristic absorptions at 3150 to 3300, 2700, 2220, 1725, and 1700 cm.$^{-1}$.

EXAMPLE 34

17-Phenyl-18,19,20-trinor-13,14-didehydro-11-deoxy-PGE$_2$ (Formula CXLVI: R$_1$ is hydrogen, R$_3$ and R$_4$ of the L$_1$ moiety and R$_5$ and R$_6$ of the M$_1$ moiety are all hydrogen, R$_7$ is benzyl, Y$_1$ is —C≡C—, and Z$_1$ is cis-CH=CH—(CH$_2$)$_3$—).

Refer to Chart G.

A. Employing 2,3-dichloro-5,6-dicyano-benzoquinone, 15-keto-17-phenyl-18,19,20-trinor-PGF$_{2\alpha}$ is prepared from 17-phenyl-18,19,20-trinor-PGE$_{2\alpha}$.

B. Thereafter following the procedure of Examples 26 and 27 the reaction product of part A is transformed to 13,14-didehydro-17-phenyl-18,19,20-trinor-PGE$_2$, methyl ester.

C. Following the procedure of Example 22, the reaction product of part B is transformed to 13,14-didehydro-17-phenyl-18,19,20-trinor-PGA$_2$, methyl ester.

D. To a solution of the reaction product of part C above (0.77 g.) in pyridine (5 ml.) is added acetic anhydride (1.5 ml.). The mixture is then stirred for 4 hours under nitrogen and thereafter water (50 ml.) is added. The resulting mixture is then stirred for 55 minutes and thereafter extracted with ethyl acetate. The combined organic extracts are washed, dried, and concentrated to yield a formula CLXIII compound, 13,14-didehydro-17-phenyl-18,19,20-trinor-PGA$_2$, 15-acetate.

E. To a stirred solution of the reaction product of step D dissolved in methanol (25 ml.) at −25° C. under a nitrogen atmosphere, a solution of sodium borohydride (2 g.) in 5 ml. of water and 20 ml. of methanol is added. This resulting mixture is then stirred at −20° C. for 20 minutes and 3.5 ml. of acetic acid is thereafter cautiously added. The resulting mixture is concentrated and thereafter 50 ml. of water is added. The pH of the mixture is then adjusted to about 3 by addition of citric acid. The mixture is then extracted with dichloromethane and the combined organic extracts are washed with water and brine, dried, and concentrated to yield a formula CXLIV compound.

F. To a solution of the reaction product of part E (dissolved in acetone, 50 ml.) at −20° C., there is added dropwise with stirring over a one minute period the Jones reagent (1.5 ml.). This mixture is stirred at −20° C. for 20 minutes and thereafter 1.5 ml. of isopropanol is added and the resulting mixture is stirred at −20° C. for 10 minutes. This mixture is then diluted with 50 ml. of water and extracted with diethyl ether. The combined ethereal extracts are washed with water and brine, dried, and concentrated. The residue is then chromatographed on silica gel, eluting with acetone and methylene chloride. Those fractions containing the 15-acetate, methyl ester of the title compound are combined and concentrated.

G. To a solution of the reaction product of step F dissolved in methanol (15 ml.), there is added sodium hydroxide (0.5 g.) in 3 ml. of water and the resulting mixture is stirred at 25° C. for 17 hours. This mixture is then acidified with 10 ml. of 3N hydrochloric acid and thereafter concentrated to an aqueous residue. The residue is diluted with 25 ml. of water and extracted with diethyl ether. The combined ethereal extracts are washed with brine, dried, and concentrated. The residue is chromatographed on acid washed silica gel, eluting with ethyl acetate and hexane. Those fractions shown to contain pure title compound are combined.

Following the procedure of Example 34, each of the PGF-type compounds described herein is transformed to the corresponding 13,14-didehydro-PGA-type compound, which is in turn transformed to each of the various 13,14-didehydro-11-deoxy-PG-type compounds described herein.

EXAMPLE 35

13,14-Didehydro-16,16-dimethyl-PGF$_{2\alpha}$, methyl ester.

Refer to Chart J.

A solution of the reaction product of Example 16 in dimethyl sulfoxide (10 ml.) is treated with potassium t-butoxide (40 mg.) and reacted for 28 hours at ambient temperature. The resulting solution is then diluted with diethyl ether and poured into a mixture of ice cold potassium bisulfate and diethyl ether. This mixture is then diluted with benzene partitioned, washed with a sodium chloride solution, dried, and evaporated. The residue is then esterified with excess ethereal diazomethane. The crude methyl ester is then chromatographed on silica gel (10 g.) eluting with methylene chloride and acetone (75:35). Thereby, 0.016 g. of title product is recovered. A characteristic IR absorption (-C≡C-) is observed at 2250 cm.$^{-1}$. The mass spectrum shows peaks at 327, 320, 304, 303, 302, 295, 284, 263, 247, 245, 235, 227, and 57.

Following the procedure of Example 35, each of the various 14-halo-11-deoxy-PGF$_\alpha$- or PFG$_\alpha$-type compounds described above is transformed to a corresponding 13,14-didehydro-11-deoxy-PGF$_\alpha$- or PGF$_\alpha$-type product.

Further, following the procedures of the above Examples each of the various 13,14-didehydro-11-deoxy-PGF$_\alpha$- or PGF$_\alpha$-type products is transformed to a corresponding 13,14-didehydro-11-deoxy-PGE- or PGE-type product.

Further, following the procedure of the above Examples each of the various13,14-didehydro-11-deoxy-PGE- or PGE-type products is transformed to the corresponding 13,14-didehydro-11-PGF$_\beta$- or 11-deoxy-PGF$_\beta$-type products.

Further, following the procedure of the above Examples each of the various 13,14-didehydro-PGE-type products is transformed to the corresponding 13,14-didehydro-PGA- or PGB-type product.

EXAMPLE 36

2-Decarboxy-2-hydroxymethyl-2,2-difluoro-16-phenoxy-17,18,19,20-tetranor-13,14-didehydro-PGF$_{2\alpha}$ (Formula CXXII: D is

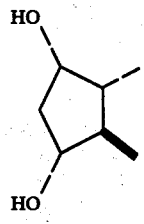

Z$_1$ is cis-CH=CH—(CH$_2$)$_2$—CF$_2$—, Y is —C≡C—, R$_7$ is phenoxy, and R$_3$ and R$_4$ of the L$_1$ moiety and R$_5$ of the M$_1$ moiety are all hydrogen).

Refer to Chart K.

A. A suspension of 2.0 g. of lithium aluminum hydride and 100 ml. of diethyl ether is prepared in a nitrogen atmosphere and thereafter a solution of 6.2 g. of 2,2difluoro-16-phenoxy-17,18,19,20-tetranor-PGF$_{2\alpha}$, 11,15-bis-(tetrahydropyranyl ether), methyl ester in 100 ml. of diethyl ether is slowly added. The reaction mixture is then stirred for 15 min. and excess reducing agent is decomposed by careful addition of ethyl acetate and water. The precipitated inorganic material is then filtered and the residue rinsed with diethyl ether. The combined ethereal extracts are then concentrated to yield crude product.

B. The crude product described in part A is then hydrolyzed by the procedure described in Example 16.

Following the procedure of Example 36, each of the various 13,14-didehydro-PGF$_\alpha$- or 13,14-didehydro-PGF$_\beta$-type compounds described is transformed to a corresponding 2-decarboxy-2-hydroxymethyl-13,14-didehydro-PGF$_\alpha$- or PGF$_\beta$-type compound.

EXAMPLE 37

2-Decarboxy-2-hydroxymethyl-5-oxa-13,14-didehydro-PGE$_2$.

Refer to Chart K.

A. Following the procedure of Example 3, Example 4, or Example 5 of the U.S. Pat. No. 3,636,120, 5-oxa-13,14-didehydro-PGE$_2$, there is prepared respectively the oxime, methoxine, or semicarbazone of the starting material.

B. Following the procedure of Example 6, or Example 7 of U.S. Pat. No. 3,636,120, the reaction product of part A of this example is transformed to a corresponding 2-de-A of this example is transformed to a corresponding 2-decarboxy-2-hydroxymethyl-PGE-type compound.

C. Following the procedure of Example 8 or U.S. Pat. No. 3,636,120 the reaction product of part B is transformed to the title product.

Following the procedure of Example 24, but employing ethyleneketalization in place of the oxime, methoxime, or semicarbazone formation part A, and deethyleneketalization in place of the oxime, methoxime, or semicarbazone removal in part C, there is prepared the title product.

Following the procedure of Example 24, but using any of the 13,14-didehydro-PGE-type compounds described above, there is prepared the corresponding 2-decarboxy-2-hydroxymethyl-13,14-didehydro-PGE-type compound.

Finally, following the procedure of Example 37, but using each of the various 13,14-didehydro-PGD, 9-deoxy-PGD, 9,10-didehydro 9-deoxy-PGD, 11-deoxy-PGE, or PGA-type compounds described above there is prepared the corresponding 2-decarboxy-2-hydroxymethyl-13,14-didehydro-PG-type compound.

EXAMPLE 38

2-Decarboxy-2-hydroxymethyl-cis-4,5-didehydro-13,14-didehydro-PGF$_{1\alpha}$,
2-decarboxy-2-hydroxymethyl-cis-4,5-didehydro-13,14-didehydro-PGE$_1$, or
2-decarboxy-2-hydroxymethyl-cis-4,5-didehydro-13,14-didehydro-PGA$_1$ (The dehydrohalogenated compounds of Formula CXXV or CXXVI Z$_6$ is cis-CH$_2$—CH=CH—(CH$_2$)$_2$—, Y$_1$ is trans-CH=C(Cl)—, M$_{18}$ is

or $\overset{O}{\underset{\|}{\phantom{X}}}$, $R_3$ and $R_4$ of the $L_1$ moiety and $R_5$ of the $M_1$ moiety are all hydrogen, and $R_7$ is n-butyl).

Refer to Chart L.

A. Following the procedure of Example 12, but using the (4-tetrahydropyranyloxybutyl)triphenylphosphonium bromide in place of 3-carboxypropyltriphenylphosphonium bromide, there is prepared 2-decarboxy-2-tetrahydropyranyloxymethyl-cis-4,5-didehydro-14-chloro-PGF$_{1\alpha}$, 11,15-bis-(tetrahydropyranyl ether).

B. Following the procedure of Example 16, the reaction product of part A is hydrolyzed to 2-decarboxy-2-hydroxymethyl-cis-4,5-didehydro-14-chloro-PGF$_{2\alpha}$, which is dehydrohalogenated to the title PGF$_{1\alpha}$ product.

C. Following the procedure of Example 17, the reaction product of part B is transformed to the corresponding PGE-type title product.

D. Following the procedure of Example 22, the reaction product of part C is dehydrated to form the title PGA$_1$-type product.

EXAMPLE 39

2-Decarboxy-2-hydroxymethyl-15-methyl-13,14-didehydro-PGF$_{2\alpha}$ or its 15-epimer.

Refer to Chart K.

A. 15-Methyl-13,14-didehydro-PGF$_{2\alpha}$, methyl ester (4.0 g.) is dissolved in 100 ml. of acetone, cooled to $-45°$ C., and treated with 15 ml. of trimethylsilyldiethylamine. The reaction mixture is then stirred at $-45°$ C. for one hr., and thereafter $-10°$ to $0°$ C. for 1.5 hr. The progress of the silylation is followed by silica gel thin layer chromatography using the following solvent system: 500 ml. of ethyl acetate, 5 ml. of methanol, and 50 ml. of water are shaken and the water layer discarded. The reaction mixture is then diluted with 500 ml. of diethyl ether and 100 ml. of methylene chloride and washed immediately with cold dilute sodium bicarbonate solution and saturated sodium chloride. The mixture is then dried over anhydrous magnesium sulfate. The solvent is then removed under reduced pressure at $40°$ C. yielding silylated product.

B. The reaction product of part A is taken up in 100 ml. of diethyl ether and added to a previously prepared suspension of 3.0 g. of lithium aluminum hydride and 100 ml. of diethyl ether. The reaction mixture is stirred for 15 min. at ambient temperature and the excess reagent decomposed by cautious addition of ethyl acetate and water. Inorganic salts are filtered from the reaction mixture and filtrate is dried and concentrated under reduced pressure at $40°$ C. to yield a 2-decarboxy-2-hydroxymethyl-PG-type silylated product.

C. The trimethylsilyl protecting groups are removed by treating a methanol solution (200 ml.) of the product of part B at $0°$ C. with 10 ml. of acetic acid and 100 ml. of water. The reaction mixture is stirred at ambient temperature for 15 min. and poured into 500 ml. of diethylether and 150 ml. of methylene chloride. The extract is then washed with ice cold dilute potassium bisulfate (3 g. in 100 ml. of water), cold dilute sodium bicarbonate, and brine. The resulting mixture is then dried over sodium sulfate, and evaporated under reduced pressure at $40°$ C., yielding crude product. This crude product is then purified chromatographically on 100 g. of E. Merck 7734 silica gel, partially deactivated with 40 ml. of ethyl acetate, yielding pure title product.

Employing 15-epi starting material, the corresponding 15-epi product is prepared.

EXAMPLE 40

2-Decarboxy-2-hydroxymethyl-2a,2b-dihomo-15-methyl-13,14-didehydro-PGF$_{2\alpha}$ or its 15-epimer.

Refer to Chart K.

To a stirred mixture of 0.67 g. of lithium aluminum hydride in 40 ml. of tetrahydrofuran is added 1.0 g. of 2a,2b-dihomo-15-methyl-13,14-didehydro-PGF$_{2\alpha}$, methyl ester in 30 ml. of dry tetrahydrofuran over a period of 13 min. The mixture is then stirred at ambient temperature for an additional 35 min. when the reaction is shown to be complete by thin layer chromatography. The mixture is then cooled in an ice bath while 10 ml. of ethyl acetate is added dropwise followed by the addition of 10 ml. of water dropwise. The mixture is then filtered and the filter cake washed with 75 ml. of ethyl acetate. The solvent is then evaporated from the combined filtrate and washings under reduced pressure at about $40°$ C. yielding an oil containing water. This material is then dissolved and the 75 ml. of ethyl acetate and dried over magnesium sulfate. Evaporation of the solvent yields crude product which is chromatographed on 50 g. of silica gel eluting with 20 percent acetone and ethyl acetate. Fractions containing pure title product are combined.

Following the procedures described above, but employing 15-epi-2a,2b-dihomo-15-methyl-PGF$_{2\alpha}$, methyl ester there is prepared 2-decarboxy-2-hydroxy-methyl-15-epi-15-methyl-PGF$_{2\alpha}$.

EXAMPLE 41

2-Decarboxy-2-hydroxymethyl-16,16-dimethyl13,14-didehydro-PGF$_{2\alpha}$.

Refer to Chart K.

A. 16,16-Dimethyl-13,14-didehydro-PGF$_{2\alpha}$ (2.8 g.) is dissolved in 70 ml. of diethyl ether and added dropwise to a suspension of 0.9 g. of lithium aluminum hydride in 30 ml. of diethyl ether. The reaction mixture is stirred at ambient temperature for 60 min. The excess reducing agent is decomposed by cautious addition of ethyl acetate and water, respectively. The organic salts are filtered and the filtrate is concentrated under reduced pressure to yield 2-decarboxy-2-hydroxymethyl-16,16-dimethyl-13,14-didehydro-PGF$_{2\alpha}$.

EXAMPLE 42

2-Decarboxy-2-hydroxymethyl-15-methyl-13,14-didehydro-PGE$_2$.

Refer to Chart H.

A. 2-Decarboxy-2-hydroxymethyl-15-methyl-13,14-didehydro-PGF$_{2\alpha}$ (2.55 g.) is dissolved in 100 ml. of acetone and treated with 15 ml. of trimethylsilyldiethylamine at $-45°$ to $-40°$ C. for 4 hr. Silylated reaction product is then recovered by the procedure described in Example 26, part A.

B. The residue obtained in part A above is treated at $15°$ C. for 15 min. with the Collins reagent. This reagent is prepared from 4.25 g. of chromium oxide, 6.9 ml. of pyridine, and 150 ml. of methylene chloride stirred at $15°-20°$ C. for 45 min. The reaction mixture is then filtered through a pad of equal parts Celite filteraid and E. Merck 7734 silica gel. The resulting mixture is then concentrated under reduced pressure and the residue taken up in benzene and filtered as described above to remove chromium salt.

C. The filtrate obtained in part B is then reconcentrated to afford crude silylated product which is dissolved in 100 ml. of water and treated at 0° C. for 15 min. with 5 ml. of acetic acid and 50 ml. of water to hydrolyze the silyl groups. This reaction mixture is then poured into 400 ml. of diethyl ether and 100 ml. of methylene chloride and washed with cold dilute sodium bicarbonate and saturated saline before drying over sodium sulfate. The extract obtained is then concentrated to yield crude product which is chromatographed over 160 g. of E. Merck 7734 silica gel partially deactivated with 65 ml. of ethyl acetate and wetted with 80 percent ethyl acetate in hexane. Accordingly, there is obtained pure title product.

EXAMPLE 43

2-Decarboxy-2-hydroxymethyl-13,14-didehydro-PGF$_{2\alpha}$, or its 15-epimer.

Refer to Chart K.

Lithium aluminum hydride (77.9 mg.) is suspended in 5 ml. of tetrahydrofuran (dried over molecular sieves) under a nitrogen atmosphere with stirring. Thereafter the suspension is cooled to about 0° C. to 110 mg. of 13,14-didehydro-PGF$_{2\alpha}$, methyl ester in 5 ml. of tetrahydrofuran is added dropwise. The reaction is monitored by silica gel thin layer chromatography using the A-IX solvent system. After about 5½ hr. the starting material is consumed and the reaction mixture acidified with addition of aqueous sodium sulfate. This resulting mixture is then diluted with 400 ml. of diethyl ether and 50 ml. of tetrahydrofuran. This diluted mixture is then stirred for an additional 30 min. and anhydrous sodium sulfate is added. This mixture is then stirred for 20 min., filtered, and concentrated under reduced pressure. Purification employing high pressure liquid chromatography (20 g. of silica gel eluting with 0.1 percent acetic acid in ethyl acetate) yields 71.0 mg. of title product. A characteristic NMR absorption is observed at 3.76 $\delta$. The mass spectrum shows parent peak at 626.4036.

Following the procedure of the preceeding paragraph, but employing 100 mg. of 15-epi-13,14-didehydro-PGF$_{2\alpha}$, methyl ester there is obtained 74.0 mg. of 2-decarboxy-2-hydroxymethyl-13,14-didehydro-15-epi-PGF$_{2\alpha}$. A characteristic NMR absorption is observed at 3.63 $\delta$. The mass spectrum shows a parent peak 626.4005.

Following the procedure of the above examples there are obtained each of the various 2-decarboxy-PGF$_\alpha$-type compounds described in the following Tables. Further, following the procedure of the above Examples there are obtained 11-deoxy-PGF$_\alpha$-, PGE-, 11-deoxy-PGE-, PGF$_\beta$-, 11-deoxy-PGF$_\beta$-, PGA-, PGD-, 9-deoxy-PGD-, and 9-deoxy-9,10-didehydro-PGD-type compounds corresponding to each of the PGF$_\alpha$-type compounds of the Tables.

In interpreting these Tables, each formula listed in the Table represents a prostaglandin-type product whose complete name is given by combining the name provided in the respective legends below the formula with the prefix found in the "Name" column in the tabular section of the Tables for each example.

TABLE A

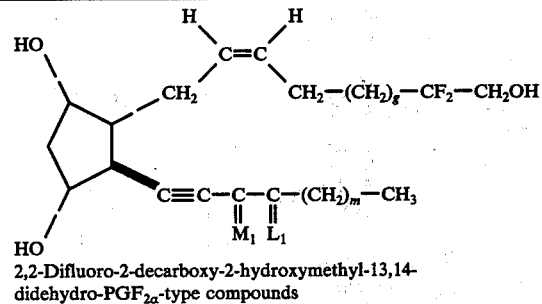

2,2-Difluoro-2-decarboxy-2-hydroxymethyl-13,14-didehydro-PGF$_{2\alpha}$-type compounds

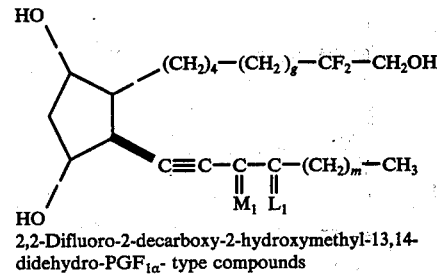

2,2-Difluoro-2-decarboxy-2-hydroxymethyl-13,14-didehydro-PGF$_{1\alpha}$- type compounds

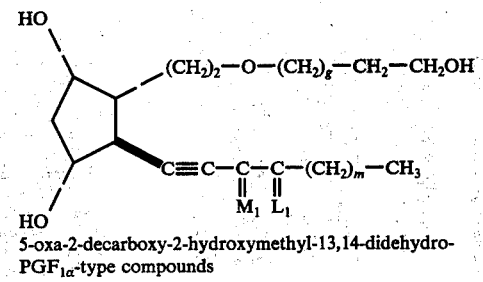

5-oxa-2-decarboxy-2-hydroxymethyl-13,14-didehydro-PGF$_{1\alpha}$-type compounds

TABLE A-continued

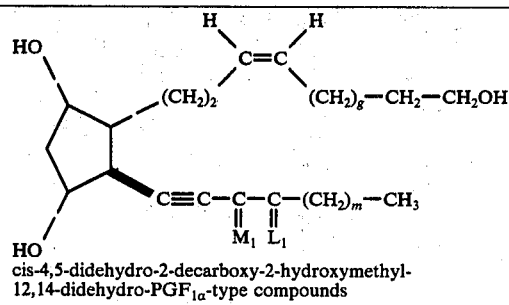
cis-4,5-didehydro-2-decarboxy-2-hydroxymethyl-
12,14-didehydro-PGF$_{1\alpha}$-type compounds

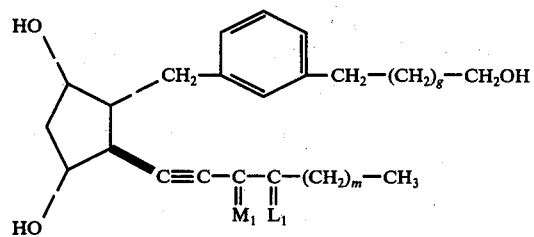
3,7-inter-m-phenylene-4,5,6-trinor-13,14-didehydro-2-decarboxy-2-hydroxymethyl-PGF$_{1\alpha}$-type compounds

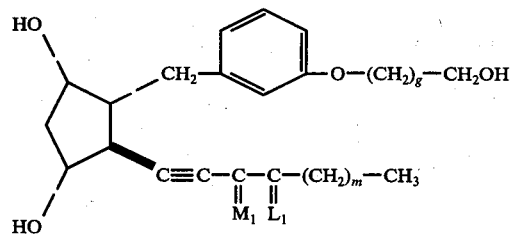
3,7-inter-m-phenylene-4,5,6-trinor-3-oxa-2-decarboxy-2-hydroxymethyl-PGF$_{1\alpha}$-type compounds

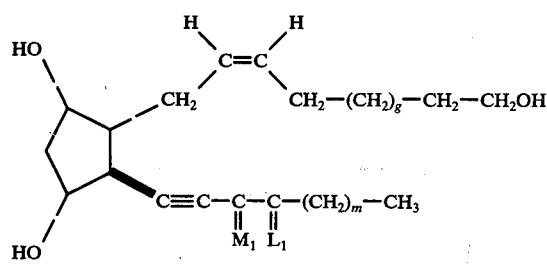
2-decarboxy-2-hydroxymethyl-13,14-didehydro-PGF$_{2\alpha}$-type compounds

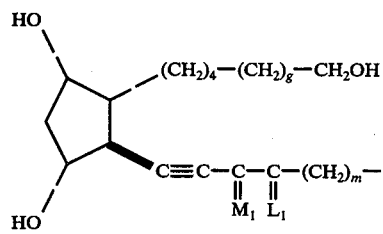
2-decarboxy-2-hydroxymethyl-13,14-didehydro-PGF$_{1\alpha}$-type compounds

| Example | g | m | L$_1$ R$_3$ | L$_1$ R$_4$ | M$_1$ R$_5$ | OH | Name |
|---|---|---|---|---|---|---|---|
| A-1 | 1 | 3 | methyl | hydrogen | hydrogen | α | 16-methyl |
| A-2 | 1 | 3 | methyl | hydrogen | methyl | α | 15,16-dimethyl |
| A-3 | 1 | 3 | methyl | methyl | hydrogen | α | 16,16-dimethyl |
| A-4 | 1 | 3 | methyl | methyl | methyl | α | 15,16,16-trimethyl |
| A-5 | 1 | 3 | fluoro | hydrogen | hydrogen | α | 16-fluoro |
| A-6 | 1 | 3 | fluoro | hydrogen | methyl | α | 15-methyl-16-fluoro |
| A-7 | 1 | 3 | fluoro | fluoro | hydrogen | α | 16,16-difluoro |
| A-8 | 1 | 3 | fluoro | fluoro | methyl | α | 15-methyl-16,16-difluoro |
| A-9 | 1 | 3 | hydrogen | hydrogen | hydrogen | α | (title compound) |
| A-10 | 3 | 3 | hydrogen | hydrogen | hydrogen | α | 2a,2b-dihomo |
| A-11 | 3 | 3 | methyl | methyl | hydrogen | α | 2a,2b-16,16-dimethyl |

TABLE A-continued

| | | | | | | | |
|---|---|---|---|---|---|---|---|
| A-12 | 3 | 3 | methyl | methyl | methyl | α | 2a,2b-dihomo-15,16,16-trimethyl |
| A-13 | 3 | 3 | fluoro | fluoro | hydrogen | α | 2a,2b-dihomo-16,16-difluoro |
| A-14 | 3 | 3 | fluoro | fluoro | methyl | α | 2a,2b-dihomo-15-methyl-16,16-difluoro |

TABLE B

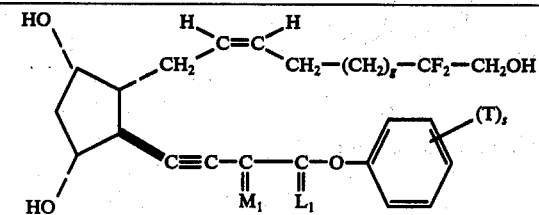

2,2-difluoro-2-decarboxy-2-hydroxymethyl-13,14-didehydro-PGF$_{2\alpha}$-type compounds

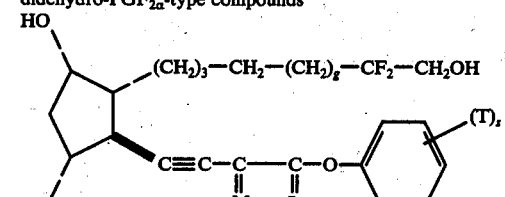

2,2-difluoro-2-decarboxy-2-hydroxymethyl-13,14-didehydro-PGF$_{1\alpha}$-type compounds

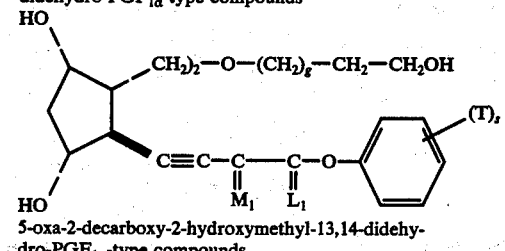

5-oxa-2-decarboxy-2-hydroxymethyl-13,14-didehydro-PGF$_{1\alpha}$-type compounds

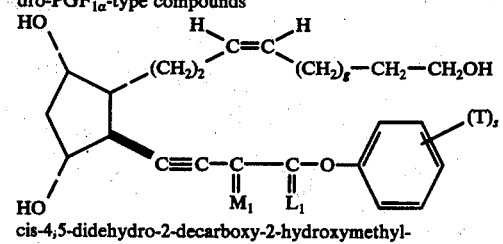

cis-4,5-didehydro-2-decarboxy-2-hydroxymethyl-13,14-didehydro-PGF$_{1\alpha}$-type compounds

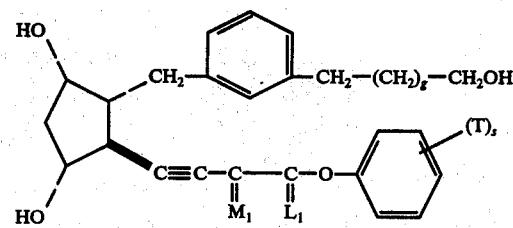

3,7-inter-m-phenylene-4,5,6-trinor-2-decarboxy-2-hydroxymethyl-13,14-didehydro-PGF$_{1\alpha}$-type compounds

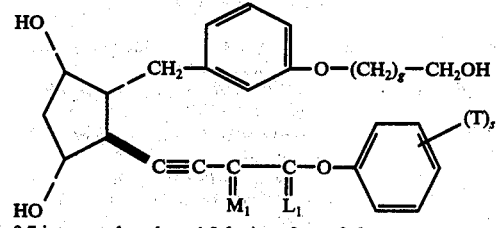

3,7-inter-m-phenylene-4,5,6-trinor-3-oxa-2-decarboxy-2-hydroxymethyl-13,14-didehydro-PGF$_{1\alpha}$-type compounds

TABLE B-continued 2-decarboxy-2-hydroxymethyl-13,14-didehydro-PGF$_{2\alpha}$-type compounds 2-decarboxy-2-hydroxymethyl-13,14-didehydro-PGF$_{1\alpha}$-type compounds

| Example | g | s | T | L$_1$ R$_3$ | L$_1$ R$_4$ | M$_1$ R$_5$ | ~OH | Name |
|---|---|---|---|---|---|---|---|---|
| A-1 | 1 | 0 | | hydrogen | hydrogen | hydrogen | α | 16-phenoxy-17,18,19,20-tetranor |
| A-2 | 1 | 1 | p-fluoro | hydrogen | hydrogen | hydrogen | α | 16-(p-fluorophenoxy)-17,18,19,20-tetranor |
| A-3 | 1 | 1 | m-chloro | hydrogen | hydrogen | hydrogen | α | 16-(m-chlorophenoxy)-17,18,19,20-tetranor |
| A-4 | 1 | 1 | m-trifluoromethyl | hydrogen | hydrogen | hydrogen | α | 16-(m-trifluoromethylphenoxy)-17,18,19,20-tetranor |
| A-5 | 1 | 0 | | hydrogen | hydrogen | methyl | α | 15-methyl-16-phenoxy-17,18,19,20-tetranor |
| A-6 | 1 | 1 | p-fluoro- | hydrogen | hydrogen | methyl | α | 15-methyl-16-(p-fluorophenoxy)-17,18,19,20-tetranor |
| A-7 | 1 | 1 | m-chloro | hydrogen | hydrogen | methyl | α | 15-methyl-16-(m-chlorophenoxy-17,18,19,20-tetranor |
| A-8 | 1 | 1 | m-trifluoromethyl | hydrogen | hydrogen | methyl | α | 15-methyl-16-(m-trifluoromethylphenoxy)-17,18,1,20-tetranor |
| A-9 | 1 | 0 | | methyl | methyl | hydrogen | α | 16-methyl-16-phenoxy-18,19,20-trinor |
| A-10 | 1 | 1 | p-fluoro | methyl | methyl | hydrogen | α | 16-methyl-16-(p-fluorophenoxy)-18,19,20-trinor |
| A-11 | 1 | 1 | m-chloro | methyl | methyl | hydrogen | α | 16-methyl-16-(m-chlorophenoxy)-18,19,20-trinor |
| A-12 | 1 | 1 | m-trifluoromethyl | methyl | methyl | hydrogen | α | 16-methyl-16-(m-trifluoromethylphenoxy)-18,19,20-trinor |
| A-13 | 1 | 0 | | methyl | methyl | methyl | α | 15,16-dimethyl-16-phenoxy-18,19,20-trinor |
| A-14 | 1 | 1 | p-fluoro | methyl | methyl | methyl | α | 15,16-dimethyl-16-(p-fluorophenoxy)-18,19,20-trinor |
| A-15 | 1 | 1 | m-chloro | methyl | methyl | methyl | α | 15,16-dimethyl-16-(m-chlorophenoxy)-18,19,20-trinor |
| A-16 | 1 | 1 | m-trifluoro- | methyl | methyl | methyl | α | 15,16-dimethyl-16-(m-trifluoromethylphenoxy)-18,19,20-trinor |
| A-17 | 3 | 0 | | hydrogen | hydrogen | hydrogen | α | 2a,2b-dihomo-16-phenoxy-17,18,19,20-tetranor |
| A-18 | 3 | 1 | p-fluoro | hydrogen | hydrogen | hydrogen | α | 2a,2b-dihomo-16-(p-fluorophenoxy)-17,18,19,20-tetranor |
| A-19 | 3 | 1 | m-chloro- | hydrogen | hydrogen | hydrogen | α | 2a,2b-dihomo-16-(m-chlorophenoxy)-17,18,19,20-tetranor |
| A-20 | 3 | 1 | m-trifluoromethyl | hydrogen | hydrogen | hydrogen | α | 2a,2b-dihomo-16-(m-trimethylphenoxy)-17,18,19,20-tetranor |
| A-21 | 3 | 1 | | hydrogen | hydrogen | methyl | α | 2a,2b-dihomo-15-methyl-16-phenoxy-17,18,19,20-tetranor |
| A-22 | 3 | 1 | p-fluoro | hydrogen | hydrogen | methyl | α | 2a,2b-dihomo-15-methyl-16-(p-fluorophenoxy)-17,18,19,20-tetranor |
| A-23 | 3 | 1 | m-chloro | hydrogen | hydrogen | methyl | α | 2a,2b-dihomo-15-methyl-16-(m-chlorophenoxy)-17,18,19,20-tetranor |
| A-24 | 3 | 1 | m-trifluoromethyl | hydrogen | hydrogen | methyl | α | 2a,2b-dihomo-15-methyl-16-(m-trifluoromethylphenoxy)-17,18,19,20-tetranor |

TABLE C

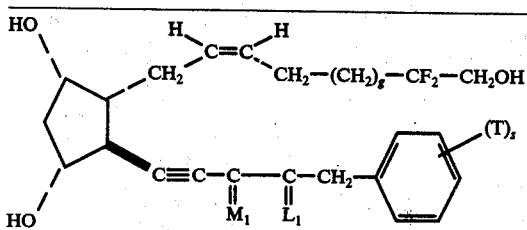

18,19,20-trinor-2,2-difluoro-2-decarboxy-2-hydroxymethyl-13,14-didehydro-$PGF_{2\alpha}$-type compounds

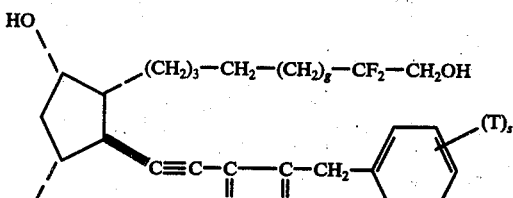

18,19,20-trinor-2,2-difluoro-2-decarboxy-2-hydroxymethyl-13,14-didehydro-$PGF_{1\alpha}$-type compounds

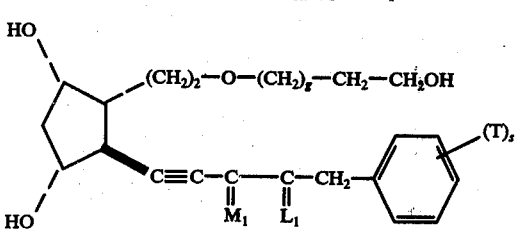

18,19,20-trinor-5-oxa-2-decarboxy-2-hydroxy-13,14-didehydro-$PGF_{1\alpha}$-type compounds

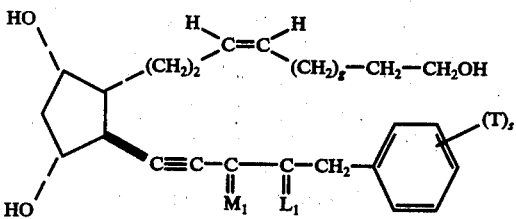

18,19,20-trinor-cis-4,5-didehydro-2-decarboxy-2-hydroxymethyl-13,14-didehydro-$PGF_{1\alpha}$-type compounds

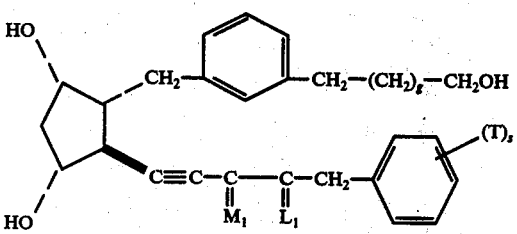

18,19,20-trinor-3,7-inter-m-phenylene-4,5,6-trinor-2-decarboxy-2-hydroxymethyl-13,14-didehydro-$PGF_{1\alpha}$-type compounds

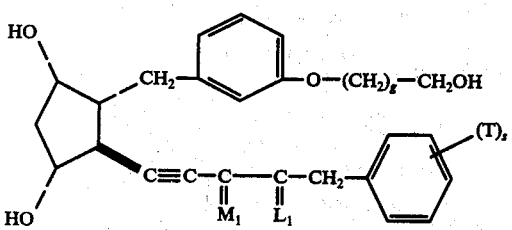

18,19,20-trinor-3,7-inter-m-phenylene-4,5,6-trinor-3-oxa-2-decarboxy-2-hydroxymethyl-13,14-didehydro-$PGF_{1\alpha}$-type compounds

TABLE C-continued

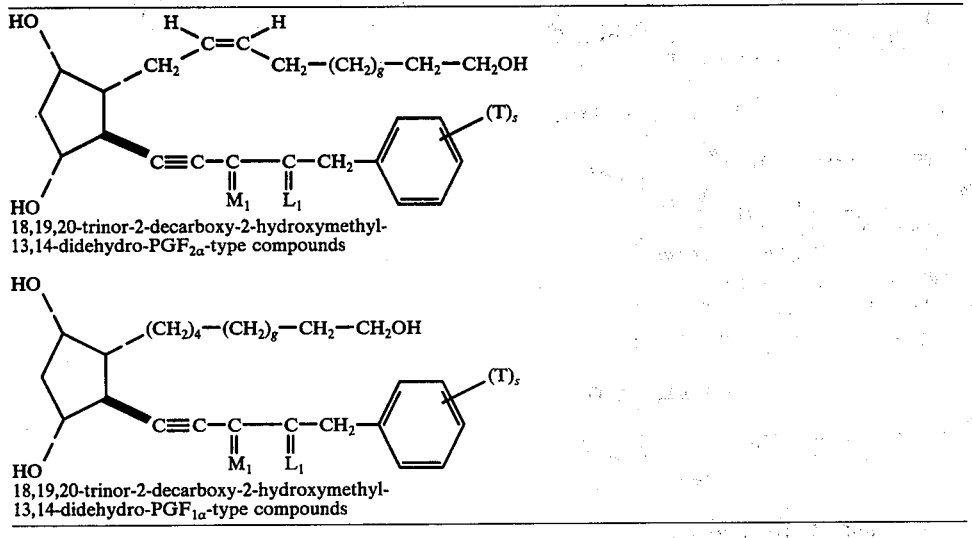

18,19,20-trinor-2-decarboxy-2-hydroxymethyl-13,14-didehydro-PGF$_{2\alpha}$-type compounds 18,19,20-trinor-2-decarboxy-2-hydroxymethyl-13,14-didehydro-PGF$_{1\alpha}$-type compounds

| Example | g | s | T | L$_1$ R$_3$ | L$_1$ R$_4$ | M$_1$ R$_5$ | ~OH | Name |
|---|---|---|---|---|---|---|---|---|
| B-1 | 1 | 0 |  | hydrogen | hydrogen | hydrogen | α | 17-phenyl |
| B-2 | 1 | 1 | p-fluoro | hydrogen | hydrogen | hydrogen | α | 17-(p-fluorophenyl) |
| B-3 | 1 | 1 | m-chloro | hydrogen | hydrogen | hydrogen | α | 17-(m-chlorophenyl) |
| B-4 | 1 | 1 | m-trifluoromethyl | hydrogen | hydrogen | hydrogen | α | 17-(m-trifluoromethylphenyl) |
| B-5 | 1 | 0 |  | hydrogen | hydrogen | methyl | α | 15-methyl-17-phenyl |
| B-6 | 1 | 1 | p-fluoro | hydrogen | hydrogen | methyl | α | 15-methyl-17-(p-fluorophenyl) |
| B-7 | 1 | 1 | m-chloro | hydrogen | hydrogen | methyl | α | 15-methyl-17-(m-chlorophenyl) |
| B-8 | 1 | 1 | m-trifluoromethyl | hydrogen | hydrogen | methyl | α | 15-methyl-17-(m-trifluoromethylphenyl) |
| B-9 | 1 | 0 |  | methyl | methyl | hydrogen | α | 16,16-dimethyl-17-phenyl |
| B-10 | 1 | 1 | p-fluoro | methyl | methyl | hydrogen | α | 16,16-dimethyl-17-(p-fluorophenyl) |
| B-11 | 1 | 1 | m-chloro | methyl | methyl | hydrogen | α | 16,16-dimethyl-17-(m-chlorophenyl) |
| B-12 | 1 | 1 | m-trifluoromethyl | methyl | methyl | hydrogen | α | 16,16-dimethyl-17-(m-trifluoromethylphenyl) |
| B-13 | 1 | 0 |  | methyl | methyl | methyl | α | 15,16,16-trimethyl-17-phenyl |
| B-14 | 1 | 1 | p-fluoro | methyl | methyl | methyl | α | 15,16,16-trimethyl-17-(p-fluorophenyl) |
| B-15 | 1 | 1 | m-chloro | methyl | methyl | methyl | α | 15,16,16-trimethyl-17-(m-chlorophenyl) |
| B-16 | 1 | 1 | m-trifluoromethyl | methyl | methyl | methyl | α | 15,16,16-trimethyl-(m-trifluoromethylphenyl) |
| B-17 | 3 | 0 |  | hydrogen | hydrogen | hydrogen | α | 2a,2b-dihomo-17-phenyl |
| B-18 | 3 | 1 | p-fluoro | hydrogen | hydrogen | hydrogen | α | 2a,2b-dihomo-17-(p-fluorophenyl) |
| B-19 | 3 | 1 | m-chloro | hydrogen | hydrogen | hydrogen | α | 2a,2b-dihomo-17-(m-chlorophenyl) |
| B-20 | 3 | 1 | m-trifluoromethyl | hydrogen | hydrogen | hydrogen | α | 2a,2b-dihomo-17-(m-trifluorophenyl) |
| B-21 | 3 | 0 |  | hydrogen | hydrogen | methyl | α | 2a,2b-dihomo-15-methyl-17-phenyl |
| B-22 | 3 | 1 | p-fluoro | hydrogen | hydrogen | methyl | α | 2a,2b-dihomo-15-methyl-17-(p-fluorophenyl) |
| B-23 | 3 | 1 | m-chloro | hydrogen | hydrogen | methyl | α | 2a,2b-dihomo-15-methyl-17-(m-chlorophenyl) |
| B-24 | 3 | 1 | m-trifluoromethyl | hydrogen | hydrogen | methyl | α | 2a,2b-dihomo-15-methyl-17-(m-trifluoromethylphenyl) |
| B-25 | 1 | 0 |  | fluoro | fluoro | hydrogen | α | 16,16-difluoro-17-phenyl |
| B-26 | 1 | 1 | p-fluoro | fluoro | fluoro | hydrogen | α | 16,16-difluoro-17-(p-fluorophenyl) |
| B-27 | 1 | 1 | m-chloro | fluoro | fluoro | hydrogen | α | 16,16-difluoro-17-(m-chlorophenyl) |
| B-28 | 1 | 1 | m-trifluoromethyl | fluoro | fluoro | hydrogen | α | 16,16-difluoro-17-(m-trifluoromethylphenyl) |
| B-29 | 1 | 0 |  | fluoro | fluoro | methyl | α | 15-methyl-16,16-difluoro-17-phenyl |
| B-30 | 1 | 1 | p-fluoro | fluoro | fluoro | methyl | α | 15-methyl-16,16-difluoro-17-(p-fluorophenyl) |
| B-31 | 1 | 1 | m-chloro | fluoro | fluoro | methyl | α | 15-methyl-16,16-difluoro-(m-chlorophenyl) |
| B-32 | 1 | 1 | m-trifluoro- | fluoro | fluoro | methyl | α | 15-methyl-16,16-difluoro-17-(m-trifluoromethylphenyl) |

TABLE C-continued methyl

I claim:
1. A prostaglandin analog of the formula:

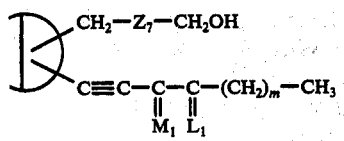

wherein  is

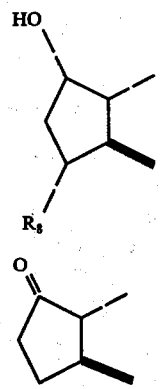

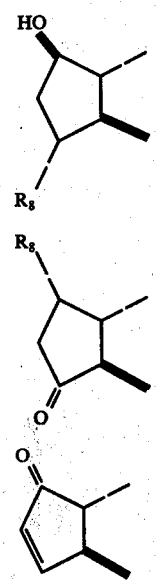

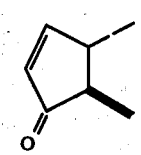, or

wherein $R_8$ is hydrogen or hydroxy;
wherein $M_1$ is

or

-continued

wherein $R_5$ is hydrogen or methyl;
wherein $L_1$ is

or a mixture of

and

wherein $R_3$ and $R_4$ are hydrogen, methyl, or fluoro, being the same or different, with the proviso that one of $R_3$ and $R_4$ is fluoro only when the other is hydrogen or fluoro;
wherein $Z_7$ is
(1) cis-CH=CH—CH$_2$—(CH$_2$)$_g$—CH$_2$—,
(2) cis-CH=CH—CH$_2$—(CH$_2$)$_g$—CF$_2$—,
(3) cis-CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—, or
(6) —CH$_2$—O—CH$_2$—(CH$_2$)$_g$—CH$_2$—,
wherein g is one, 2, or 3; and
wherein m is one to 5, inclusive.

2. A prostaglandin analog according to claim 1, wherein 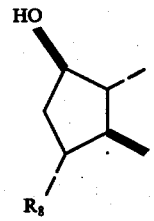 is

3. A prostaglandin analog according to claim 2, wherein $R_8$ is hydroxy.

4. A prostaglandin analog according to claim 1, wherein 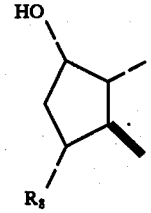 is

5. A prostaglandin analog according to claim 4, wherein $R_8$ is hydrogen.

6. A prostaglandin analog according to claim 4, wherein $R_8$ is hydroxy.

7. A prostaglandin analog according to claim 1, wherein ⟩ is

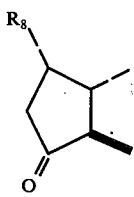

8. A prostaglandin analog according to claim 7, wherein $R_8$ is hydrogen.

9. A prostaglandin analog according to claim 7, wherein $R_8$ is hydroxy.

10. A prostaglandin analog according to claim 1, wherein ⟩ is

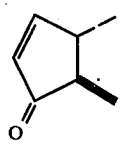

11. A prostaglandin analog according to claim 1, wherein ⟩ is

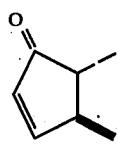

12. A prostaglandin analog according to claim 1, wherein ⟩ is

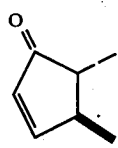

13. A prostaglandin analog according to claim 12, wherein $Z_7$ is cis-CH=CH—$CH_2$—$(CH_2)_g$—$CF_2$—.

14. 2-Decarboxy-2-hydroxymethyl-2,2-difluoro-13,14-didehydro-11-deoxy-$PGE_2$, a prostaglandin analog according to claim 13.

15. A prostaglandin analog according to claim 12, wherein $Z_7$ is —$(CH_2)_3$—$(CH_2)_g$—$CF_2$—.

16. 2-Decarboxy-2-hydroxymethyl-2,2-difluoro-13,14-didehydro-11-deoxy-$PGE_1$, a prostaglandin analog according to claim 15.

17. A prostaglandin analog according to claim 12, wherein $Z_1$ is cis-$CH_2$—CH=CH—$(CH_2)_g$—$CH_2$—.

18. 2-Decarboxy-2-hydroxymethyl-cis-4,5-didehydro-13,14-didehydro-11-deoxy-$PGE_1$, a prostaglandin analog according to claim 17.

19. A prostaglandin analog according to claim 12, wherein $Z_7$ is —$CH_2$—O—$CH_2$—$(CH_2)_g$—$CH_2$—.

20. 2-Decarboxy-2-hydroxymethyl-5-oxa-13,14-didehydro-11-deoxy-$PGE_1$, a prostaglandin analog according to claim 19.

21. A prostaglandin analog according to claim 12, wherein $Z_7$ is —$(CH_2)_3$—$(CH_2)_g$—$CH_2$—.

22. A prostaglandin analog according to claim 21, wherein $M_1$ is

23. 2-Decarboxy-2-hydroxymethyl-15-epi-13,14-didehydro-11-deoxy-$PGE_1$, a prostaglandin analog according to claim 22.

24. A prostaglandin analog according to claim 21, wherein $M_1$ is

25. A prostaglandin analog according to claim 24, wherein $m$ is 3.

26. A prostaglandin analog according to claim 25, wherein $g$ is 3.

27. 2-Decarboxy-2-hydroxymethyl-2a,2b-dihomo-15-methyl-13,14-didehydro-11-deoxy-$PGE_1$, a prostaglandin analog according to claim 26.

28. 2-Decarboxy-2-hydroxymethyl-2a,2b-dihomo-13,14-didehydro-11-deoxy-$PGE_1$, a prostaglandin analog according to claim 26.

29. A prostaglandin analog according to claim 25, wherein $g$ is 1.

30. A prostaglandin analog according to claim 29, wherein at least one of $R_3$ and $R_4$ is methyl.

31. A prostaglandin analog according to claim 30, wherein $R_3$ and $R_4$ are both methyl.

32. 2-Decarboxy-2-hydroxymethyl-16,16-dimethyl-13,14-didehydro-11-deoxy-$PGE_1$, a prostaglandin analog according to claim 31.

33. A prostaglandin analog according to claim 29, wherein at least one of $R_3$ and $R_4$ is fluoro.

34. A prostaglandin analog according to claim 33, wherein $R_3$ and $R_4$ are both fluoro.

35. 2-Decarboxy-2-hydroxymethyl-16,16-difluoro-13,14-didehydro-11-deoxy-$PGE_1$, a prostaglandin analog according to claim 34.

36. A prostaglandin analog according to claim 29, wherein $R_3$ and $R_4$ are both hydrogen.

37. A prostaglandin analog according to claim 36, wherein $R_5$ is methyl.

38. 2-Decarboxy-2-hydroxymethyl-15-methyl-13,14-didehydro-11-deoxy-$PGE_1$, a prostaglandin analog according to claim 37.

39. A prostaglandin analog according to claim 36, wherein $R_5$ is hydrogen.

40. 2-Decarboxy-2-hydroxymethyl-13,14-didehydro-11-deoxy-$PGE_1$, a prostaglandin analog according to claim 39.

41. A prostaglandin analog according to claim 12, wherein $Z_7$ is cis-CH=CH—$CH_2$—$(CH_2)_g$—$CH_2$—.

42. A prostaglandin analog according to claim 41, wherein $M_1$ is

43. A prostaglandin analog according to claim 42, wherein $m$ is 3.

44. A prostaglandin analog according to claim 43, wherein g is 3.

45. 2-Decarboxy-2-hydroxymethyl-2a,2b-dihomo-15-epi-15-methyl-13,14-didehydro-11-deoxy-PGE₂, a prostaglandin analog according to claim 44.

46. 2-Decarboxy-2-hydroxymethyl-2a,2b-dihomo-15-epi-13,14-didehydro-11-deoxy-PGE₂, a prostaglandin analog according to claim 44.

47. A prostaglandin analog according to claim 43, wherein g is 1.

48. A prostaglandin analog according to claim 47, wherein at least one of R₃ and R₄ is methyl.

49. 2-Decarboxy-2-hydroxymethyl-15-epi-16,16-dimethyl-13,14-didehydro-11-deoxy-PGE₂, a prostaglandin analog according to claim 48.

50. A prostaglandin analog according to claim 47, wherein at least one of R₃ and R₄ is fluoro.

51. 2-Decarboxy-2-hydroxymethyl-15-epi-16,16-difluoro-13,14-didehydro-11-deoxy-PGE₂, a prostaglandin analog according to claim 50.

52. A prostaglandin analog according to claim 47, wherein R₃ and R₄ are both hydrogen.

53. 2-Decarboxy-2-hydroxymethyl-15-epi-15-methyl-13,14-didehydro-11-deoxy-PGE₂, a prostaglandin analog according to claim 52.

54. A prostaglandin analog according to claim 41, wherein M₁ is

55. A prostaglandin analog according to claim 54, wherein m is 3.

56. A prostaglandin analog according to claim 55, wherein g is 3.

57. A prostaglandin analog according to claim 56, wherein at least one of R₃ and R₄ is methyl.

58. 2-Decarboxy-2-hydroxymethyl-2a,2b-dihomo-16,16-dimethyl-13,14-didehydro-11-deoxy-PGE₂, a prostaglandin analog according to claim 57.

59. A prostaglandin analog according to claim 56, wherein at least one of R₃ and R₄ is fluoro.

60. 2-Decarboxy-2-hydroxymethyl-2a,2b-dihomo-16,16-difluoro-13,14-didehydro-11-deoxy-PGE₂, a prostaglandin analog according to claim 59.

61. A prostaglandin analog according to claim 56, wherein R₃ and R₄ are both hydrogen.

62. 2-Decarboxy-2-hydroxymethyl-2a,2b-dihomo-15-methyl-13,14-didehydro-11-deoxy-PGE₂, a prostaglandin analog according to claim 61.

63. A prostaglandin analog according to claim 55, wherein g is 1.

64. A prostaglandin analog according to claim 63, wherein at least one of R₃ and R₄ is methyl.

65. A prostaglandin analog according to claim 64, wherein only one of R₃ and R₄ is methyl.

66. 2-Decarboxy-2-hydroxymethyl-16-dimethyl-13,14-didehydro-11-deoxy-PGE₂, a prostaglandin analog according to claim 65.

67. A prostaglandin analog according to claim 64, wherein R₃ and R₄ are both methyl.

68. 2-Decarboxy-2-hydroxymethyl-16,16-dimethyl-13,14-didehydro-11-deoxy-PGE₂, a prostaglandin analog according to claim 67.

69. A prostaglandin analog according to claim 63, wherein at least one of R₃ and R₄ is fluoro.

70. A prostaglandin analog according to claim 69, wherein R₃ and R₄ are both fluoro.

71. A prostaglandin analog according to claim 70, wherein R₅ is methyl.

72. 2-Decarboxy-2-hydroxymethyl-15-methyl-16,16-difluoro-13,14-didehydro-11-deoxy-PGE₂, a prostaglandin analog according to claim 71.

73. A prostaglandin analog according to claim 70, wherein R₅ is hydrogen.

74. 2-Decarboxy-2-hydroxymethyl-16,16-difluoro-13,14-didehydro-11-deoxy-PGE₂, a prostaglandin analog according to claim 73.

75. A prostaglandin analog according to claim 63, wherein R₃ and R₄ are both hydrogen.

76. A prostaglandin analog according to claim 75, wherein R₅ is methyl.

77. 2-Decarboxy-2-hydroxymethyl-15-methyl-13,14-didehydro-11-deoxy-PGE₂, a prostaglandin analog according to claim 76.

78. A prostaglandin analog according to claim 75, wherein R₅ is hydrogen.

79. 2-Decarboxy-2-hydroxymethyl-13,14-didehydro-11-deoxy-PGE₂, a prostaglandin analog according to claim 78.

80. A prostaglandin analog according to claim 1, wherein D is

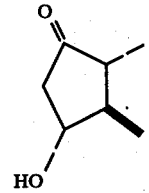

81. A prostaglandin analog according to claim 80, wherein Z₇ is cis-CH=CH—CH₂—(CH₂)ᵍ—CF₂—.

82. 2-Decarboxy-2-hydroxymethyl-2,2-difluoro-13,14-dihydro-PGE₂, a prostaglandin analog according to claim 81.

83. 2-Decarboxy-2-hydroxymethyl-2,2-difluoro-15-methyl-13,14-didehydro-PGE₂, a prostaglandin analog according to claim 81.

84. 2-Decarboxy-2-hydroxymethyl-2,2-difluoro-16,16-dimethyl-13,14-didehydro-PGE₂, a prostaglandin analog according to claim 81.

85. A prostaglandin analog according to claim 80, wherein Z₇ is —(CH₂)₃—(CH₂)ᵍ—CF₂—.

86. 2Decarboxy-2-hydroxymethyl-2,2-difluoro-13,14-didehydro-PGE₁, a prostaglandin analog accordisng to claim 85.

87. 2-Decarboxy-2-hydroxymethyl-2,2-difluoro-15-methyl-13,14-didehydro-PGE₁, a prostaglandin analog according to claim 85.

88. 2-Decarboxy-2-hydroxymethyl-2,2-difluoro-16,16-dimethyl-13,14-didehydro-PGE₁, a prostaglandin analog according to claim 85.

89. A prostaglandin analog according to claim 80, wherein Z₇ is cis-CH₂—CH=CH—(CH₂)ᵍ—CH₂—.

90. 2-Decarboxy-2-hydroxymethyl-cis-4,5-didehydro-13,14-didehydro-PGE₁, a prostaglandin analog according to claim 89.

91. 2-Decarboxy-2-hydroxymethyl-cis-4,5-didehydro-15-methyl-13,14-didehydro-PGE₁, a prostaglandin analog according to claim 89.

92. 2-Decarboxy-2-hydroxymethyl-cis-4,5-didehydro-16,16-dimethyl-13,14-didehydro-PGE$_1$, a prostaglandin analog according to claim 89.

93. A prostaglandin analog according to claim 80, wherein Z$_7$ is —CH$_2$—O—CH$_2$—(CH$_2$)$_g$—CH$_2$—.

94. 2-Decarboxy-2-hydroxymethyl-5-oxa-13,14-didehydro-PGE$_1$, a prostaglandin analog according to claim 93.

95. 2-Decarboxy-2-hydroxymethyl-5-oxa-15-methyl-13,14-didehydro-PGE$_1$, a prostaglandin analog according to claim 93.

96. A prostaglandin analog according to claim 80, wherein Z$_7$ is —(CH$_2$)$_3$—(CH$_2$)$_g$—CH$_2$—.

97. A prostaglandin analog according to claim 96, wherein M$_1$ is

98. 2-Decarboxy-2-hydroxymethyl-15-epi-13,14-didehydro-PGE$_1$, a prostaglandin analog according to claim 97.

99. A prostaglandin analog according to claim 96, wherein M$_1$ is

100. A prostaglandin analog according to claim 99, wherein m is 3.

101. A prostaglandin analog according to claim 100, wherein g is 3.

102. 2-Decarboxy-2-hydroxymethyl-2a,2b-dihomo-15-methyl-13,14-didehydro-PGE$_1$, a prostaglandin analog according to claim 101.

103. 2-Decarboxy-2-hydroxymethyl-2a,2b-dihomo-13,14-didehydro-PGE$_1$, a prostaglandin analog according to claim 101.

104. A prostaglandin analog according to claim 100, wherein g is 1.

105. A prostaglandin analog according to claim 104, wherein at least one of R$_3$ and R$_4$ is methyl.

106. A prostaglandin analog according to claim 105, wherein R$_3$ and R$_4$ are both methyl.

107. 2-Decarboxy-2-hydroxymethyl-16,16-dimethyl-13,14-didehydro-PGE$_1$, a prostaglandin analog according to claim 106.

108. A prostaglandin analog according to claim 104, wherein at least one of R$_3$ and R$_4$ is fluoro.

109. A prostaglandin analog according to claim 108, wherein R$_3$ and R$_4$ are both fluoro.

110. 2-Decarboxy-2-hydroxymethyl-16,16-difluoro-13,14-didehydro-PGE$_1$, a prostaglandin analog according to claim 109.

111. A prostaglandin analog according to claim 104, wherein R$_3$ and R$_4$ are both hydrogen.

112. A prostaglandin analog according to claim 111, wherein R$_5$ is methyl.

113. 2-Decarboxy-2-hydroxymethyl-15-methyl-13,14-didehydro-PGE$_1$, a prostaglandin analog according to claim 112.

114. A prostaglandin analog according to claim 111, wherein R$_5$ is hydrogen.

115. 2-Decarboxy-2-hydroxymethyl-13,14-didehydro-PGE$_1$, a prostaglandin analog according to claim 114.

116. A prostaglandin analog according to claim 80, wherein Z$_7$ is cis-CH=CH—CH$_2$—(CH$_2$)$_g$—CH$_2$—.

117. A prostaglandin analog according to claim 116, wherein M$_1$ is

118. A prostaglandin analog according to claim 117, werein m is 3.

119. A prostaglandin analog according to claim 118, wherein g is 3.

120. 2-Decarboxy-2-hydroxymethyl-2a,2b-dihomo-15-epi-15-methyl-13,14-didehydro-PGE$_2$, a prostaglandin analog according to claim 119.

121. 2-Decarboxy-2-hydroxymethyl-2a,2b-dihomo-15epi-13,14-didehydro-PGE$_2$, a prostaglandin analog according to claim 119.

122. A prostaglandin analog according to claim 118, wherein g is 1.

123. A prostaglandin analog according to claim 122, wherein at least one of R$_3$ and R$_4$ is methyl.

124. 2-Decarboxy-2-hydroxymethyl-15-epi-16,16-dimethyl-13,14-didehydro-PGE$_2$, a prostaglandin analog according to claim 123.

125. A prostaglandin analog according to claim 122, wherein at least one of R$_3$ and R$_4$ is fluoro.

126. 2-Decarboxy-2-hydroxymethyl-15-epi-16,16-difluoro-13,14-didehydro-PGE$_2$, a prostaglandin analog according to claim 125.

127. A prostaglandin analog according to claim 122, wherein R$_3$ and R$_4$ are both hydrogen.

128. 2-Decarboxy-2-hydroxymethyl-15-epi-15-methyl-13,14-didehydro-PGE$_2$, a prostaglandin analog according to claim 127.

129. A prostaglandin analog according to claim 116, wherein M$_1$ is

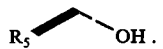

130. A prostaglandin analog according to claim 129, wherein m is 3.

131. A prostaglandin analog according to claim 130, wherein g is 3.

132. A prostaglandin analog according to claim 131, wherein at least one of R$_3$ and R$_4$ is methyl.

133. 2-Decarboxy-2-hydroxymethyl-2a,2b-dihomo-16,16-dimethyl-13,14-didehydro-PGE$_2$, a prostaglandin analog according to claim 132.

134. A prostaglandin analog according to claim 131, wherein at least one of R$_3$ and R$_4$ is fluoro.

135. 2-Decarboxy-2-hydroxymethyl-2a,2b-dihomo-16,16-difluoro-13,14-didehydro-PGE$_2$, a prostaglandin analog according to claim 134.

136. A prostaglandin analog according to claim 131, wherein R$_3$ and R$_4$ are both hydrogen.

137. 2-Decarboxy-2-hydroxymethyl-2a,2b-dihomo-15-methyl-13,14-didehydro-PGE$_2$, a prostaglandin analog according to claim 136.

138. A prostaglandin analog according to claim 130, wherein g is 1.

139. A prostaglandin analog according to claim 138, wherein at least one of R$_3$ and R$_4$ is methyl.

140. A prostaglandin analog according to claim 139, wherein only one of R$_3$ and R$_4$ is methyl.

141. 2-Decarboxy-2-hydroxymethyl-16-methyl-13,14-didehydro-PGE$_2$, a prostaglandin analog according to claim 140.

142. A prostaglandin analog according to claim 139, wherein R$_3$ and R$_4$ are both methyl.

143. 2-Decarboxy-2-hydroxymethyl-16,16-dimethyl-13,14-didehydro-PGE$_2$, a prostaglandin analog according to claim 142.

144. A prostaglandin analog according to claim 138, wherein at least one of R$_3$ and R$_4$ is fluoro.

145. A prostaglandin analog according to claim 144, wherein R$_3$ and R$_4$ are both fluoro.

146. A prostaglandin analog according to claim 145, wherein R$_5$ is methyl.

147. 2-Decarboxy-2-hydroxymethyl-15-methyl-16,16-difluoro-13,14-didehydro-PGE$_2$, a prostaglandin analog according to claim 146.

148. A prostaglandin analog according to claim 145, wherein R$_5$ is hydrogen.

149. 2-Decarboxy-2-hydroxymethyl-16,16-difluoro-13,14-didehydro-PGE$_2$, a prostaglandin analog according to claim 148.

150. A prostaglandin according to claim 138, wherein R$_3$ and R$_4$ are both hydrogen.

151. A prostaglandin analog according to claim 150, wherein R$_5$ is methyl.

152. 2-Decarboxy-2-hydroxymethyl-15-methyl-13,14-didehydro-PGE$_2$, a prostaglandin analog according to claim 151.

153. A prostaglandin analog according to claim 150, wherein R$_5$ is hydrogen.

154. 2-Decarboxy-2-hydroxymethyl-13,14-didehydro-PGE$_2$, a prostaglandin analog according to claim 153.

* * * * *

UNITED STATES PATENT OFFICE
CERTIFICATE OF CORRECTION

Patent No. 4,058,564      Dated 15 November 1977

Inventor(s) Herman W. Smith

It is certified that error appears in the above-identified patent and that said Letters Patent are hereby corrected as shown below:

Column 6, line 42, "Rosenthale, et a.," should read -- Rosenthale, et al,--
Column 11, line 58, "-$CH_2(CH_2)_g$-$CF_2$-," should read -- -$CH_2$-$(CH_2)_g$-$CF_2$-, --;
Column 13, line 52, "-$CH_2$-$CH_2)_g$-$C(R_2)_2$-" should read
-- -$CH_2$-$(CH_2)_g$-$C(R_2)_2$- --;
Column 43, line 42, "$R_{18}$ is hydrogen" should read -- $R_{16}$ is hydrogen --;
Column 44, line 57, "4,5-dimethyl-1 naphthoyl," should read
-- 4,5-dimethyl-1-naphthoyl, --; line 58, "8-benzyl-1naphthoyl," should read -- 8-benzyl-1-naphthoyl, --;
Column 48, line 23, "chlorphenyl-," should read -- chlorophenyl-, --;
Column 51, line 54, "to obtain XXX" should read -- to obtain formula XXX --
Column 57, line 67, "photophonium salt" should read -- phosphonium salt --; line 44, "chlorotrim-tolylsilane" should read -- chlorotri-m-tolylsilane --;
Column 64, line 4, "sutiable" should read -- suitable --;
Column 67, line 57, "diluent of water" should read -- a diluent of water --
Column 69, line 48, "Collings" should read -- Collins --;
Column 75, lines 18-19, "tripehenylphosphonium" should read
-- triphenylphosphonium --;
Column 76, line 49, "-1αl-cyclo-" should read -- -1α-cyclo- --;
Column 77, line 3, "-5-)m-chloro-" should read -- -5-(m-chloro- --; line 34, "$PGF_{60}$, PGE, $PGF_{62}$" should read -- PGFα, PGE, PGFβ --; line 40 and line 50, "$PGF_{60}$" should read -- PGFα --; lines 40, 51, and 52, "$PGF_{62}$" should read -- PGFβ --; line 45, "5β-" should read -- 5α- --;
Column 78, line 19, "(E 13,550)" should read -- ($\epsilon$ 13,550) --; lines 31, 38, and 45, "2γ-" should read -- 2β- --;
Column 83, line 62, "formula lactol" should read -- formula XXXI lactol --; line 63, "part above" should read -- part E above --;
Column 84, line 57, "6.0-6.0" should read -- 6.0-6.9 --;
Column 86, line 33, "Formula:" should read -- Formula XXXIX: --;
Column 96, line 53, "diethyl ester," should read -- diethyl ether, --;
Column 99, line 5, "$PGF_{60}$" should read -- PGFα --; line 23, "cis-CH≡CH-" should read -- cis-CH=CH- --;
Column 101, line 17, "methyl ester is obtained" should read
-- methyl ester, and 40 mg. of 14-bromo-15-methyl-$PGF_1α$, methyl ester is obtained --;

UNITED STATES PATENT OFFICE
CERTIFICATE OF CORRECTION

Patent No. 4,058,564     Dated  15 November 1977

Inventor(s)   Herman W. Smith

It is certified that error appears in the above-identified patent and that said Letters Patent are hereby corrected as shown below:

Column 106, line 34, "Example 8 or U.S. Pat." should read -- Example 8 of U.S. Pat. --;

Column 108, line 28, "0° C. to 110 mg." should read -- 0° C. and 110 mg. --

Column 111-112, under first formula, "12,14-didehydro-" should read -- 13,14-didehydro- --;

Column 113-114, in third formula "CH$_2$)$_2$-O-(CH$_2$)$_g$-" should read -- (CH$_2$)$_2$-O-(CH$_2$)$_g$- --;

Column 123, lines 42-45,

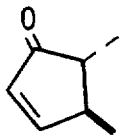   should read   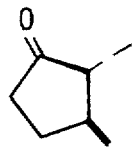

Column 125, line 58, "16-dimethyl-" should read -- 16-methyl- --;

Column 126, line 51, "2Decarboxy-2-" should read -- 2-Decarboxy-2- --; line 52, "accordisng" should read -- according --.

Signed and Sealed this

Twenty-sixth Day of May 1981

[SEAL]

Attest:

RENE D. TEGTMEYER

Attesting Officer    Acting Commissioner of Patents and Trademarks